United States Patent [19]

Keana et al.

[11] Patent Number: 5,567,411
[45] Date of Patent: Oct. 22, 1996

[54] DENDRITIC AMPLIFIER MOLECULES HAVING MULTIPLE TERMINAL ACTIVE GROUPS STEMMING FROM A BENZYL CORE GROUP

[75] Inventors: John F. W. Keana; Vladimir Martin, both of Eugene, Oreg.; William H. Ralston, St. Charles, Mo.

[73] Assignee: State of Oregon Acting by and Through the State Board of Higher Education on Behalf of the University of Oregon, Eugene, Oreg.

[21] Appl. No.: 316,787

[22] Filed: Sep. 29, 1994

Related U.S. Application Data

[60] Continuation-in-part of Ser. No. 133,652, Oct. 6, 1993, Pat. No. 5,412,148, which is a division of Ser. No. 887,542, May 22, 1992, Pat. No. 5,252,317, which is a division of Ser. No. 403,595, Sep. 5, 1989, Pat. No. 5,135,737, which is a continuation-in-part of Ser. No. 928,943, Nov. 10, 1986, Pat. No. 4,863,717.

[51] Int. Cl.⁶ .......................... C07F 11/00; A61K 49/00; A61K 49/02; C12N 9/96; C07D 209/48; C07D 207/38; C07C 69/80

[52] U.S. Cl. .......................... 424/9.1; 436/173; 436/803; 436/806; 128/653.4; 128/654; 530/391.3; 534/16; 514/241; 514/408; 514/645; 556/50; 556/61; 556/148; 544/181; 544/211; 560/35; 560/171; 562/561; 562/565; 564/26; 564/27; 564/29; 424/9.34; 424/9.35; 424/9.33; 424/9.361

[58] Field of Search .......................... 562/561, 565; 564/26, 27, 29; 544/181, 211; 560/35, 171; 530/391; 424/9; 436/173, 803, 806; 128/653, 654; 514/645, 408, 241; 556/50, 61, 148; 534/16

[56] References Cited

U.S. PATENT DOCUMENTS

| | | | |
|---|---|---|---|
| 3,507,892 | 4/1970 | Bersworth | 562/565 X |
| 4,099,918 | 7/1978 | Keana . | |
| 4,432,907 | 2/1984 | Wieder et al. | 562/565 X |
| 4,515,803 | 5/1985 | Henning et al. . | |
| 4,622,294 | 11/1986 | Kung et al. | 435/7 |
| 4,622,420 | 11/1986 | Meares et al. | 562/443 |
| 4,624,846 | 11/1986 | Goldenberg | 435/1.1 |
| 4,647,447 | 3/1987 | Gries et al. . | |
| 4,709,094 | 11/1987 | Weber et al. | 564/238 |
| 4,719,098 | 1/1988 | Weinmann et al. . | |
| 4,822,594 | 4/1989 | Gibby . | |
| 4,826,673 | 5/1989 | Dean et al. | 424/9 |
| 4,849,208 | 7/1989 | Stavrianopoulos . | |
| 4,863,717 | 9/1989 | Keana . | |
| 4,880,008 | 11/1989 | Lauffer | 128/654 |
| 4,980,147 | 12/1990 | Fritzberg et al. . | |
| 4,980,148 | 12/1990 | Dean . | |
| 4,997,913 | 3/1991 | Hellstrom et al. . | |
| 5,021,236 | 6/1991 | Gries et al. . | |
| 5,087,440 | 2/1992 | Cacheris et al. . | |
| 5,091,419 | 2/1992 | Ito et al. | 514/596 |
| 5,122,614 | 6/1992 | Zalipsky . | |
| 5,130,120 | 7/1992 | Weber . | |
| 5,135,737 | 8/1992 | Keana . | |
| 5,137,711 | 8/1992 | Weber et al. . | |
| 5,138,040 | 8/1992 | Moore et al. . | |
| 5,166,429 | 11/1992 | Ito et al. | 564/26 |
| 5,250,702 | 10/1993 | Kondo et al. | 548/842 |
| 5,252,317 | 10/1993 | Keana . | |
| 5,326,856 | 7/1994 | Coughlin et al. | 424/1.1 |
| 5,384,425 | 1/1995 | Ito et al. | 560/138 |

FOREIGN PATENT DOCUMENTS

| | | | |
|---|---|---|---|
| 0279307A2 | 8/1977 | European Pat. Off. | 435/7 |
| 2137612 | 10/1984 | United Kingdom | 435/7 |
| WO91/05762 | 5/1991 | WIPO | 562/565 |

OTHER PUBLICATIONS

Borman, "Bioconjugate Chemistry Attracts Growing Interest," *Chem. and Eng. News* (May 8, 1989), p. 25.

Curtet et al., "Selective Modification of NMR Relaxation Time in Human Colorectal Carcinoma by Using Gadolinium–Diethylenetriaminepentaacetic Acid Conjugated with Monoclonal Antibody 19–9," *Proc. Natl. Acad. Sci. USA* 83:4277 (1986).

Ehman et al., "Enhanced MRI of Tumors Utilizing a New Nitroxyl Spin Label Contrast Agent," *Mag. Res. Imaging* 3:89 (1985).

Keana and Prabhu, "Trans–2,5–Dimethyl–2,5–bis(3–aminopropyl)–pyrrolidinyl–1–oxy: A Trans–Diamino Azethoxyl Nitroxide," *J. Org. Chem.* 51:4300 (1986).

Keana and Ogan, "Functionalized Keggin– and Dawson–Type Cyclopentadienyltitanium Heteropolytungstate Anions: Small, Individually Distinguishable Labels for Conventional Transmission Electron Microscopy. 1. Synthesis," *J. Am. Chem. Soc.* 108:7951 (1986).

(List continued on next page.)

*Primary Examiner*—Floyd D. Higel
*Attorney, Agent, or Firm*—Klarquist Sparkman Campbell Leigh & Whinston, LLP

[57] ABSTRACT

Dendritic derivatives of 3,5-bis(aminomethyl)benzene and aminomethyl benzene core groups are disclosed. In each derivative, termed an "amplifier" because the dendritic structure on each molecule terminates with multiple termini to each of which an "active group" can be attached, the desired effect of the active group per mole is amplified compared to conventional compounds having only one active group per molecule. Amplifier molecules can include a targeting group permitting the molecules to preferentially attach to a particular anatomical or physiological situs. Active groups are any of various pharmacologically or therapeutically active moieties, including moieties useful for magnetic-resonance contrast enhancement. The dendritic structures comprise linkers and branch groups covalently bonded to each other in any of various structural combinations. The amplifiers can be prepared as a solution or mixture with a physiologically compatible carrier for administration to a warm-blooded animal subject. Also disclosed are methods for using the compounds in diagnosis and therapy, such as obtaining a magnetic resonance image of a subject.

30 Claims, 4 Drawing Sheets

OTHER PUBLICATIONS

Keana et al., "Functionalized Keggin– and Dawson–Type Cyclopentadienyltitanium Heteropolytungstate Anions: Small, Individually Distinguishable Labels for Conventional Transmission Electron Microscopy. 2. Reactions," *J. Am. Chem. Soc.* 108:7957 (1986).

Keana et al., "Nitroxides as Potential Contrast Enhancing Agents for MRI Application: Influence of Structure on the Rate of Reduction by Rat Hepatocytes, Whole Liver Homogenate, Subcellular Fractions, and Ascorbate," *Mag. Res. in Med.* 5:525 (1987).

Keana et al., "Synthesis of Spiro Heterocyclic Nitroxides Derived from 4–Piperidone," *J. Org. Chem.* 53:2365 (1988).

Keana et al., "Synthesis and Chemistry of N–Oxygenated Pyrroles: Crystal and Molecular Structure of a Highly Stable N–Hydroxypyrrole 18–Crown Ether Hydrate," *J. Org. Chem.* 53:2268 (1988).

Keana and Pou, "Synthesis and Properties of Some Nitroxide $\alpha$–Carboxylate Salts," *J. Org. Chem.* 54:2417 (1989).

Newkome et al., "Cascade Molecules: Synthesis and Characterization of a Benzene[9]3–Arborol," *J. Am. Chem. Soc.* 108:849 (1986).

Swyers, "Monoclonal Antibodies Have Diagnostic Therapeutic Potential," *Res. Resources Reporter*, U.S. Dept. of Health and Human Services, vol. XIII, No. 4, pp. 7–9 (Apr., 1989).

Unger et al., "Magnetic Resonance Imaging Using Gadolinium Labeled Monoclonal Antibody," *Investig. Radiol.* 20:693 (1985).

Wesbey et al., "Paramagnetic Pharmaceuticals for Magnetic Resonance Imaging," *Physiol. Chem. & Phys. & Med. NMR* 16:145 (1984).

Westerberg et al., "Synthesis of Novel Bifunctional Chelators and Their Use in Preparing Monoclonal Antibody Conjugates for Tumor Targeting," *J. Med. Chem.* 32:236 (1989).

Reddy et al., Chemical Abstracts, vol. 106, abstract 33439k (1987).

Keana, "Synthesis and Chemistry of Nitroxide Spin Labels," *Spin Labeling in Pharmacol.*, chapter 1 (1984).

Kozak et al., "Radionuclide–conjugated Monoclonal Antibodies: A Synthesis of Immunology, Inorganic Chemistry, and Nuclear Science," *Tibtech*, pp. 259–264 (Oct., 1986).

Koppel, "Recent Advances with Monoclonal Antibody Drug Targeting for the Treatment of Human Cancer," *Bioconjugate Chem.* 1:13–23 (1990).

Lauffer, "Paramagnetic Metal Complexes as Water Proton Relaxation Agents for NMR Imaging: Theory and Design," *Chem.* 87:901–927 (1987).

Keana et al., "Novel Contrast Enhancing Agents Consisting of Several Paramagnetic Centers and a Reactive Site for Attachment to other Biomolecules," (Abstract of Presentation at Seventh Annual Meeting of the Society of Magnetic Resonance in Medicine, San Francisco, California, Aug. 22–26, 1988).

O'Sullivan, "Dendrimers Nearing Availability for Commerical Evaluation," *C&EN*, pp. 20–23 (1993).

Williams et al., "Synthesis of Enantiomerically Pure Diethylenetriaminepentaacetic Acid Analogues. L–Phenylalanine as the Educt for Substitution at the Central Acetic Acid," *J. Org. Chem.* 58:1151–1158 (1993).

Sessler et al., "Gadolinium(III) Texaphyrin: A Novel MRI Contrast Agent," *J. Am. Chem. Soc.* 115:10368–10369 (1993).

Rocklage, et al., "Chelates of Gadolinium and Dysprosium as Contrast Agents for MR Imaging," *JMRI* 3:167–178 (1993).

Vallet et al., "Relaxivity Enhancement of Low Molecular Weight Nitroxide Stable Free Radicals: Importance of Structure and Medium," *MRM* 32:11–15 (1994).

Wiener et al., "Dendrimer–Based Metal Chelates: A New Class of Magnetic Resonance Imaging Contrast Agents," *MRM* 31:1–8 (1994).

DENDRITIC AMPLIFIER MOLECULES HAVING MULTIPLE TERMINAL ACTIVE GROUPS STEMMING FROM A BENZYL CORE GROUP

CROSS REFERENCE TO RELATED APPLICATION

This application is a continuation-in-part of U.S. patent application Ser. No. 08/133,652, filed Oct. 6, 1993, now U.S. Pat. No. 5,412,148; which is a divisional of U.S. patent application Ser. No. 07/887,542, filed May 22, 1992, and now U.S. Pat. No. 5,252,317; which is a divisional of U.S. patent application Ser. No. 07/403,595, filed Sep. 5, 1989, and now U.S. Pat. No. 5,135,737; which is a continuation-in-part of U.S. patent application Ser. No. 06/928,943, filed Nov. 10, 1986, and now U.S. Pat. No. 4,863,717.

BACKGROUND OF THE INVENTION

The efficacy of a medical diagnostic or therapeutic procedure employing a chemical agent is often dependent upon achieving an effective concentration of the chemical agent in the subject. I.e., a more intense effect is frequently exhibited by a higher dose (i.e., by providing a higher concentration of the agent in the subject's body), at least up to a limit usually dictated by toxicological concerns and/or undesirable side effects.

Many diagnostic and chemical agents, particularly diagnostic agents, have molecular structures that comprise an "active group" (i.e., a chemical moiety that is directly responsible for the desired diagnostic or chemotherapeutic effect) connected to other molecular structure(s) useful for any of a variety of purposes such as, but not limited to, solubility of the agent, absorption of the agent, physiological transport of the agent (such as through biological membranes), biotransformation of the agent, or targeting of the agent to a particular situs in the subject. The vast majority of such agents have only one active group per molecule of the agent.

Administering higher doses of conventional agents to achieve maximal therapeutic or diagnostic effect may not always be possible because of various undesirable dose-related effects. In certain instances these effects are related simply to the number of molecules of the agent present in the subject's body. If it were possible to simply reduce the number of molecules without decreasing the effect, many such problems could be either eliminated or substantially reduced.

As an example of a diagnostic technique that typically employs a chemical agent as described above is "Magnetic Resonance Imaging" (MRI). This technique employs the general principles of Nuclear Magnetic Resonance (NMR). NMR is based on the behavior of atomic nuclei that have non-zero nuclear spins (i.e., I not equal to zero), e.g., $^1$H, $^{13}$C, and $^{31}$p. When such nuclei are placed in an externally applied magnetic field, their rotations about their respective internal axes (i.e., their "spins") cause them to precess at a particular frequency in the external field.

MRI images are obtained by placing a subject in an external magnetic field and detecting the effect on nuclear spins as the external field is manipulated. Manipulation of the external field is usually performed using pulsed radio-frequency (RF) energy. The RF energy is at the precession frequency of the targeted nuclei. As a result, certain nuclei absorb the energy. At the end of an RF pulse, the precessing nuclei emit the absorbed energy as they relax back to equilibrium. The emitted energy is received by the RF coils used for image formation.

The time required for the nuclei to relax after an RF pulse ends is measured. This time is profoundly affected by the immediate chemical surroundings of each emitting nucleus. For example, hydrogen nuclei associated with fats have substantially different relaxation characteristics compared with hydrogen nuclei associated with water.

MRI images reflect certain intrinsic variables associated with nuclear spins within tissues. One intrinsic variable is termed the longitudinal, or T1, relaxation. Another is the transverse, or T2, relaxation. T1 and T2 relaxations occur over discrete amounts of time that can be deliberately manipulated.

The contrast of MRI images can be substantially enhanced by using contrast-enhancing agents. Certain of these agents produce marked shortening of the T1 relaxation time in the tissues where the agents can localize in sufficient concentrations. Such shortening of the T1 relation time produces high signal on T1-weighted images. Other agents can affect the T2 relaxation time, or both the T1 and T2 relaxation times.

The only contrast-enhancing agent enjoying substantial clinical use is gadolinium-DTPA, a type of gadolinium chelator. Gadolinium is particularly favored because it has seven unpaired electrons that produce an especially strong paramagnetic effect on adjacent water protons, which causes marked T1 relaxation acceleration (i.e., shortening of T1 relaxation time). Since paramagnetic metal ions useful for relaxivity enhancement are usually toxic, placing such ions in physiologically compatible complexes reduces their toxicity without substantially reducing their effectiveness.

Certain compounds termed nitroxides are also receiving considerable attention as MRI contrast-enchancing agents. Nitroxides are among few examples of organic paramagnetic compounds. Generally, organic compounds have closed electron shells in which all the electrons are paired; such compounds are generally termed "diamagnetic." Only compounds having unpaired electrons can be paramagnetic; such compounds, also termed "free radicals," are usually highly reactive and thus normally cannot be isolated. Nitroxides, also termed "nitroxide free radicals," are unusual organic free radicals because many nitroxides can be synthesized, handled, and utilized as conventional organic compounds. However, due to the presence of at least one unpaired electron in each nitroxide compound, these compounds can act as MRI contrast enhancers.

As with most other chemotherapeutic and diagnostic agents, as discussed above, conventional MRI contrast-enhancing agents have only one chelator or nitroxide group per molecule. These agents are typically short-lived in the subject's body or other physiological environments. Thus, in many instances, large doses must be administered in order to achieve a desired degree of contrast enhancement. In other instances, maximal contrast enhancement cannot be achieved without administering a potentially fatal or otherwise physiologically intolerable dose to the subject. Another problem is that nitroxides tend to be rapidly reduced in the body. Heretofore, reduction problems have been addressed by administering large amounts of the agent to the subject with the intent of "swamping" the reduction reaction. Unfortunately, such large doses of nitroxides can be toxic and/or cause osmotic disequilibria in the body.

In J. F. W. Keana's U.S. Pat. Nos. 5,135,737 and 5,252,317, incorporated herein by reference, certain molecules termed "amplifiers" or "amplifier molecules" are described.

Each molecule of such amplifier molecules has multiple diagnostically or therapeutically active groups (such as, but not limited to, nitroxides or paramagnetic metal-ion chelators). Thus, administering a particular number of molecules of such amplifiers results in a more enhanced effect than administering an equal number of conventional molecules having only one active group per molecule. Also, fewer individual "particles" need be administered to achieve an acceptable effect when amplifiers are used. This is important in the control of the osmolarity of an administered solution of the agent. More particles can result in a greater imbalance in osmolarity and thus greater pain sensation during administration of the compound. Because amplifiers used for contrast enhancement are generally larger than conventional molecules, amplifiers have a slower, more optimal "tumbling rate" which leads to greater enhancement per paramagnetic center.

Despite the foregoing, there is an ongoing need, and thus an ongoing effort to find, other amplifiers having optimal properties of maximal contrast enhancement per mole and lowest possible toxicity.

SUMMARY OF THE INVENTION

According to one aspect of the present invention, compounds are provided having the following basic structure:

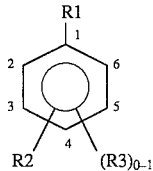

The foregoing basic structure is termed a "core group" in which R2 (and R3 if present) are substituted amines. (The "0-1" subscript means that R3 can be present or absent.) When both are present, R2 and R3 are typically, but not necessarily, the same. When R3 is absent, R2 can be ortho, meta, or preferably para to R1. When both R2 and R3 are present, they are preferably, but not necessarily, at the 3 and 5 positions, respectively. R1 can be the same as or, preferably, different from R2 and R3. Preferably, the core group has a structure selected from the following:

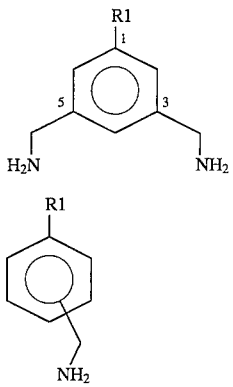

Most preferably, the core group has the structure 1A, above.

In instances in which R1 is different from R2 and R3, R1 has the structure $-(R4)_{0-1}-(R5)_{1-0}-R6(-R7)_{0-1}$, wherein the "0-1" subscript denotes that the corresponding group can be present or absent. It will be understood that, whenever the corresponding group is absent, it is simply replaced by a covalent bond. R4 can be any of the following: C(O)—NH, C(S)—NH, C(O), O, NH—C(O), NH—C(S), NH—C(S)—NH, NH—C(O)—NH, C(O)—O, or O—C(O). R5 can be any of the following: an aryl group, an aryl-($C_1$–$C_{20}$ alkyl) group, a ($C_1$–$C_{20}$ alkyl)-aryl group, a cycloalkyl group, a $C_1$–$C_{20}$ alkyl group, or a combination of these groups. R6 can be any of the following: R4, H, $C_1$–$C_6$ alkyl, C(O)—OH, C(O)—O—($C_1$–$C_6$ alkyl), C(O)—O$^-$X$^+$, $NH_2$, $NO_2$, NCS, NCO, OH, SH, or B(OH)$_2$, wherein X is a monovalent metal cation. R7 can be a "targeting group," as defined herein, i.e., any organic or bioorganic molecule having a tissue-targeting property. Representative R7 groups (not intended to be limiting in any way), as gleaned from a voluminous research literature, include: a polypeptide, a protein, an antibody, a nucleic acid, a carbohydrate, a fatty acid, a surfactant, a glyceride (di- or tri-), a porphyrin, an enzyme-inhibitor, or asteroid.

As substituted amines, R2 and R3 have the structure:

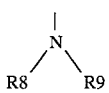

wherein R8 and R9 can be the same or different. R8 and R9 can be a hydrogen or a group having the structure R10—(R11)—(R12)$_{0-1}$(R13)$_n$, wherein n is either 1 or 2. At least one of R8 and R9, however, has the R10—(R11)—(R12)$_{0-1}$(R13)$_n$ structure. R10 is at least one structure selected from a group consisting of "linkers" and "branch groups" (as defined herein). When R10 comprises more than one linker and/or branch group, each of said linkers and/or branch groups is covalently bonded together in a series manner to form R10. R11 can be any of the following groups:—NH—C(O)—, —C(O)—NH—, —C(O)—, —NH—C(S)—, —C(S)—NH—, —NH—C(O)—NH—, —NH—C(S)—NH—, —NH—C(O)—O—; —O—C(O)—NH—, —C(O)—O—, or —O—C(O)—. R12 can be an aryl group, a $C_1$–$C_{12}$ alkyl group, a ($C_1$–$C_{12}$ alkyl)-aryl group, a cycloalkyl group, an aryl-($C_1$–$C_{12}$ alkyl) group, or a combination thereof. Finally, R13 is an "active group," as defined herein.

Linkers preferably have the structure —(R14)$_{0-1}$—R15— or, alternatively, —R15—(R14)$_{0-1}$(i.e., linkers can have either of two opposing orientations). R14 can be an aryl group, a $C_1$–$C_{12}$ alkyl group, a cycloalkyl group, an aryl-($C_1$–$C_{12}$ alkyl) group, a ($C_1$–$C_{12}$ alkyl)-aryl group, or a combination of these groups covalently bonded together in a series manner. R15 can be any of the following groups: C(O)—NH, C(S)—NH, C(O), NH—C(O), NH—C(S), NH—C(S)—NH, NH—C(O)—NH, NH—C(O)—O, O—C(O)—NH, C(O)—O, or O—C(O).

Branch groups preferably have any of the following structures:

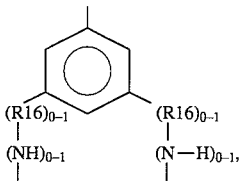

-continued

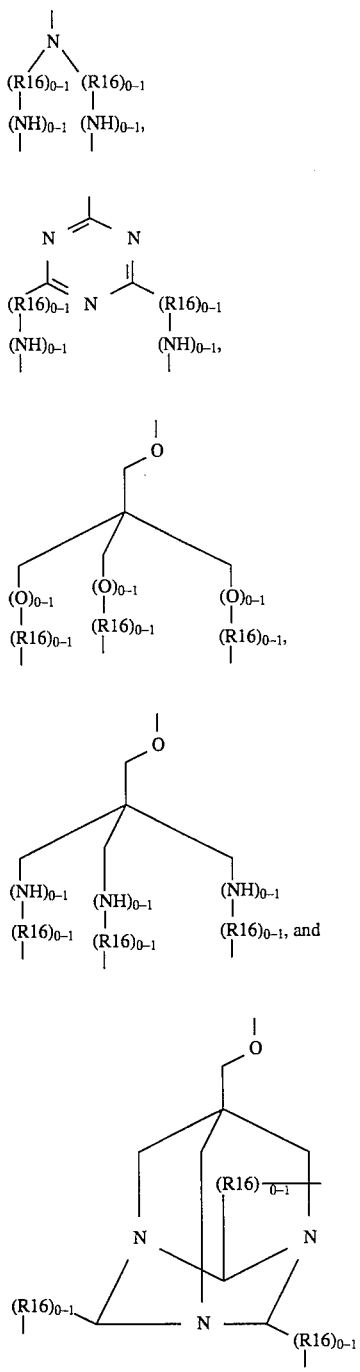

Thus, as can be seen, branch groups have either two arms (and thus function as a "Y") or three arms (and thus function as a "ψ"). In the foregoing branch groups, R16 is a $C_1$–$C_6$ alkyl group.

When R10 consists of more than one linker or branch group (or both types of groups), the linkers and/or branch groups in each R10 group are covalently bonded together in a series manner. Any branch group(s) present in an R10 group is oriented such that the arms extend away from the core group.

As can be determined from the foregoing, compounds according to the present invention are dendritic (i.e., branched) in nature, wherein the dendritic structure preferably exists on R2 and R3 (if present), but not on R1. The branching can be symmetrical or non-symmetrical. As a result of the dendritic nature of these compounds, they are termed "amplifiers" or "amplifier compounds" because each molecule has more than one active group, each located at a dendrite terminus. The presence of more than one active group per molecule effectively "amplifies," relative to conventional compounds having only one active group per molecule, the property conferred by the active group.

According to another aspect of the present invention, the active groups in compounds according to the present invention preferably enable the compounds to serve as contrast-enhancing agents for MRI, especially of warm-blooded animal subjects. Active groups particularly suitable for such a purpose include any of various paramagnetic metal-ion chelators and nitroxides. Such amplifiers are particularly effective for this use because fewer molecules of an amplifier compound need be administered to the subject, compared to conventional MRI contrast agents, in order to obtain the same degree of contrast enhancement obtained with conventional agents having only one active group per molecule.

According to yet another aspect of the present invention, the amplifiers can be either attached to or include other molecules, including any of various biomolecules, using chemistry as disclosed herein. Such attachment can be by covalent bonding or non-covalent bonding. Examples of the latter include electrostatic interactions and "hydrophobic" bonds (i.e., by intermolecular van der Waals forces having especial strength when hydrophobic regions closely associate with other hydrophobic domains in an aqueous environment). As summarized above, the R1 group can include a biomolecule or a chemical group enabling the amplifier to be attached to a biomolecule. Thus, for example, an amplifier according to the present invention can be made to "target" a specific tissue in a warm-blooded animal subject, such as by attaching the amplifier to a monoclonal antibody having immunological specificity to the particular tissue. Alternatively, other targeting devices may be used such as attachment of the amplifier to a porphyrin or other tumor-seeking moiety.

According to yet another aspect of the present invention, the amplifiers can be provided in a physiologically compatible carrier, including such a carrier suitable for administering the amplifier to a warm-blooded animal subject. For example, such a carrier can be a physiological (i.e., "isotonic") saline solution. Any of various other carriers can also be used, depending upon, for example, the particular subject, the administration route, and the desired situs in the subject's body.

According to yet another aspect of the present invention, a particularly effective amplifier for MRI contrast enhancement is provided having the structure:

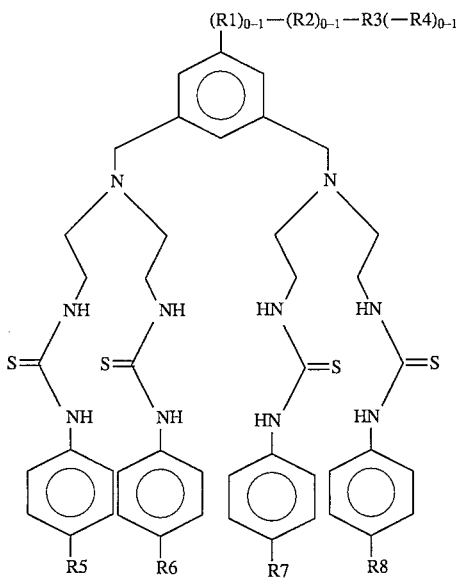

$(R1)_{0-1}$—$(R2)_{0-1}$—$R3(-R4)_{0-1}$

In the foregoing compound, R1 is any of the following: C(O)—NH, C(S)—NH, C(O), O, NH—C(O), NH—C(S), NH—C(S)—NH, NH—C(O)—NH, C(O)O, or O—C(O). R2 can be an aryl group, an aryl-($C_1$-$C_{20}$ alkyl) group, a ($C_1$-$C_{20}$ alkyl)-aryl group, a cycloalkyl group, or a $C_1$-$C_{20}$ alkyl group. R3 can be any of the following: R1, H, $C_1$-$C_6$ alkyls, C(O)—OH, C(O)—O—($C_1$-$C_6$ alkyls), C(O)—O$^-$ $X^+$, $NH_2$, $NO_2$, NCS, NCO, OH, SH, or $B(OH)_2$, wherein X is a monovalent metal cation. R4 can be a targeting group. Representative R4 groups (not intended to be limiting), as gleaned from a voluminous research literature, include: polypeptides, antibodies, proteins, nucleic acids, carbohydrates, fatty acids, surfactants, glycerides, porphyrins, enzyme-inhibitors, and steroids. R5–R8, which can be the same or different, can be any active group but are preferably each a nitroxide or a paramagnetic metal-ion chelator.

According to yet another aspect of the present invention, methods are provided for obtaining an MRI image of tissues in a warm-blooded animal subject. Such methods generally comprise the steps of providing molecules of an amplifier compound according to the present invention on which compound the active groups are nitroxides or paramagnetic metal-ion chelators. The compound is added to a physiologically compatible carrier to form a solution or suspension of the compound. The solution or suspension is administered to the subject, after which an MRI image of the subject is obtained. Such methods can be readily adapted, by providing amplifier compounds according to the present invention terminating with multiple active groups having other pharmaceutical or diagnostic activity, for use in performing chemotherapy or a diagnostic procedure involving the subject.

BRIEF DESCRIPTION OF THE DRAWINGS

FIGS. 3A–3D are photographs obtained during a magnetic-resonance angiography study of a rat to which the tetragadolinium complex 303 (shown in Scheme 24) had been administered, wherein FIGS. 3A–3D are images obtained prior to and 15, 30, and 45 minutes after injection, respectively, of 10 micromoles complexed gadolinium per kg body weight of a 20 mM complexed gadolinium solution, as described in Example 116.

DETAILED DESCRIPTION

Figure 1:
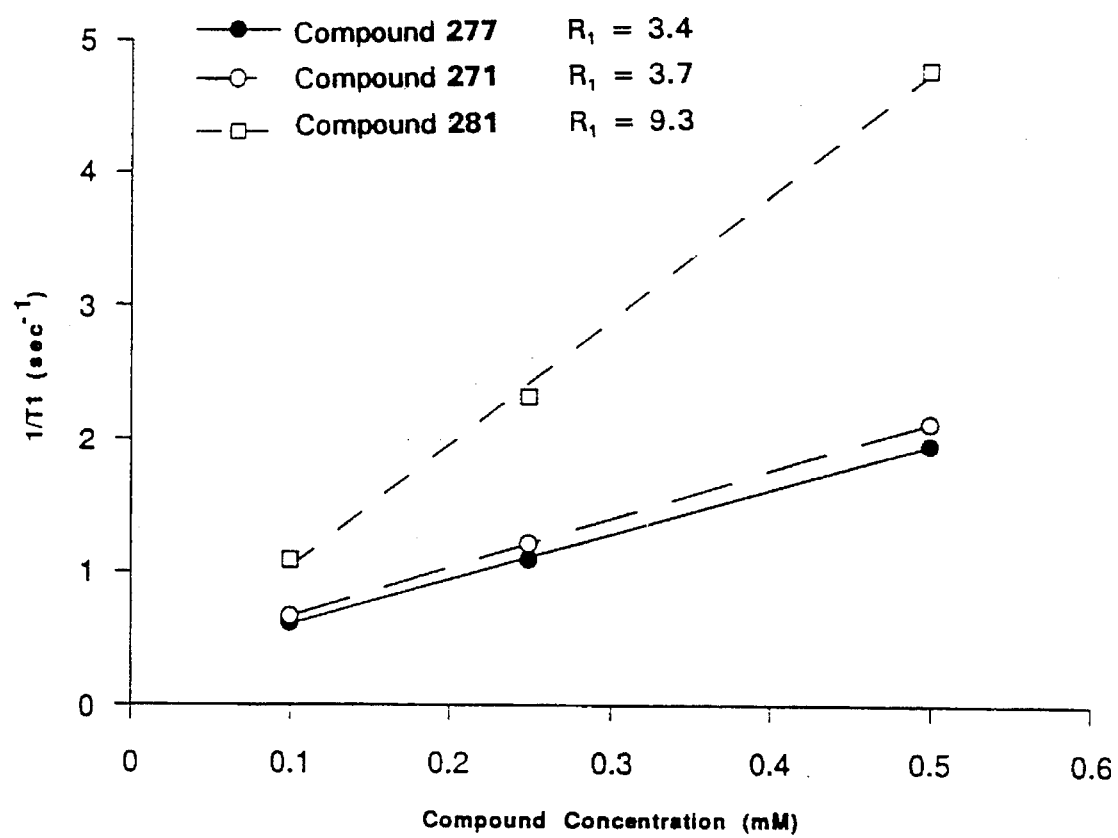
FIG. 1 is a plot of relaxivity "$R_1$" data in water associated with an amplifier according to the present invention, compound 281, compared with two monochelator compounds (compounds 271 and 277), as discussed in Examples 59–63.

As used herein, an "amplifier" or "amplifier molecule" is a chemical compound comprising a "core group" to which is attached at least one branching arm (i.e., "dendritic structure") terminating with plural "active groups."

The term "amplification factor" refers to the number of active groups present on an amplifier molecule according to the present invention. For example, a molecule having an amplification factor of four has a total of four active groups.

A first class of amplifiers according to the present invention consists of dendritic derivatives ("dendrimers") of 3,5-bis-(aminomethyl)benzene (compound 1A):

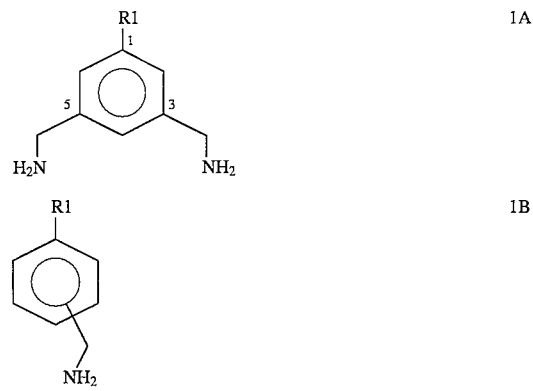

Thus, compound 1A represents a first "core group" in compounds according to the present invention, wherein the two aminomethyl arms are preferably at the 3- and 5-positions.

As used herein, a "core group" is the portion of an amplifier to which the group represented by R1 as well as the dendritic structure(s) of the amplifier are attached.

Attached to each of the two aminomethyl arms on compound 1A is a dendritic structure having plural termini, as exemplified at length below. At least one "active group," as defined below, is covalently attached to each terminus.

Another class of compounds according to the present invention consists of dendritic derivatives of aminomethyl benzene (compound 1B, shown above). In compound 1B, the single aminomethyl arm is preferably para to R1, but can also be ortho or meta. Compound 1B, which represents a second "core group" in compounds according to the present invention, is similar to compound 1A except that compound 1B has only one aminomethyl arm. In amplifiers derived from compound 1B, a dendritic structure is attached to the aminomethyl arm. The dendritic structure has plural termini to each of which termini at least one active group is covalently attached.

In many instances, each dendritic structure attached to a core group is bilaterally symmetrical with itself; but, such symmetry is not required. Also, in amplifiers having more than one dendritic structure, the dendritic structures are typically symmetrical relative to each other; but, again, such symmetry is not required.

Each "active group" on a terminus of a dendritic structure of an amplifier according to the present invention is a chemical moiety directly responsible for the desired diagnostic or chemotherapeutic effect of the amplifier. For magnetic resonance imaging purposes, for example, each active group is selected from a group consisting of nitroxides and paramagnetic metal-ion chelators.

The instant disclosure exemplifies various ways in which, and discloses various synthesis schemes by which, nitroxides and paramagnetic metal-ion chelators can be attached to the termini of dendritic structures of amplifiers. However, the synthesis chemistry disclosed herein is not limited to nitroxides and paramagnetic metal-ion chelators. i.e., other active groups besides nitroxides and paramagnetic metal-ion chelators (such as any of various pharmacological or diagnostic groups) can be attached to the termini using the same attachment chemistry; there is nothing about the structures of nitroxides and chelators that would limit the attachment chemistry disclosed herein only to attaching these moieties.

By thus attaching multiple active groups to a single core group, a substantially enhanced effect can be obtained per mole of amplifier molecules according to the present invention than obtainable per mole of conventional diagnostic or therapeutic agents having only one active group per molecule. In addition, a given number of amplifier molecules according to the present invention can exhibit their desired effect for a longer time than the same number of molecules of conventional agents.

In general, active groups are attached to the termini of the dendritic structures by linkages derived from chemistry involving amino groups or groups that are derivatives of amino groups such as isocyanate or isothiocyanate groups. Thus, such amino-derived linkages include, but are not limited to:—NH—C(O)—, —NH—C(S)—, —NH—C(O)—NH—, and —NH—C(S)—NH— linkages. Other possible linkages, not intended to be limiting, include —O—C(O)—, —O—, and —C(O)— linkages.

"Nitroxides" (sometimes referred to in the art as "stable nitroxides") are well known in the MRI art. A number of representative nitroxides are exemplified in Keana, "Synthesis and Chemistry of Nitroxide Spin Labels," in *Spin Labeling in Pharmacology*, Academic Press, N.Y. (1984), incorporated herein by reference. See also, J. F. W. Keana, U.S. Pat. No. 4,099,918, and Keana et al., "Nitroxides as Potential Contrast Enhancing Agents for MRI Application: Influence of Structure on the Rate of Reduction by Rat Hepatocytes, Whole Liver Homogenate, Subcellular Fractions, and Ascorbate," *Magnetic Resonance in Medicine* 5:525–536 (1987), also incorporated herein by reference.

Examples of certain paramagnetic metal-ion chelators can be found in J. F. W. Keana, U.S. Pat. Nos. 5,135,737 and 5,252,317, both incorporated herein by reference. Other references disclosing suitable chelators include Lauffer, "Paramagnetic Metal Complexes as Water Proton Relaxation Agents for NMR Imaging: Theory and Design," *Chem. Rev.* 87:901–927 (1987); and Rocklage et al., "Chelates of Gadolinium and Dysprosium as Contrast Agents for MR Imaging," *J Mag. Reson, Imaging* 3:167–178 (1993), all incorporated herein by reference.

As used herein, a "paramagnetic metal ion" is selected from a group consisting of Gd(III), Mn(II), Mn(III), Fe(III), Cr(III), Cu(II), Co(II), Ni(II), Dy(III), Tb(III), Ho(III), Er(III), Eu(III), and Nd(III). (Most preferred paramagnetic metal ions are Gd(III), Fe(III), and Mn(II).) Various derivatives of DTPA (diethylenetriaminetetraacetic acid), including those disclosed herein, are preferred chelators for such ions in compounds according to the present invention. However, it will be understood that other chelators for these ions are also comprehended by the present invention because such other chelators can be readily incorporated into molecules according to the present invention using the same chemistry (as disclosed herein) as used to incorporate DTPA derivatives. Such alternative chelators include, but are not limited to, porphyrins; cryptate compounds; bis-, tris-, and tetracatechol compounds; ethylene-bis(2-hydroxyphenylglycine) and its derivatives, various aryl-DTPA derivatives, bis-2-(hydroxybenzyl)-ethylenediamine diacetic acid and its derivatives, and macrocyclic chelating ligands such as any of various DOTA-based chelators.

As can be seen in the structures of compounds 1A and 1B, the core group comprises a benzene ring possessing at least one aminomethyl group. According to the present invention, at least one dendritic structure that begins (at the nitrogen of the aminomethyl group) with either a "linker" or a "branch group" is attached to the nitrogen of each aminomethyl group. Beginning at the aminomethyl group, representing an "upstream" location, the dendritic structure becomes increasingly branched as it progresses in a "downstream" direction toward the termini of the dendritic structure.

As used herein, a "linker" is a chemical group that can be used in a dendritic structure to connect branch groups together, a branch group to the aminomethyl nitrogen of the core group, and/or active groups to a branch group. In contrast to branch groups, linkers do not change the amplification factor of the amplifiers.

A "branch group," as used herein, is a chemical group that ultimately allows attachment of multiple active groups to a single connection point on the core group or on the dendritic structure. A branch group provides a two-way or, alternatively, a three-way fork to a dendritic structure, each branch group thereby effectively multiplying the amplification factor downstream of the branch group by two or three, respectively. i.e., a branch group can be represented as being either "Y"-shaped (increasing the amplification factor by two) or "ψ"-shaped (increasing the amplification factor by three), wherein the stem of the "Y" or "ψ" is covalently attached to the terminus of an upstream linker or to a branch terminus of an upstream branch group. Thus, each aminomethyl-group nitrogen on the core group can have attached thereto either one or two linkers, or a branch group, on the corresponding aminomethyl nitrogen. A number of various linkers and branch groups can be used, which are described in detail below.

The downstream branch termini of each branch group (i.e., the ends of the arms of the "Y" or "ψ") can terminate with an active group, a linker, or another branch group, depending upon the particular amplifier.

In compounds 1A and 1B, the group designated "R1" (situated at the 1-position on the benzene ring) can also be a dendritic structure similar to the dendritic structures attached to the aminomethyl nitrogens. Preferably, however, R1 is any of various moieties useful for attaching (by either covalent or non-covalent bonding, depending upon the intended use of the amplifier) the core group to a "targeting group" such as a biological molecule or a group that binds specifically to a particular biomolecule. R1 can also include the targeting group. As used herein, a "targeting group" is a reactive or passive functional group that permits a selective covalent or non-covalent, respectively, attachment of the amplifier molecule to a desired situs on another molecule or structure, such as a preferred site on a biomolecule or biological structure such as a tumor or an organ. (Representative targeting groups, not intended to be limiting, are listed in Table I below, under the R''' column.)

R1 can have a general structure designated by —(R')$_{0-1}$—(R'')$_{0-1}$—R''(—R''')$_{0-1}$ as in Table I (wherein X is a monovalent metal cation):

TABLE I

| | —(R')$_{0-1}$—(R)$_{0-1}$—R"(—R''')$_{0-1}$ | | |
|---|---|---|---|
| R' | R | R" | R''' (examples) |
| C(O)—NH | aryl | H | polypeptide |
| C(S)—NH | aryl-(C$_1$-C$_{20}$ alkyl) | C$_1$-C$_6$ alkyl | antibody |
| C(O) | (C$_1$-C$_{20}$ alkyl)-aryl | C(O)—OH | nucleic acid |
| O | cycloalkyl | C(O)—O—(C$_1$-C$_6$ alkyl) | carbohydrate |
| NH—C(O) | C$_1$-C$_{20}$ alkyl | C(O)—O$^-$X$^+$ | fatty acid |
| NH—C(S) | | NH$_2$ | surfactant |
| NH—C(S)—NH | | NO$_2$ | diglyceride |
| NH—C(O)—NH | | NCS | triglyceride |
| C(O)—O | | NCO | steroid |
| O—C(O) | | OH | porphyrin |
| | | SH | enzyme inhibitor |
| | | B(OH)$_2$ | |
| | | R' | |

Thus, R1 can be structured to facilitate any of various important uses for amplifiers according to the present invention. For example, an R1 terminating with (i.e., in which R" is) an isothiocyanate (—N=C=S) group renders the amplifier particularly suitable for covalent attachment to an amino group on a biomolecule. The side chain of the amino acid lysine present in many peptides and polypeptides terminates with —NH$_2$; thus, an R1 terminating with an —N=C=S group can be readily attached to such a polypeptide via chemistry as disclosed herein or by chemistry known in the bioconjugate art. Since many antibodies (which are polypeptides) include lysines, an amplifier according to the present invention can be readily attached to a monoclonal antibody (as a representative targeting group shown in Table I under the R" heading) and thus be given a "targeting" capability (i.e., rendered capable of being taken up by, retained by, or bound to a particular situs in the body to a substantially greater degree than to other sites in the body). With monoclonal antibodies, the corresponding target situs will depend upon the particular immunospecificity of the monoclonal antibody.

R1 can also be structured to render an amplifier according to the present invention particularly capable of being attached to nucleic acids, carbohydrates, and fatty substances. For example, an R1 terminating with a boronic acid group (i.e., R" in Table I is a B(OH)$_2$ group) enables the amplifier to bind selectively to vicinal diol groups on carbohydrates or on carbohydrate portions of certain proteins or cells. As another example, as indicated in Table I, R1 can include a fatty acid (as a representative R''' group) or other substantially hydrophobic targeting group, rendering the amplifier to which R1 is attached particularly capable of attaching to peptides, polypeptides, and other biomolecules having substantial hydrophobic domains (such as the serum albumins. Such binding of amplifiers according to the present invention to serum albumins facilitates MRI imaging of intravascular structures and vascular dynamics.) Other potential hydrophobic targets for such compounds according to the present invention include any of various membrane structures, both extracellular and intracellular. R1 can also be fashioned to have a net charge, thereby facilitating electrostatic attachment of the compound to biomolecules and biological structures having a net opposite charge. Furthermore, the structure of R1 can be fashioned using, for example, any of various new computerized "molecular modeling" programs so as to enable the R1 group to stereochemically interact with a specific receptor or enzyme.

Certain key reactions can be exploited as required to form various amplifiers according to the present invention. A first reaction involves reaction of an isothiocyanate group with a primary amine to form thiourea linkage:

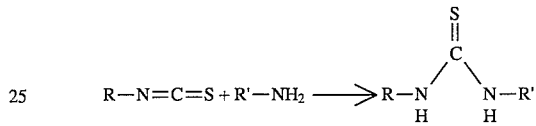

Thus, for example, providing an active group, a linker, or a branch group with a terminal isothiocyanate group allows the active group, linker, or branch group to be readily covalently attached to a primary amine present on a core group or on another linker or branch group. Also, providing a terminal isothiocyanate group on the 1-position or on any group attached to the 1-position of the core group allows the amplifier to be covalently attached to any of various target molecules, particularly any of a large number of various biomolecules, possessing a primary amine group (e.g., any of various polypeptides comprising a lysine. Such polypeptides would include antibody molecules). It will be appreciated that the chemistry of forming a thiourea linkage, as described above, is the same no matter what active group, linker, branch group, or target molecule is involved.

A second key reaction involves the formation of a terminal isothiocyanate group by reacting a corresponding amine group (—N$_2$) with thiophosgene (thiocarbonyl chloride; S=CCl$_2$) in chloroform/triethylamine:

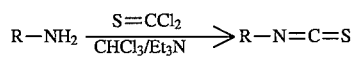

wherein R can be an active group, linker, or a branch group destined to be incorporated into an amplifier according to the present invention. R can also represent the core group wherein the amine is attached at the 1-position and conversion of the amine to the corresponding isothiocyanate renders the amplifier readily capable of being covalently attached to another molecule such as a biomolecule.

A third key reaction involves the conversion of a nitro (—NO$_2$) group to a corresponding primary amine (—NH$_2$) by reaction with stannous chloride; or with hydrogen in the presence of a Pd/C or other suitable catalyst:

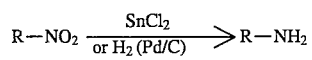

wherein R can be an active group, linker, or a branch group destined to be incorporated into an amplifier according to the present invention. R can also be a molecule destined to be the core group, wherein the nitro group on the molecule is converted to a corresponding amine to facilitate downstream reactions by which active groups, linkers, or branch groups are attached to the core group or by which the core group is rendered more able to be covalently linked to, e.g., a biomolecule.

A fourth key reaction involves the formation of an amide linkage by reacting a terminal amine with a carbonyldiimidazole-activated (CDI-activated) carboxylic acid:

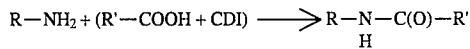

wherein R can be an active group, linker, or a branch group, or can represent the core group, as discussed above.

A fifth key reaction involves the reactions of a brominated alkyl, aryl, or alkylaryl molecule with a secondary amine to covalently link the secondary amine to the alkyl, aryl, or alkylaryl molecule:

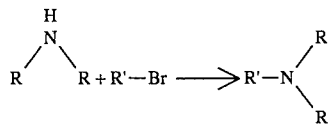

In the foregoing reaction, R can be an active group, a linker, or a branch group and R' can be any of the foregoing as well as a core group.

A sixth reaction that can be employed to synthesize any of various amplifiers according to the present invention is the familiar reaction of an amine with an isocyanate to form a urea linkage:

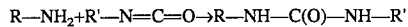

The amine in the foregoing reaction can be primary or secondary. R and R' can be an active group, linker, branch group, or core group.

Two other reactions that can be exploited are represented by the following examples involving activated esters:

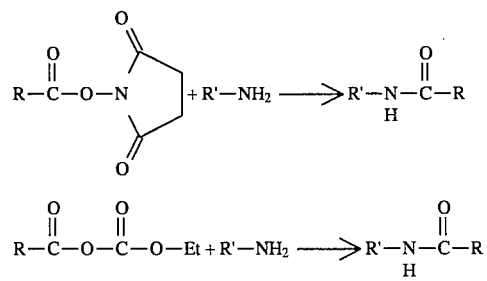

Other reactions can also be used, as illustrated in the various Examples.

With the foregoing basic principles in mind, it will be appreciated that linkers, branch groups, and active groups can be attached to core groups in various combinations, resulting in any of various species of compounds having any of various amplification factors. The variety of compounds that can be formed in this way can range from slightly branched (i.e., slightly dendritic) to heavily branched (i.e., heavily dendritic).

From a synthesis perspective, amplifiers according to the present invention are preferably prepared by either of two alternative strategies. The first strategy, termed an "active fragment-upgrade strategy," begins with attaching active groups to a dendritic structure or portion thereof not yet attached to a core group. The resulting dendritic structure containing active groups are then attached to the core group. The second strategy, termed a "core-upgrade strategy," begins with attachment of the dendritic structure(s) to the core group, followed by attachment of the active groups to the termini of the dendritic structure(s). In either of the foregoing strategies, any of the entities (core, linker, branch group, or active group) participating in the reactions can be used in a "protected" or masked form to facilitate linkage of these entities together in the desired dendritic configuration. For example, and not intended to be limiting, representative "activated" forms of a carboxy group include active esters such as N-hydroxysuccinimide esters, carbonyldiimidazole (CDI) derivatives of esters, or mixed anhydrides. Primary amino groups can be activated by conversion to isothiocyanates. Secondary amines can be activated by conversion to carbamoyl chlorides. Hydroxy groups can be activated by conversion to chloroformates.

Representative linkers include, but are not limited to, the following:

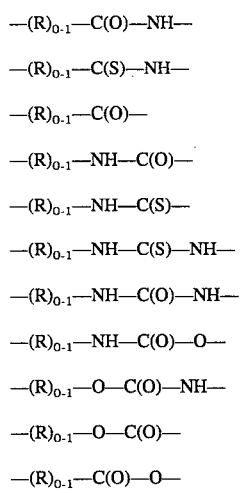

wherein R is an aryl, cycloalkyl, $C_1$–$C_{12}$ alkyl, aryl-($C_1$–$C_{12}$ alkyl), or ($C_1$–$C_{12}$ alkyl)-aryl group, or any combination of these groups, covalently linked together. The subscript "0-1" means that the corresponding group is either absent (0) or present (1).

The linkers can be either in the orientation shown above or in the corresponding reverse orientation.

Representative branch groups that double the amplification factor (i.e., that serve as "Y" branches) include, but are not necessarily limited to, the following:

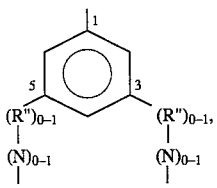

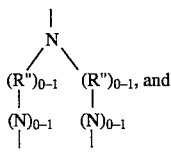

-continued

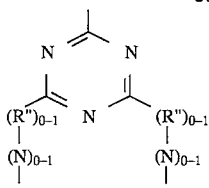

wherein R" is a $C_1$–$C_6$ alkyl.

Examples, not intended to be limiting, of branch groups that triple the amplification factor (i.e., that serve as "ψ" branches) include:

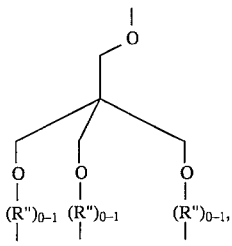

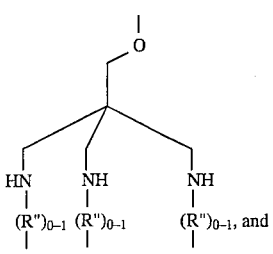

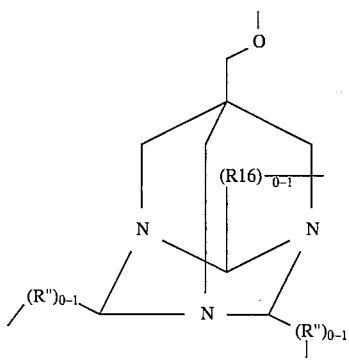

wherein R" is a $C_1$–$C_6$ alkyl.

Use of any amplifier according to the present invention in a living subject imposes several requirements. First, the amplifier should be sufficiently soluble in a physiologically compatible (usually aqueous) medium for in vivo administration. Satisfaction of this criterion is readily determined by performing a simple dissolution experiment. A related requirement is that a solution of the amplifier should not be so viscous that it cannot be made into a physiologically compatible medium. The amplifier must also be capable of exhibiting a desired level of effect (such as, in the case of MRI contrast-enhancing agents, the desired degree of contrast enhancement). With MRI-contrast amplifiers, satisfaction of this requirement is readily ascertained by dissolving the amplifier in a physiologically compatible aqueous medium such as isotonic saline or physiological buffer, which may contain serum albumin and other serum constituents, then ascertaining the relaxivity of the dissolved compound using an NMR instrument and conventional methods. Finally, the amplifier must have an acceptably low toxicity level at a dosage appropriate for achieving the desired effect.

Amplifier compounds according to the present invention useful for MRI contrast enhancement have several key advantages over conventional MRI contrast agents. First, as a result of their "amplifier" characteristic, it is possible to administer fewer amplifier molecules in order to achieve a desired degree of contrast enhancement, compared to conventional MRI contrast-enhancement agents. Another advantage is that, owing to their larger molecular weight, MRI contrast-enchancing amplifiers according to the present invention have slower and thus more favorable tumbling rates in solution than the tumbling rates of conventional MRI enhancing agents having only one active group. Furthermore, since the toxicity of MRI contrast-enhancement agents is a function of their inherent toxicity (i.e., toxicity of the entire molecule), administration of fewer molecules can result in lower overall toxicity than with conventional agents. With respect to amplifiers containing multiple paramagnetic metal-ion chelators, toxicity is also a function of the degree to which the complexed paramagnetic metal ion dissociates from the chelator, wherein the greater the ease of dissociation, the greater the toxicity. In any event, toxicity is readily ascertainable by simple experiments involving dosing cells in culture and/or animal subjects with known amounts of the test compound.

For use in vivo, amplifiers according to the present invention are dissolved in a physiologically compatible aqueous medium and administered to the subject either orally, intravenously, or other effective route, depending upon the region of the body to be studied and the anticipated physiological effect of the amplifier. Dosage will depend upon a number of factors including, but not limited to, (a) whether or not the amplifier is "targeting" such as by being linked to an antibody; (b) in the case of the amplifiers being used diagnostically, the sensitivity of the diagnostic instrumentation to be used with the amplifier; (c) the number of active groups on the amplifier; (d) the particular type of active groups on the amplifier; (e) in the case in which the active groups are paramagnetic metal-ion chelators, the particular metal ion held by the chelators (e.g., Gd(III) is more highly paramagnetic than Fe(III); thus, Gd(III) chelators would generally require a lower dose); and, for an amplifier that is a blood-pool agent, whether or not the amplifier remains in the blood pool rather than becoming evenly distributed throughout the aqueous compartments of the body.

After administering an amplifier according to the present invention that is an MRI contrast-enhancement agent, conventional NMR imaging of the subject is conducted. Operational parameters of the imaging instrument, such as pulse-sequence parameters and imaging parameters, will depend upon the type of diagnostic information being sought. Setting of these parameters is within the skill of MRI technicians.

In order to further illustrate the invention, the following examples are provided.

The following abbreviations are used in the Examples:
$^{13}$C NMR: carbon-13 nuclear magnetic resonance
$^{1}$H NMR: proton nuclear magnetic resonance
calcd: calculated
$CDCl_3$: deuterated chloroform
CEP: carboxyethyl phthalimide
$D_2O$: "heavy" water DCC: dicyclohexylcarbodiimide
DCU: dicyclohexylurea
dec.: decomposed
DETA: diethylenetriamine
DMF: dimethylformamide
DMSO: dimethylsulfoxide
EPR: electron paramagnetic resonance
$Et_3N$: triethylamine
EtOAc: ethylacetate
FAB MS: fast atom bombardment mass spectrometry
HOSA: hydroxylamine-O-sulfonic acid
HPLC: high-performance liquid chromatography
HR FAB MS: high-resolution fast atom bombardment mass spectrometry
HRMS: high-resolution mass spectrometry
HSA: human serum albumin
IR: infrared
MeCN: acetonitrile
MeOD: deuterated methanol
MeOH: methanol
mp: melting point
NBS or N-BS: N-bromosuccinimide
NHS or N-HS: N-hydroxysuccinimide
NMR: nuclear magnetic resonance
$PhNDND_2$: deuterated phenylhydrazine
$PhNHNH_2$: phenylhydrazine
$t-BuNH_2$: tert-butylamine
TFA: trifluoroacetic acid
THF: tetrahydrofuran
TLC: thin-layer chromatography The meanings of other abbreviations and chemical formulae used herein will be apparent to persons of ordinary skill in the relevant art.

In the following Examples, the following general methods were employed:

Melting points were obtained in a Thomas-Hoover apparatus; melting-point data presented below are uncorrected.

Infrared spectra of subject compounds were obtained in KBr pellets (concentration 0.2 to 0.5 percent), or in $CCl_4$ or $CHCl_3$ solutions (concentration 2 to 5 percent), on a Nicolet 5DX or a Nicolet Magna-IR 550 IR FT spectrometer.

$^1H$ (300 MHz) and $^{13}C$ (75 MHz) NMR spectra were obtained using a General Electric QE-300 FT instrument. Chemical shifts are reported in $\delta$ units referenced to the residual proton signal in deuterated solvents.

NMR spectra of nitroxide free radicals were obtained using in situ reduction with phenylhydrazine. In order to remove signals of the reductant in the region of the aliphatic protons (1–6 ppm), $PhNDND_2$, prepared by evaporation (3 times) of a solution of freshly distilled $PhNHNH_2$ in MeOD, was used.

First-derivative EPR spectra were recorded on a Bruker ESP-300 spectrometer (at $10^{-5}$ to $10^{-4}$M concentrations). Solutions were de-oxygenated by passing nitrogen through the solution for 1 to 2 min prior to obtaining measurements. The reported values are the number of lines observed, the relative linear intensities, and the hyperfine splitting constants on nitrogen, $a_N$, expressed in gauss (G).

The identities of similar compounds prepared by different methods was established by comparison of their IR spectra, $^1H$ NMR spectra and $R_f$ TLC or $R_t$ HPLC values using the criterion of coelution.

Analytical TLC was performed using Merck plastic-backed silica gel 60 $F_{254}$ plates. Preparative TLC was done on Analtech Uniplate precoated silica gel glass-backed plates (20×20 cm×1 mm), and on plates that were self-made using Merck silica gel 60 $PF_{254}$ (40 cm×30 cm×3 mm).

Analytical HPLC was performed using a Waters Resolve $C_{18}$ 0.8×10 cm Radial-PAK cartridge and Rainin Microsorb-MV $C_{18}$ 0.46×25 cm column. The eluent for gradient A: ($H_2O$+0.2% TFA), and for gradient B: (MeCN with 0.2% TFA) with UV-detection at 230 or 254 nm. The reported values are retention times and peak areas in relative percent.

Preparative column chromatography was performed using Baker silica gel (60–200 mesh); flash-chromatography was performed using Aldrich silica gel, Davisil, grade 643 (200–425 mesh). Size exclusion chromatography was performed using a Pharmacia-LKB Gradifrac system using Sephadex G-10 and Sephadex G-25 Fine gels (bed 2.5 cm×80 cm).

Reagents, unless otherwise noted, were purchased from Aldrich Chemical Co. and were used without additional purification. Solvents, drying and auxiliarly reagents were purchased from Baker. THF and ether were distilled over benzophenone ketyl prior to use. All reactions were performed under a nitrogen atmosphere.

EXAMPLES 1–3

In these examples, illustrated in Scheme 1, we attached a pyrroline nitroxide radical moiety to an aminomethyl benzene moiety to produce compound 203 using two different acylation procedures. The methyl protection was subsequently removed from the carboxyl group by basic hydrolysis.

Scheme 1

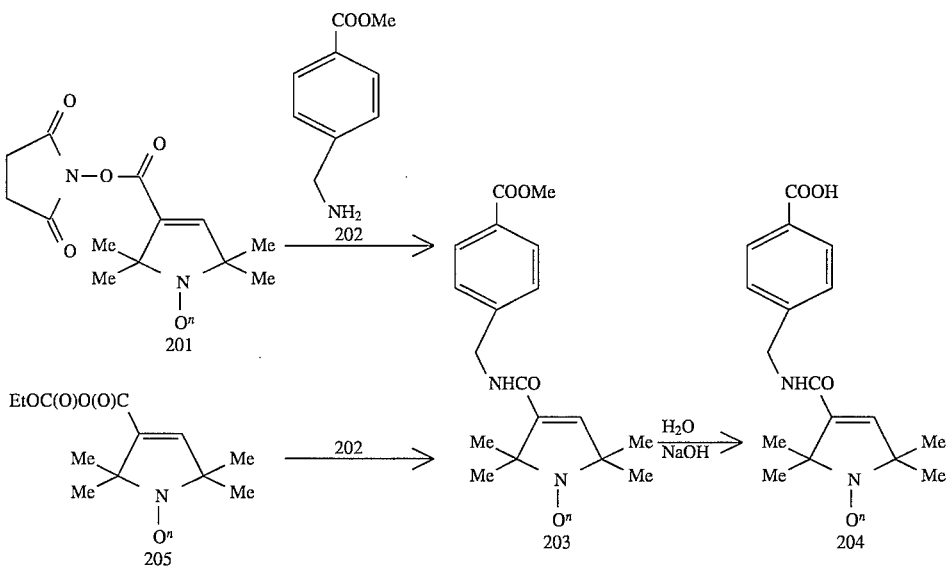

In Scheme 1, the methyl 4-aminomethyl benzoate compound (202) served as a useful example of a core group. Compound 202 has only one terminal amine; however, the chemistry (as described below) of attaching a nitroxide to the terminal amine is not limited to core groups having only one terminal amine. Rather, the chemistry is equally applicable to other core groups having any number of terminal amines. Likewise, the chemistry is equally applicable to attaching nitroxides and other active groups to linkers or branch groups having at least one terminal amine.

Example 1 pertained to an acylation using the NHS ester 201, and was performed as follows: To a mixture of NHS ester 201 (1.827 g, 6.5 mmol) and methyl 4-aminomethyl benzoate (202) (hydrochloride, 1.063 g, 5 mmol) in DMF (30 mL), Et$_3$N (0.84 mL, 6 mmol) was added dropwise. The mixture was stirred for 70 h, then evaporated to dryness. The residue was suspended in EtOAc (150 mL); and sequentially washed with H$_2$O (50 mL), 2N HCl (3×20 mL), H$_2$O (20 mL), saturated NaHCO$_3$ (3×20 mL), then H$_2$O (20 mL). The product was dried (MgSO$_4$), then evaporated. The residue was flash-chromatographed on a silica gel column (1.5×25 cm, with CHCl$_3$ eluant) to yield methyl 4-(2',2',5',5'-tetramethyl-1'-oxyl-3'-pyrroline-4'-carbonyl)-aminomethyl benzoate, compound 203 (1.609 g, 97% yield) as a yellow solid. Relevant data: mp 93°–94° C. (from EtOAc:hexane, 1:1); IR (KBr) 1721, 1672, 1619 and 1515 cm$^{-1}$; $^1$H NMR (CDCl$_3$+ PhNDND$_2$) δ1.28 (s, 6H), 1.44 (s, 6H), 3.92 (s, 3H), 4.55 (s, 2H), 6.06 (s, 1H), 7.36 (d, 2H, J=8 Hz), 8.02 (d, 2H, J=8 Hz). Anal. calcd for C$_{18}$H$_{23}$N$_3$O$_4$: C, 65.24; H, 7.00; N, 8.45; found: C, 65.51; H, 6.86; N, 8.63.

Example 2 pertained to an alternative acylation reaction using the mixed anhydride 205, and was performed as follows: To a stirred suspension of amine 202 (hydrochloride, 2.50 g, 11.8 mmol) and mixed anhydride 205 (3.00 g, 11.7 mmol) in DMF (25 mL), Et$_3$N was added dropwise. The mixture was stirred for 16 h, then evaporated to dryness. The residue was suspended in EtOAc (250 mL); washed sequentially with H$_2$O (50 mL), 2N HCl (3×30 mL), H$_2$O (30 mL), saturated NaHCO$_3$ (3×30 mL), and H$_2$O (50 mL); dried (MgSO$_4$); then evaporated. The residue was chromatographed on a silica gel (4×40 cm, CHCl$_3$ eluant), which yielded compound 203 (1.810 g, 47% yield).

Example 3 pertained to hydrolysis of methoxycarbonyl groups, and was performed as follows: A mixture of the methyl ester 203 (1.600 g, 4.83 mmol) in MeOH (30 mL) and 1N NaOH (10 mL) was stirred for 2 h, then diluted with H$_2$O (50 mL). The mixture was extracted with CHCl$_3$ (20 mL, discarded), acidified (2N HCl) to pH 1, then extracted with CHCl$_3$ (10×15 mL). The extract was dried (MgSO$_4$) and then evaporated to yield (2',2',5',5'-tetramethyl-1'-oxyl-3'-pyrroline- 4'-carbonyl)-aminomethyl benzoic acid, compound 204 (1.317 g, 70% yield) as an orange solid. Relevant data: mp 177°–178° C. (from EtOAc); IR (KBr) 1688, 1678, 1627, 1612, 1530 and 1511 cm$^{-1}$. Anal. calcd for C$_{17}$H$_{21}$N$_2$O$_4$: C, 64.34; H, 6.67; N, 8.83; found: C, 64.39; H, 6.61; N, 8.74.

EXAMPLES 4–5

These examples, illustrated in Scheme 2, are similar to Examples 1–3 except that an imidazoline nitroxide, rather than a pyrroline nitroxide, was attached to an aminomethyl benzene core group, thereby producing compound 207. NHS activation of the carboxyl group of nitroxide 206 was used, followed by removal of the methyl protection from the carboxyl group by basic hydrolysis. As with Examples 1–3, the reactions shown in Scheme 2 are also applicable to attaching active groups to other core groups having any number of terminal amines and to attaching active groups to any of various linkers or branch groups having at least one terminal amine.

Scheme 2

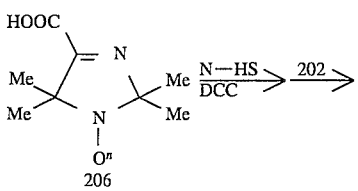

21
-continued
Scheme 2

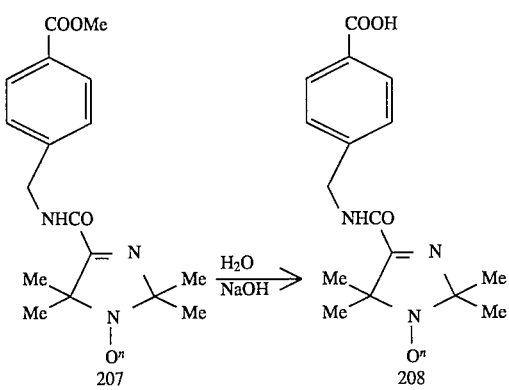

22
EXAMPLES 6–8

In these Examples, illustrated in Scheme 3, the previously unknown spiro-substituted imidazoline nitroxide radical 215 was synthesized and attached to an aminomethyl benzene moiety to produce compound 216. NHS activation of the carboxyl group of nitroxide 215 was employed, followed by removal of the methyl protection from the carboxyl group by basic hydrolysis. As with the foregoing Examples, the reactions shown in Scheme 3 are also applicable to attaching active groups to other core groups having any number of terminal amines and to attaching active groups to any of various linkers or branch groups having at least one terminal amine.

Example 4 was performed as follows: To a stirred mixture of the acid 206 (0.685 g, 3.7 mmol) and NHS (0.436 g, 3.7 mmol) in EtOAc (50 mL) a solution of DCC (0.762 g, 3.7 mmol) in EtOAc (10 mL) was added dropwise at 0° C. The mixture was allowed to warm to room temperature and stirred for 3 h, then amine 202 (hydrochloride, 0.850 g, 4 mmol) was introduced, followed by dropwise addition of $Et_3N$ (0.58 mL, 4 mmol). The reaction mixture was stirred for 16 h, then filtered to remove the DCU by-product. The precipitate was washed with EtOAc (5×10 mL). The combined filtrates were then evaporated to dryness and the residue was flash-chromatographed on a silica gel column (1.5×25 cm, eluant: 3% MeOH in $CHCl_3$) to yield methyl 4-(2',2',5',5'-tetramethyl-1'-oxyl-3'-imidazoline- 4'-carbonyl)aminomethyl benzoate, compound 207 (0.493 g, 41% yield) as a yellow solid. Relevant data: mp 147°–148° C. (from EtOAc); IR (KBr) 1721, 1678, 1619 and 1515 $cm^{-1}$; $^1H$ NMR ($CDCl_3$+$PhNDND_2$) $\delta$1.40 (s, 3H), 1.47 (s, 3H), 3.91 (s, 3H), 4.54 (d, 2H, J=6 Hz), 7.40 (d, 2H, J=9 Hz), 8.02 (d, 2H, J=9 Hz). Anal. calcd for $C_{17}H_{22}N_3O_4$: C, 61.43; H, 6.67; N, 12.64; found: C, 61.43; H, 6.51; N, 12.31.

In Example 5, a mixture of methyl ester 207 (0.480 g, 1.45 mmol) in MeOH (50 mL) and 1N NaOH (20 mL) was stirred for 2 h, then diluted with $H_2O$ (50 mL). The mixture was extracted with $CHCl_3$ (10 mL, discarded), acidified (2N HCl) to pH 1, then extracted with $CHCl_3$ (10×10 mL). The extract was dried ($MgSO_4$) and evaporated to yield 4-(2',2', 5',5'-tetramethyl-1-oxyl-3'-imidazoline-4'-carbonyl)aminomethyl benzoic acid, compound 208 (0.360 g, 78% yield) as an orange solid. Relevant data: mp 204°–206° C. (from EtOAc); IR (KBr) 1696, 1662, 1615, and 1538 $cm^{-1}$; Anal. calcd for $C_{16}H_{20}N_3O_4$: C, 60.37; H, 6.33; N, 13.20; found: C, 60.77; H, 6.39; N, 13.15.

Scheme 3

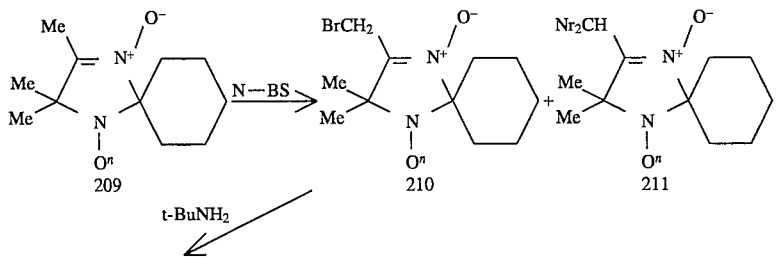

-continued
Scheme 3

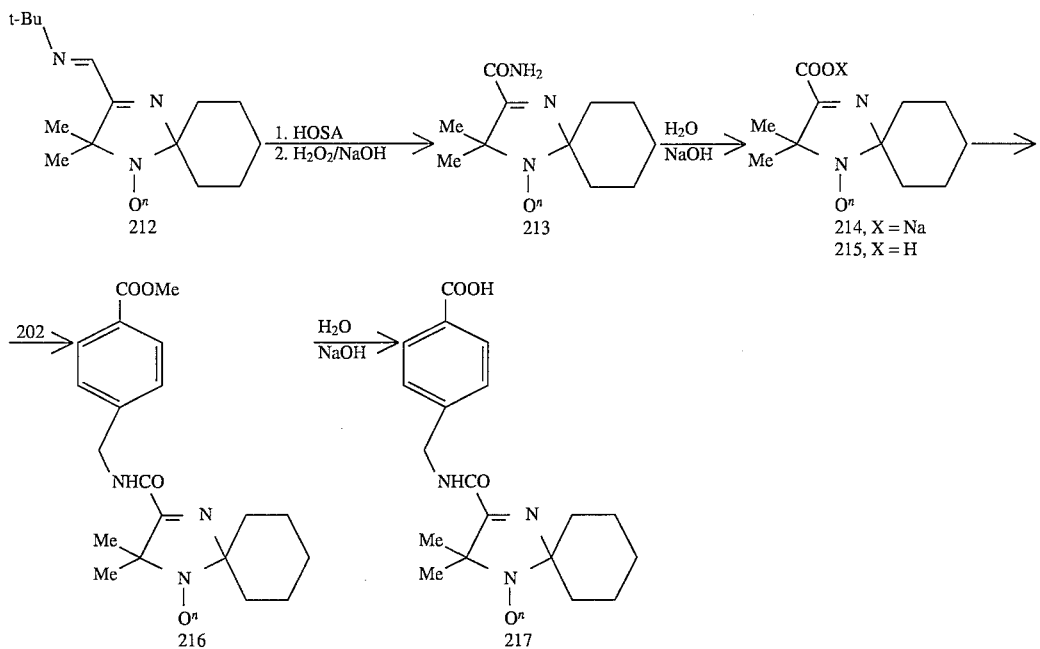

Example 6, pertaining to the synthesis of the nitroxide spiro compound 215, was performed as follows: To a stirred suspension of 4,5,5-trimethyl- 2-spirocyclohexane-3-imidazoline-3-oxide-1-oxyl (209) (7.37 g, 34.9 mmol) and NBS (6.23 g, 35 mmol) in $CCl_4$ (100 mL), TFA (1 mL) was added. The mixture was stirred for 4 h, the precipitated succinimide was removed by filtration, and the precipitate was washed with $CCl_4$ (3×10 mL). The combined filtrates were evaporated and the residue was chromatographed over silica gel (4×80 cm, $CHCl_3$ eluant). The desired compound, 4-bromomethyl-5,5-dimethyl-2-spirocyclohexane-3-imidazoline-3-oxide-1-oxyl, compound 210, (2.30 g, 23% yield) was eluted after the dibromination product, 4-dibromomethyl-5,5-dimethyl-2-spirocyclohexane-3-imidazoline-3-oxide-1-oxyl (211) (2.04 g, 16% yield). Relevant data for compound 210: TLC $R_f$=0.4 (5% MeOH in $CHCl_3$); mp 101°–103° C. (from EtOAc); IR (KBr) 3038, 2979, 1575, 1449 and 1186 $cm^{-1}$; $^1H$ NMR ($CDCl_3$+$PhNDND_2$) $\delta 1.47$ (s, 6H), 1.90 (br.m, 10H), 4.15 (s, 2H). HRMS calcd for $C_{11}H_{18}N_2O_2Br$: 289.0552; found: 289.0552. Relevant data for compound 211: TLC $R_f$=0.7 (5% MeOH in $CHCl_3$); mp 119°–121° C. (from EtOAc); IR (KBr) 2995, 2976, 1572, 1443, and 1167 $cm^{-1}$; $^1H$ NMR ($CDCl_3$+$PhNDND_2$) $\delta 1.65$ (s, 6H), 1.80 (br.m, 10H), 6.62 (s, 1H). HRMS calcd for $C_{11}H_{17}N_2O_2{}^{79}Br^{31}Br$: 369.0304; found: 368.9644.

Continuing with Example 6, to a stirred solution of $t$-$BuNH_2$ (5 mL, 48 mmol) in $H_2O$ (4 mL), compound 210 was introduced in small portions over 1.5 h. The mixture was stirred for an additional 1 h at 40° C. The precipitate was filtered and washed with $H_2O$ (3×10 mL) to produce 4-t-butyliminomethyl-5,5-dimethyl- 2-spirocyclohexane-3-imidazoline-1-oxyl (compound 212) (1.900 g, 99% yield) as an orange-yellow solid. Relevant data: mp 92°–95° C. (crude); IR (KBr) 2865, 2848, 1648, 1639, 1598, 1226 and 1212 $cm^{-1}$.

To a stirred suspension of the imine 212 (2.64 g, 10 mmol used without purification) in $H_2O$ (30 mL), hydroxylamine-O-sulfonic acid (HOSA) (1.360 g, 12 mmol) was added. After 10 min a 10-percent solution of $H_2O_2$ (20 mL) was added, followed by dropwise addition of 2N NaOH (10 mL). The mixture was stirred for 1 h to yield precipitated 4-aminocarbonyl-5,5-dimethyl- 2-spirocyclohexane-3-imidazoline-1-oxyl (compound 213). The precipitate was filtered and then washed with $H_2O$ (3×10 mL). The combined filtrates were extracted with $CHCl_3$ (5×10 mL). The extract was dried ($MgSO_4$) and evaporated to yield an additional quantity of the product 213 as an orange solid. The combined yield was 1.946 g (87% yield). Relevant data: mp 200°–203° C. (from EtOH); IR (KBr) 1720, 1678 and 1524 $cm^{-1}$; $^1H$ NMR ($CDCl_3$+$PhNDND_2$) $\delta 1.48$ (s, 6H), 1.70 (br.m, 10H). HRMS calcd for $C_{11}H_{18}N_3O_2$: 224.1399; found: 224.1410.

Continuing further with Example 6, a suspension of the amide 213 (1.800 g, 8.03 mmol) in 1N NaOH (8 mL) was stirred for 3 h at 90° C. (mixture became a clear solution) and then evaporated to dryness. Residual water was removed by evaporation with benzene (3×20 mL). Ether (50 mL) was added and the product was filtered, washed further with ether (3×10 mL), then dried in vacuo to produce the acid 214 (sodium salt), 1.615 g (81% yield). Relevant data: mp 180°–183° C. (dec.).

Compound 214 was used in the next Example without purification. The free acid, 4-carboxy- 5,5-dimethyl-2-spirocyclohexane-3-imidazoline-1-oxyl, compound 215, was prepared by extraction of a solution of compound 214 that was subsequently acidified (2N HCl) to pH 3. Compound 215 was unstable for storage and was immediately used in the next Example.

Example 7, pertaining to connection of the spiro compound 215 to an amine-containing compound, was performed as follows: To a stirred mixture of the acid 215 (0.800 g, 3.56 mmol) and NHS (0.818 g, 7.11 mmol) in DMF (50 mL), a solution of DCC (1.465 g, 7.11 mmol) in DMF (10 mL) was added dropwise at 0° C. The mixture was allowed to warm to room temperature and was stirred for 6 h. Then, amine 202 (hydrochloride, 1.511 g, 4 mmol) was introduced followed by dropwise addition of Et₃N (1.54 mL, 7.11 mmol). The reaction mixture was stirred for 16 h, then filtered to remove DCU. The DCU precipitate was washed with EtOAc (5×10 mL). The combined filtrates were evaporated to dryness and the residue was flash-chromatographed on a silica gel column (1.5×15 cm, eluant: 1% MeOH in CHCl₃) to produce methyl 4-(5',5'-tetramethyl-2'-spirocyclohexane-1-oxyl-3-imidazoline-4-carbonyl)aminomethyl benzoate, compound 216 (0.575 g, 43% yield), as a yellow solid. Relevant data: mp 146°–148° C. (from EtOAc); IR (KBr) 1721, 1672, 1619 and 1515 cm⁻¹; ¹H NMR (CDCl₃+PhNDND₂) δ1.48 (s, 3H), 1.65 (m, 10H), 3.92 (s, 3H), 4.56 (d, 2H, J=6 Hz), 7.38 (d, 2H, J=9 Hz), 8.03 (d, 2H, J=9 Hz). Anal. calcd for C₁₇H₂₂N₃O₄: C, 61.43; H, 6.67; N, 12.64; found: C, 61.43; H, 6.51; N, 12.31.

In Example 8, the methoxycarbonyl group of 216 was hydrolyzed as follows: A mixture of the methyl ester 216 (0.320 g, 0.86 mmol) in MeOH (10 mL) and 1N NaOH (7 mL) was stirred for 20 h, then diluted with H₂O (20 mL). The mixture was extracted with CHCl₃ (3×10 mL, discarded), acidified (2N HCl) to pH 2, then extracted with CHCl₃ (10×10 mL). The extract was dried (MgSO₄) and evaporated to yield 4-(5',5'-dimethyl-2-spirocyclohexane-1'-oxyl-3'-imidazoline- 4'-carbonyl)aminomethyl benzoic acid, compound 217 (0.262 g, 80% yield), as a yellow solid. Relevant data: mp 190°–191° C. (from EtOAc); IR (KBr) 1708, 1666, 1614, and 1534 cm⁻¹; ¹H NMR (CDCl₃+PhNDND₂) δ1.67 (s, 3H), 1.70 (m, 10H), 4.62 (d, 2H, J=6 Hz), 7.37 (d, 2H, J=8 Hz), 8.07 (d, 2H, J=8 Hz). Anal. calcd for C₁₉H₂₄N₃O₄: C, 63.67; H, 6.75; N, 11.72; found: C, 63.72; H, 6.70; N, 11.77.

EXAMPLES 9–10

In these examples, illustrated in Scheme 4, an imidazoline-N-oxide nitroxide radical moiety was attached to an aminomethyl benzene moiety to produce compound 219. NHS activation of the carboxyl group of the nitroxide 218 was employed, followed by removal of the methyl protection from the carboxyl group by basic hydrolysis. As with the foregoing Examples, the reactions shown in Scheme 4 are also applicable to attaching active groups to other core groups having any number of terminal amines and to attaching active groups to any of various linkers or branch groups having at least one terminal amine.

Scheme 4

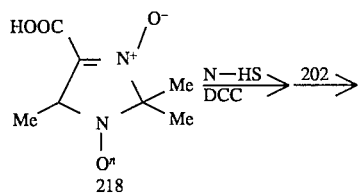

-continued
Scheme 4

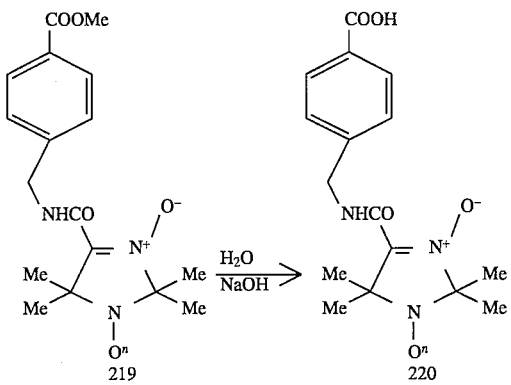

Example 9 was performed as follows: To a stirred mixture of the acid 218 (2.500 g, 12.4 mmol) and NHS (1.495 g, 13 mmol) in EtOAc (100 mL), a solution of DCC (2.678 g, 13 mmol) in EtOAc (20 mL) was added dropwise at 0° C. The mixture was allowed to warm to room temperature and stirred for 4 h, then amine 202 (hydrochloride, 4.250 g, 20 mmol) was added, followed by dropwise addition of Et₃N (4.3 mL, 30 mmol). The reaction mixture was stirred for 16 h, then filtered to remove DCU. The precipitate was washed with EtOAc (5×10 mL). The combined filtrates were sequentially washed with brine (20 mL), 2N HCl (3×10 mL), brine (10 mL), saturated NaHCO₃ (3×10 mL), and H₂O (10 mL). The filtrate was dried (MgSO₄), and evaporated to dryness. The residue was flash-chromatographed on a silica gel column (4×30 cm, eluant: 2% MeOH in CHCl₃) to yield compound methyl 4-(2',2',5',5'-tetramethyl- 1-oxyl-3-imidazoline-3-oxide-4-carbonyl)aminomethyl methyl benzoate (compound 219) (3.313 g, 77% yield), as a yellow solid. Relevant data: mp 84°–85° C. (from EtOAc:hexane 1:1); IR (KBr) 1723, 1670, 1615, 1557 and 1537 cm⁻¹. Anal. calcd for C₁₇H₂₂N₃O₅: C, 58.61; H, 6.37; N, 12.06; found: C, 58.47; H, 6.40; N, 12.28.

Example 10 was performed as follows: A mixture of the methyl ester 219 (2.200 g, 6.32 mmol) in MeOH (50 mL) and 1N NaOH (35 mL) was stirred for 2 h, then diluted with H₂O (50 mL). The mixture was extracted with CHCl₃ (10 mL, discarded), acidified (2N HCl) to pH 1, then extracted with CHCl₃ (10×10 mL). The extract was dried (MgSO₄) and evaporated. The residue was chromatographed over silica gel (4×35 cm, eluant: 3% MeOH in CHCl₃) to yield 4-(2',2',5',5'-tetramethyl-3'-imidazoline-3-oxide-1'-oxyl-4'-carbonyl)aminomethyl benzoic acid, compound 220 (1.896 g, 90% yield), as an orange solid. Relevant data: mp 163°–164° C. (from EtOH); IR (KBr) 1720, 1657, 1612, 1558 and 1541 cm⁻¹; ¹H NMR (CDCl₃+PhNDND₂) δ1.61 (s, 12H), 4.62 (d, 2H, J=6 Hz), 7.42 (d, 2H, J=8 Hz), 8.06 (d, 2H, J=8 Hz). Anal. calcd for C₁₆H₂₀N₃O₅: C, 57.48; H, 6.03; N, 12.57; found: C, 57.21; H, 6.08; N, 12.57.

EXAMPLES 11–13

In these examples, illustrated in Scheme 5, the novel bicyclic nitroxide radical 222 was synthesized and attached to an aminomethyl benzene moiety to produce compound 223. NHS activation of the carboxyl group of nitroxide 222 was employed, followed by removal of the methyl protection from the carboxyl group by basic hydrolysis. As with the foregoing Examples, the reactions shown in Scheme 5 are also applicable to attaching active groups to other core groups having any number of terminal amines and to attaching active groups to any of various linkers or branch groups having at least one terminal amine.

Scheme 5

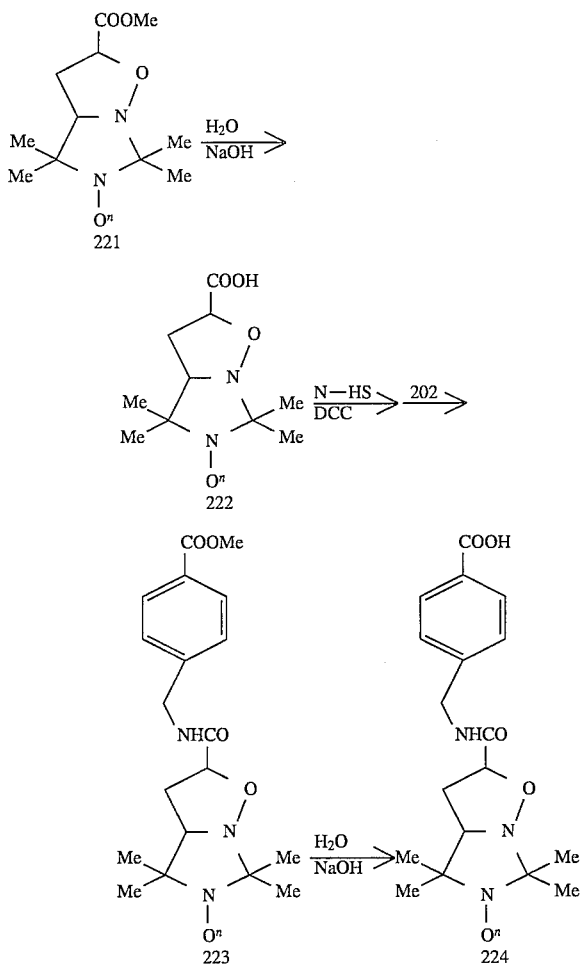

Example 11 pertained to the synthesis of the bicyclic nitroxide acid 222. A mixture of 4-methoxycarbonyl-4,4,6,6-tetramethyl-5-oxyl-2,3,4,6,7,8-hexahydro-5H-imidazo[1,5-b]-isoxazole, compound 221 (1.215 g, 5 mmol), in MeOH (5 mL) and 1N NaOH (10 mL) was stirred for 1 h, then diluted with $H_2O$ (50 mL). The mixture was extracted with $CHCl_3$ (10 mL, discarded), acidified (2N HCl) to pH 2, then extracted with $CHCl_3$ (10×10 mL). The extract was dried ($MgSO_4$) and evaporated to yield 4-carboxy-4,4,6,6-tetramethyl-5-oxyl-2,3,4,6,7,8-hexahydro-5H-imidazo[1,5-b]-isoxazole, compound 222 (1.028 g, 90% yield), as an orange solid. Relevant data: mp 131°–132° C. (from EtOAc:hexane 2:1); IR (KBr) 1720 br, 1471, 1457, 1225 and 1063 $cm^{-1}$. Anal. calcd for $C_{10}H_{17}N_2O_4$: C, 52.39; H, 7.47; N, 12.22; found: C, 52.68; H, 7.47; N, 12.19.

In Example 12, the bicyclic compound 222 was connected to a benzyl linker as follows: To a stirred mixture of the acid 222 (1.550 g, 6.8 mmol) and NHS (0.805 g, 7 mmol) in EtOAc (50 mL), a solution of DCC (1.442 g, 7 mmol) in EtOAc (10 mL) was added dropwise at 0° C. The mixture was allowed to warm to room temperature and stirred for 4 h. Amine 202 (hydrochloride, 2.125 g, 10 mmol) was introduced followed by dropwise addition of $Et_3N$ (1.4 mL, 10 mmol). The reaction mixture was stirred for 16 h, then filtered to remove DCU. The DCU precipitate was washed with EtOAc (5×10 mL). The combined filtrates were sequentially washed with brine (20 mL), 2N HCl (3×10 mL), brine (10 mL), saturated $NaHCO_3$ (3×10 mL), and $H_2O$ (10 mL). The filtrate was dried ($MgSO_4$) and evaporated to dryness. The residue was flash-chromatographed on a silica gel column (4×20 cm, eluant: 2% MeOH in $CHCl_3$) to yield methyl 4-(4',4',6',6'-tetramethyl-5'-oxyl-2',3',4',6',7',8'-hexahydro-5H-imidazo[1,5-b]isoxazole-4'-carbonyl)aminomethyl benzoate, compound 223 (1.670 g, 77% yield), as a yellow oil. Relevant data: IR ($CCl_4$) 1720, 1678 and 1524 $cm^{-1}$. HRMS calcd for $C_{19}H_{26}N_3O_5$: 376.1872; found: 376.1879.

In Example 13, the methoxycarbonyl group was hydrolyzed as follows: A mixture of the methyl ester 223 (1.500 g, 3.99 mmol) in MeOH (40 mL) and 1 N NaOH (20 mL) was stirred for 2 h, then diluted with $H_2O$ (50 mL). The mixture was extracted with $CHCl_3$ (3×10 mL, discarded), acidified (2N HCl) to pH 1, and extracted with $CHCl_3$ (10×10 mL). The extract was dried ($MgSO_4$) and evaporated. The residue was chromatographed over silica gel (4×35 cm, eluant: 5% MeOH in $CHCl_3$) to yield 4-(4',4',6',6'-tetramethyl-5-oxyl-2',3',4',6',7',8'-hexahydro-5H-imidazo[1,5-b]isoxazole-4'-carbonyl)aminomethyl benzoic acid, compound 224 (1.165 g, 81% yield), as an orange powder that was solid but not crystalline. Relevant data: liquified above 73° C; IR (KBr) 1705, 1640, 1613, and 1539 $cm^{-1}$; FABMS Calcd for ($C_{18}H_{24}N_3O_5+2H$): 364.2; found: 364.2. HPLC (Resolve $C_{18}$; 20 to 60% B in 15 min): 12.3 min (98%).

EXAMPLES 14–18

In these Examples, illustrated in Scheme 6, a pyrroline nitroxide radical moiety was attached to each aminomethyl arm of the core group 226 to yield the diradical 227. Three different acylation techniques were used. In each Example, the methyl protection group was subsequently removed by basic hydrolysis to produce the corresponding carboxylic acid 228.

Scheme 6

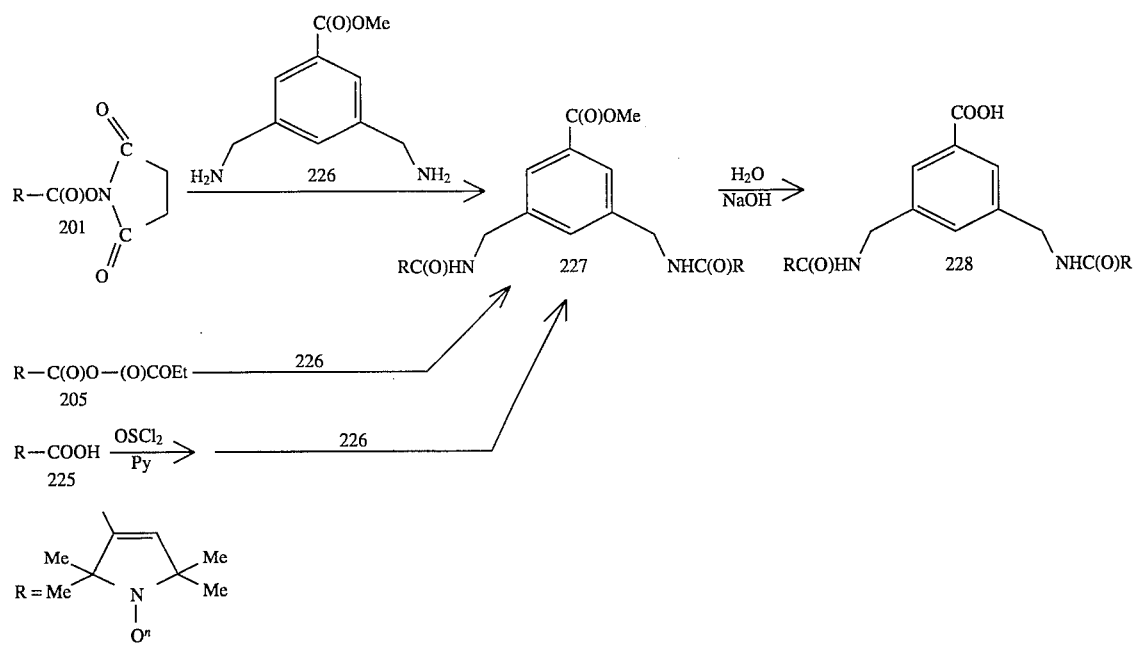

It will be appreciated that the following chemistry, pertaining to the attachment of nitroxides to the two amine-terminating arms of compound 226, is equally applicable to attaching nitroxides or any other active group to any of various other core groups, linkers, and branch groups having at least one terminal amine.

Example 14 was performed as follows: to a mixture of NHS ester 201 (2.810 g, 10 mmol) and 3,5-bis-(aminomethyl)methyl benzoate (226) (dihydrochloride, 1.068 g, 4 mmol) in DMF (50 mL), $Et_3N$ (0.84 mL, 6 mmol) was added dropwise. The mixture was stirred for 20 h, then evaporated to dryness. The residue was suspended in EtOAc (150 mL), then washed sequentially with $H_2O$ (50 mL), 2N HCl (3×20 mL), $H_2O$ (20 mL), 1N NaOH (3×20 mL), and $H_2O$ (20 mL). The residue was dried ($MgSO_4$) and evaporated. The resulting crude product was flash-chromatographed on a silica gel column (4×25 cm, eluant: $CHCl_3$) to yield purified methyl-3,5-bis-[(2',2',5',5'-tetramethyl-1-oxyl-3-pyrroline-4-carbonyl)aminomethyl]benzoate, compound 227 (2.036 g, 97% yield), as a yellow solid. Relevant data: mp 193°–194° C. (from EtOAc:hexane 1:1); IR (KBr) 1720, 1659, 1642, 1605 and 1534 $cm^{-1}$; EPR (hexane) 5 (1:0.3:1:0.3:1), $a_N$=14 G. Anal. calcd for $C_{28}H_{38}N_4O_6$: C, 63.97; H, 7.28; N, 10.64; found: C, 64.24; H, 7.23; N, 10.85.

Example 15 was performed as follows: To a stirred suspension of the diamine 226 (dihydrochloride, 1.068 g, 4 mmol) in DMF (20 mL), a solution of anhydride 205 (4.096 g, 16 mmol) in DMF (15 mL) was added. The reaction mixture was cooled to 0° C. and $Et_3N$ (1 mL, 7.2 mmol) was added dropwise. The reaction mixture was allowed to warm to room temperature, stirred for 16 h, then evaporated to dryness. The solid residue was dissolved in EtOAc (200 mL) and washed sequentially with $H_2O$ (50 mL), 2N HCl (2×50 mL), $H_2O$ (50 mL), saturated $NaHCO_3$ (2×50 mL), and $H_2O$ (50 mL). The residue was dried ($MgSO_4$) and evaporated. The residue was chromatographed over silica gel (2.5×50 cm, eluant: $CHCl_3$) to produce the diradical compound 227, (0.657 g, 31% yield), which is identical to that prepared in Example 14.

Example 16, pertaining to the preparation of the diradical 227 using the mixed anhydride 205 and the diamine 226 in free-base form, was performed as follows: The dihydrochloride (1 g) of compound 226 was dissolved in water (30 mL). The pH was increased to 10 by adding 1N NaOH. The solution was extracted with methylene chloride (7×10 mL). The extract was dried ($MgSO_4$) and evaporated to yield the diamine 226 in free-base form as a colorless low-melting solid. Immediately afterward, a solution of mixed anhydride 205 (1.413 g, 5.25 mmol) in DMF (3 mL) was added dropwise at 0° C. to a stirred solution of the free base of amine 226 (0.467 g, 1.75 mmol) and $Et_3N$ (1 mL, 7.2 mmol) in DMF (5 mL). The mixture was stirred for 16 h, then evaporated, washed, dried, evaporated, and chromatographed as described in Example 15 to yield the diradical 227 (0.230 g, 25% yield).

Example 17 pertained to the in situ formation of an acyl chloride, and proceeded as follows: To the stirred suspension of the acid 225 (0.368 g, 2 mmol) in ethanol-free chloroform (5 mL) and pyridine (0.4 mL), thionyl chloride (0.18 mL, 2.5 mmol) was added at 0° C. The mixture was allowed to heat to room temperature and stirred for 20 min. Diamine 226 (dihydrochloride, 0.134 g, 0.5 mmol) was added, followed by addition of $Et_3N$ (0.56 mL, 4 mmol). The mixture was stirred for 2 h, diluted with $CHCl_3$ (50 mL), then sequentially washed with $H_2O$ (2×20 mL), 2N HCl (3×20 mL), $H_2O$ (20 mL), saturated $K_2CO_3$ (2×20 mL), and $H_2O$ (3×20 mL). The extract was dried ($MgSO_4$) and evaporated. The residue was flash-chromatographed on a silica gel column (1.5×10 cm, eluant: $CHCl_3$) to yield the diradical 227 (0.062 g, 24% yield).

In Example 18, pertaining to the hydrolytical removal of the methyl group, a mixture of the methyl ester 227 (2.200 g, 4.18 mmol) in MeOH (50 mL) and 1N NaOH (20 mL) was stirred for 2 h, then diluted with $H_2O$ (50 mL). The mixture was extracted with $CHCl_3$ (2×20 mL, discarded), acidified (2N HCl) to pH 1, then extracted with $CHCl_3$ (5×20 mL). The extract was dried ($MgSO_4$) and evaporated to yield 3,5-bis-[(2',2',5',5'-tetramethyl-1-oxyl-3-pyrroline- 4-carbonyl)aminomethyl] benzoic acid, compound 228 (2.060 g, 96% yield), as an orange solid. Relevant data: mp 195°–196° C. (from EtOAc); IR (KBr) 1689, 1668, 1653, 1616 and 1519 cm$^{-1}$; EPR (CHCl$_3$:C$_6$H$_6$1:10) 5 (1:0.6:1:0.6:1), $a_N$=14.6 G. Anal. calcd for C$_{27}$H$_{36}$N$_4$O$_6$: C, 63.26; H, 7.08; N, 10.93; found: C, 63.25; H, 7.02; N, 10.62.

EXAMPLES 19–24

In these Examples, illustrated in Scheme 7, several nitroxide moieties were attached to the core molecule 226 to yield the corresponding diradicals 229–231. Removal of the protective methyl groups by basic hydrolysis yielded the corresponding diradical acids 232–234. As with the foregoing Examples, the chemistry of Scheme 7 is equally applicable to attaching any of various active groups that include a carboxylic acid moiety to any of various core groups, linkers, and branch groups having at least one terminal amine.

Scheme 7

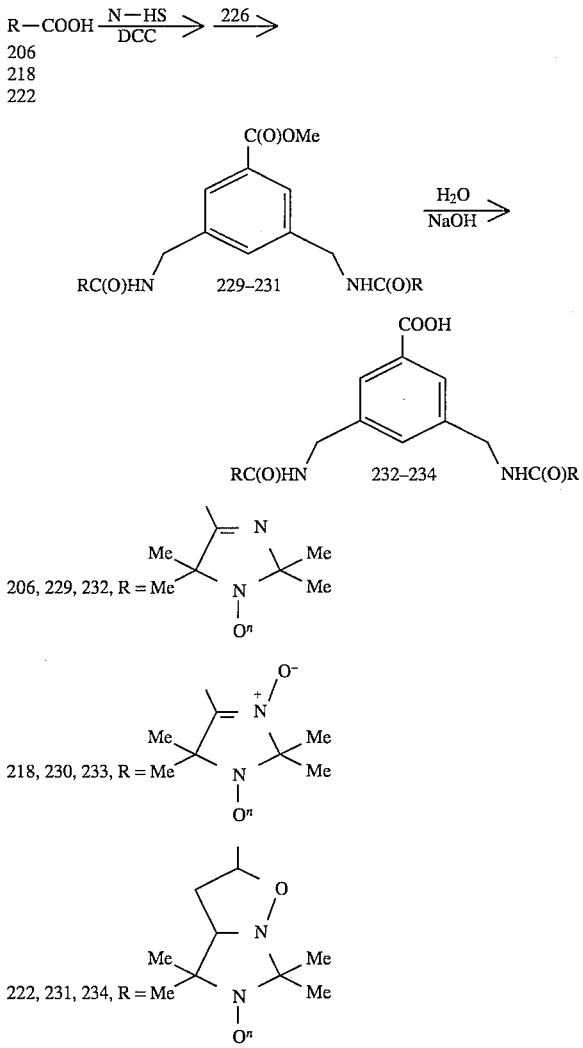

Example 19 was performed as follows: To a stirred mixture of the acid 206 (2.260 g, 12.2 mmol) and NHS (1.405 g, 12.2 mmol) in EtOAc (50 mL) a solution of DCC (2.517 g, 12.2 mmol) in EtOAc (20 mL) was added dropwise at 0° C. The mixture was allowed to warm to room temperature and stirred for 3 h. The diamine 226 (dihydrochloride, 1.303 g, 4.9 mmol) was introduced followed by dropwise addition of Et$_3$N (2.1 mL, 14.6 mmol). The reaction mixture was stirred for 16 h, then filtered to remove DCU. The DCU precipitate was washed with EtOAc (5×10 mL). The combined filtrates were sequentially washed with H$_2$O (50 mL), 2N HCl (3×20 mL), H$_2$O (20 mL), saturated NaHCO$_3$ (3×20 mL), and H$_2$O (20 mL). The filtrate was dried (MgSO$_4$) and evaporated to dryness. The residue was flash-chromatographed on a silica gel column (4×40 cm, eluant: 3% CH$_3$OH in CHCl$_3$) to yield methyl 3,5-bis-[(2', 2',5',5'-tetramethyl-3'-imidazoline-1'-oxyl-4'-carbonyl)aminomethyl] benzoate, compound 229 (2.130 g, 78% yield), as a yellow solid. Relevant data: mp 151°–152° C. (from EtOAc); IR (KBr) 1727, 1678, 1622 and 1531 cm$^{-1}$; EPR (CHCl$_3$) 5 (1:0.4:1:0.4:1), $a_N$14.3 G. Anal. calcd for C$_{26}$H$_{36}$N$_6$O$_6$+0.5H$_2$O: C, 58.09; H, 6.94; found: C, 58.22; H, 6.90. FAB MS calcd for (C$_{26}$H$_{36}$N$_6$O$_6$+3H): 531.3; found: 531.3.

Example 20 was performed as follows: To a stirred mixture of the acid 218 (4.020 g, 20 mmol) and NHS (2.300 g, 20 mmol) in EtOAc (100 mL), a solution of DCC (4.120 g, 20 mmol) in EtOAc (30 mL) was added dropwise at 0° C. The mixture was allowed to warm to room temperature and stirred for 3 h. Diamine 226 (dihydrochloride, 2.136 g, 8 mmol) was introduced followed by dropwise addition of Et$_3$N (3.5 mL, 24 mmol). The reaction mixture was stirred for 16 h, then filtered to remove DCU. The DCU precipitate was washed with EtOAc (5×20 mL). The filtrates were combined and sequentially washed with H$_2$O (50 mL), 2N HCl (3×20 mL), H$_2$O (20 mL), saturated NaHCO$_3$ (3×20 mL), and H$_2$O (20 mL). The filtrate was dried (MgSO$_4$) and evaporated to dryness. The residue was flash-chromatographed on a silica gel column (4×80 cm, eluant: 2% CH$_3$OH in CHCl$_3$) to yield methyl 3,5-bis-[(2',2',5',5'-tetramethyl- 3'-imidazoline-3'-oxide-1'-oxyl-4'-carbonyl)aminomethyl] benzoate, compound 230 (3.720 g, 83% yield) as a yellow solid. Relevant data: mp 168°–169° C. (from ethyl acetate); IR (KBr) 1721, 1670, 1628, 1577 and 1534 cm$^{-1}$; EPR (CHCl$_3$) 5 (1:0.45:1:0.45:1), $a_N$=14.0 G.

Example 21 was performed as follows: To a stirred mixture of the acid 222 (1.832 g, 8 mmol) and NHS (0.920 g, 8 mmol) in EtOAc (50 mL), a solution of DCC (1.648 g, 8 mmol) in ethyl acetate (20 mL) was added dropwise at 0° C. The mixture was allowed to warm to room temperature and stirred for 3 h. The diamine 226 (dihydrochloride, 0.854 g, 3.2 mmol) was then introduced followed by dropwise addition of Et$_3$N (1.4 mL, 10 mmol). The reaction mixture was stirred for 16 h, then filtered to remove DCU. The DCU precipitate was washed with EtOAc (5×10 mL). The filtrates were combined and sequentially washed with H$_2$O (50 mL), 2N HCl (3×10 mL), H$_2$O (20 mL), saturated NaHCO$_3$ (3×10 mL), and H$_2$O (20 mL). The filtrate was dried (MgSO$_4$), and evaporated to dryness. The residue was flash-chromatographed on a silica gel column (4×30 cm, eluant: 2% MeOH in CHCl$_3$) to yield methyl 3,5-bis- [(4',4',6',6'-tetramethyl-5-oxyl-2',3',4',6',7',8'-hexahydro-5H-imidazo[1,5-b]isoxazole-4'-carbonyl)aminomethyl] benzoate, compound 231 (1.180 g, 60% yield), as a yellow glassy (not crystalline) solid. Relevant data: liquifies above 75° C.; IR (KBr) 1723, 1672, and 1527 cm$^{-1}$; EPR (CHCl$_3$): 5 (1:0.45:1:0.45:1), $a_N$=14.0 G; FAB MS calcd for (C$_{30}$H$_{44}$N$_6$O$_8$+3H): 619.4; found: 619.4.

In Example 22, a mixture of the methyl ester 229 (0.120 g, 0.227 mmol) in MeOH (3 mL) and 1N NaOH (1 mL) was stirred for 3 h, then diluted with H$_2$O (5 mL). The mixture was extracted with CHCl$_3$ (10 mL, discarded), acidified (2N HCl) to pH 1, and extracted with CHCl₃ (5×10 mL). The extract was dried (MgSO₄) and evaporated to yield 3,5-bis-[(2',2',5',5'-tetramethyl-3'-imidazoline-1'-oxyl-4'-carbonyl)aminomethyl] benzoic acid, compound 232 (0.104 g, 89% yield), as an orange solid. Relevant data: mp 206°–207√ C. (from EtOAc:EtOH 20:1); IR (KBr) 1705, 1680, 1620 and 1530 cm$^{-1}$; EPR (CHCl₃:C₆H₆1:10) 5 (1:0.7:1:0.7:1), $a_N$=14.3. Anal. calcd for C₂₅H₃₄N₆O₆: C, 58.35; H, 6.66; N, 16.33; found: C, 58.48; H, 6.72; N, 16.24.

In Example 23, a mixture of the methyl ester 230 (0.550 g, 0.98 mmol) in MeOH (50 mL) and 1N NaOH (10 mL) was heated to reflux with stirring for 0.5 h, cooled to room temperature, and diluted with H₂O (50 mL). The mixture was extracted with CHCl₃ (3×10 mL, discarded), acidified (2N HCl) to pH 1, and extracted with CHCl₃ (7×20 mL). The extract was dried (MgSO₄), and evaporated. The residue was chromatographed over silica gel (4×20 cm, eluant: 2% CH₃OH in CHCl₃) to yield 3,5-bis-[(2',2',5',5'-tetramethylcalcd for (C₂₉H₄₂N₆O₈+3H): 605.3; found: 605.3. HPLC (Resolve C₁₈; 0 to 60% B in 15 min): 12.6 min (98%).

EXAMPLES 25–30

These Examples are illustrated in Scheme 8. In Example 25 a nitroxide radical was connected to a representative branch molecule, diethylenetriamine (DETA), to produce the diradical 235. In Examples 26–30 three different linkers were attached to compound 235, followed by removal of the methyl protection from the linkers by basic hydrolysis. It will be appreciated that the same chemistry as shown in Scheme 8 can be employed to attach the corresponding linkers to any of various branch groups and core groups.

Scheme 8

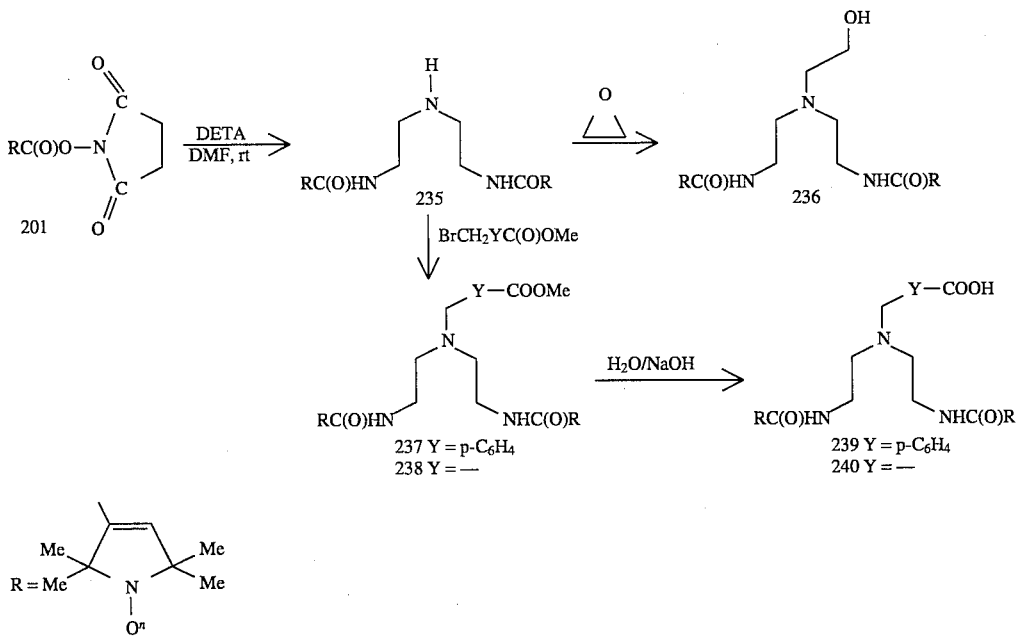

3-imidazoline-3-oxide-1-oxyl-4-carbonyl)aminomethyl] benzoic acid, compound 233 (0.521 g, 97% yield), as an orange solid. Relevant data: mp 178°–179° C. (from EtOAc); IR (KBr) 1693, 1665, 1655, 1604, 1556 and 1535 cm$^{-1}$; EPR (CHCl₃:C₆H₆1:15) 5 (1:0.55:1:0.55:1), $a_N$=13.5 G. Anal. calcd for C₂₅H₃₄N₆O₈: C, 54.94; H, 6.27; N, 15.38; found: C, 54.65; H, 6.33; N, 15.44.

In Example 24, a mixture of the methyl ester 231 (1.200 g, 4.18 mmol) in MeOH (100 mL) and 1N NaOH (60 mL) was stirred for 3 h, then diluted with H₂O (50 mL). The mixture was extracted with CHCl₃ (3×10 mL, discarded), acidified (2N HCl) to pH 1, and extracted with CHCl₃ (7×20 mL). The extract was dried (MgSO₄) and evaporated. The residue was chromatographed over silica gel (4×30 cm, eluant: 5% MeOH in CHCl₃) to yield 3,5-bis-[(4',4',6',6'-tetramethyl-5'-oxyl-2',3',4',6',7',8'-hexahydro-5H-imidazo[1,5-b]isoxazole-4'-carbonyl)aminomethyl] benzoic acid, compound 234 (0.702 g, 60% yield), as a yellow powder that was solid but not crystalline. Relevant data: liquifies above 95° C.; IR (KBr) 1717, 1673, 1607, and 1532 cm$^{-1}$; EPR (CHCl₃:C₆H₆1:10) 5 (1:0.22:1:0.22:1), $a_N$=14.4 G. FAB MS Specifically, in Example 25, a mixture of the NHS ester 201 (3.091 g, 1.1 mmol) and diethylene triamine (DETA) (0.54 mL, 0.5 mmol) in DMF (25 mL) was stirred for 16 h. The solvent was removed under reduced pressure, and the residue was dissolved in EtOAc (100 mL) and extracted with 1% HCl (6×20 mL). The acidic extract was basified with 2N NaOH to pH 12 and extracted with CHCl₃ (6×20 mL). The extract was dried (MgSO₄) and evaporated. The residue was treated with cold ether (10 mL) to yield 1.875 g (86% yield) of the diradical compound bis-[2-(2',2',5',5'-tetramethylpyrroline-3'-carbonyl)aminoethyl] amine, compound 235, as an orange-yellow solid. Relevant data: mp 134°–135° C. (from EtOAc): IR (KBr) 1658, 1649, 1619, 1610 and 1555 cm$^{-1}$; EPR (CHCl₃) 5 (1:2:3:2:1), $a_N$=14.6 G. Anal. calcd for C₂₂H₃₇N₅O₄: C, 60.67; H, 8.56; N, 14.69; found: C, 60.57; H, 8.42; N, 14.98.

In Example 26, a solution of the diradical 235 (0 435 g, 1 mmol) in MeOH (20 mL) was cooled to 0° C. and ethylene oxide (1 mL, about 20 mmol) was introduced with stirring. The mixture was allowed to heat to room temperature, stirred for 3 days, then evaporated. The residue was chromatographed over silica gel (1.5×20 cm, eluant: 2% MeOH in CHCl$_3$) to yield 0.380 g (79% yield) of bis-[2-(2',2',5',5'-tetramethylpyrroline- 3'-carbonyl)aminoethyl]-(2-hydroxyethyl) amine, compound 236, as an orange-yellow solid. Relevant data: mp 122°–123° C. (from hexane:EtOAc 1:2); IR (KBr) 3480, 3335, 2823, 1658, 1645, 1615, 1604, 1538, 1465, 1356, 1300, 1166, 1153 and 1048 cm$^{-1}$; EPR (CHCl$_3$) 5 (1:2:3:2:1), a$_N$=14.5 G. Anal. calcd for C$_{24}$H$_{41}$N$_5$O$_4$: C, 60.10; H, 8.62; N, 14.60; found: C, 60.30; H, 8.84; N, 14.28.

Example 27 was performed as follows: To a mixture of the diradical 235 (0.435 g, 1 mmol) and K$_2$CO$_3$ (0.276 g, 2 mmol) in MeCN (10 mL), methyl 4-bromomethyl benzoate (0.229 g, 1 mmol) was added. The mixture was stirred for 16 h at 60° C., filtered from inorganic material, then evaporated. The residue was purified by flash-chromatography over silica gel (1.5×20 cm, eluant: CHCl$_3$) to yield 0.559 g (93% yield) of the diradical compound bis-[2-(2',2',5', 5'-tetramethylpyrroline-3'-carbonyl)aminoethyl]-(4-methoxycarbonylbenzyl) amine, compound 237, as an orange solid. Relevant data: mp 162°–164° C. (hexane from ether); IR (KBr) 3364, 3067, 2868, 1722, 1661, 1539, 1281, 1162 and 1110 cm$^{-1}$; EPR (CHCl$_3$) 5 (1:2:3:2:1), a$_N$=14.5 G. Anal. calcd for C$_{31}$H$_{45}$N$_5$O$_7$: C, 62.09; H, 7.56; N, 11.68; found: C, 62.38; H, 7.75; N, 11.47.

Example 28 was performed as follows: To a mixture of the diradical 235 (0.400 g, 0.92 mmol) and K$_2$CO$_3$ (0.414 g, 3 mmol) in MeCN (10 mL), methyl bromoacetate (0.102 mL, 1.1 mmol) was added. The mixture was stirred 5 h at 40° C., filtered to remove inorganic material, then evaporated. The residue was dissolved in ether (10 mL) and stored for 15 h at −15° C. The residue was then filtered and recrystallized from hexane:EtOAc (1:1) to yield 0.425 g (91% yield) of the diradical compound bis-[2-(2',2',5',5'-tetramethylpyrroline-3'-carbonyl)aminoethyl] methoxycarbonylmethyl amine, compound 238 as a yellow solid. Relevant data: mp 52°–54° C. (from hexane:EtOAc 1:1): IR (KBr) 1744, 1654, 1646, 1619, 1605 and 1543 cm$^{-1}$; EPR (CHCl$_3$) 5 (1:2:3:2:1), a$_N$=14.5 G. HRMS calcd for C$_{25}$H$_{41}$N$_5$O$_6$: 507.3056; found: 507.3051.

Example 29 was performed as follows: To a solution of the ester 237 (0.530 g, 0.88 mmol) in MeOH (20 mL), 1N NaOH (20 mL, 20 mmol) was added. The mixture was stirred for 5 h, acidified with 2N HCl to pH 6, saturated with NaCl, then extracted for 3 days with CHCl$_3$ in a liquid-liquid extractor. The extract was evaporated and the residue was treated with ether (10 mL) to yield 0.511 g of a crude precipitate. The precipitate was dissolved in MeOH (5 mL), and re-precipitated with ether (50 mL) to yield 0.401 g (77% yield) of bis-[2-(2',2',5',5'-tetramethylpyrroline-3'-carbonyl)aminoethyl]-(4-carboxybenzyl) amine, compound 239, as a yellowish powder. Relevant data: mp 157°–159° C. (ether from MeOH); IR (KBr) 3352, 3060, 2968, 1715, 1662, 1611, 1539, 1467, 1382, 1301, and 1162 cm$^{-1}$; EPR (CHCl$_3$) 5, a$_N$=14.9 G. HRMS calcd for C$_{30}$H$_{43}$N$_5$O$_7$: 585.3162; found: 585.3180. HPLC (Resolve C$_{18}$; 60% B): 4.4 min (99%).

To a solution of the ester 238 (0.400 g, 0.79 mmol) in MeOH (5 mL), 1N NaOH (4 mL, 4 mmol) was added. The mixture was stirred for 4 h, acidified (2N HCl) to pH 6, saturated with NaCl, and extracted for 72 h with CHCl$_3$ in a liquid-liquid extractor. The extract was evaporated and the residue was treated with ether (10 mL) to yield 0.271 g (70%) of bis-[2-(2',2',5',5'-tetramethylpyrroline-3'-carbonyl)aminoethyl] carboxymethyl amine, compound 240 as a yellowish powder: mp 124°–126° C. (from EtOAc); IR (KBr) 1661, 1619, and 1537 cm$^{-1}$. FAB MS calcd for (C$_{24}$H$_{39}$N$_5$O$_6$+3H) 496.3; found: 496.3. HPLC (Resolve C$_{18}$; 50% B): 5.1 min (98%).

EXAMPLES 31–35

These Examples are illustrated in Scheme 9. In Example 31 compound 235 was activated by treatment with phosgene. The resulting chlorocarbamoyl derivative 241 was reactive and unstable to isolation. However, in Example 32, compound 241 was converted into a stable carbamoyl NHS ester 242. The carbamoyl chloride 241, used in solution, and the NHS ester 242 were connected to the aminomethyl benzene compound 202 in Examples 33 and 34, respectively, to yield compound 243. Methyl protection on compound 243 was removed by basic hydrolysis in Example 35 to yield a corresponding carboxylic acid 244. It will be appreciated that this same chemistry can be employed to attach any of various branch groups to linkers and any of various branch groups or linkers to core groups.

Scheme 9

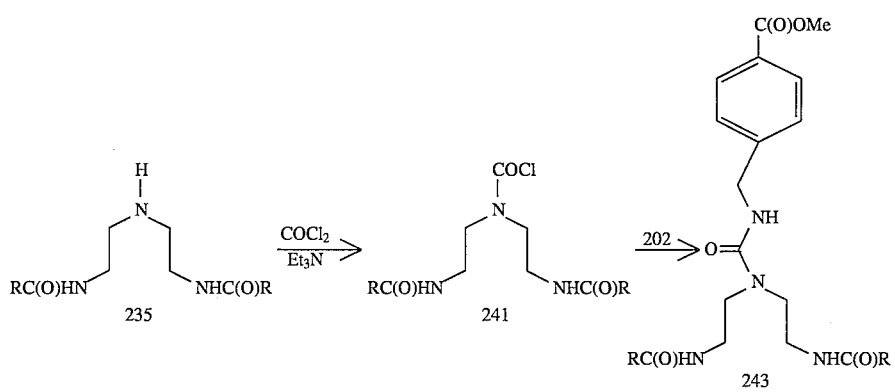

-continued
Scheme 9

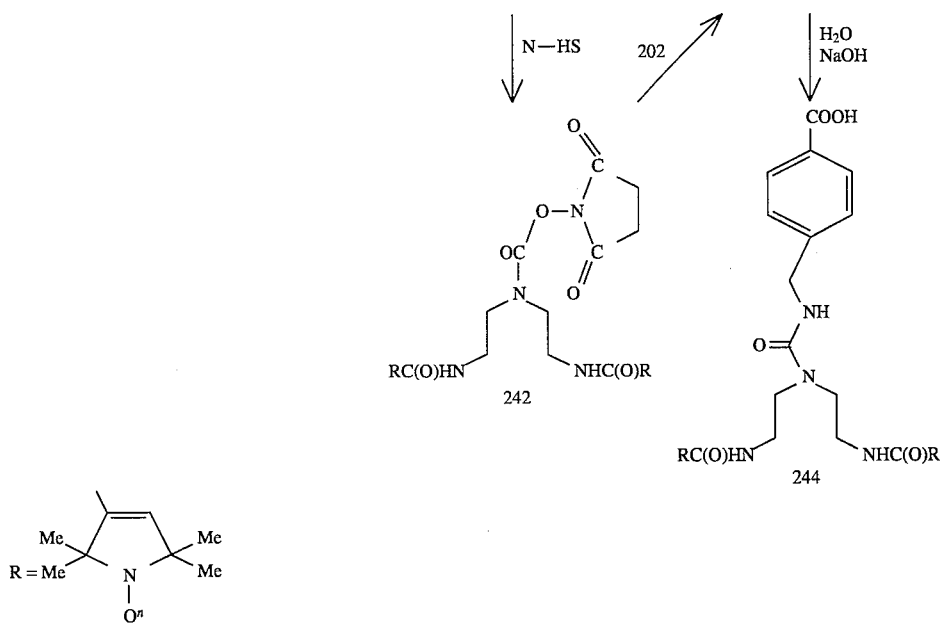

In Example 31, a suspension of the diradical 235 (0.600 g, 1.38 mmol) and Et$_3$N (0.6 mL, 4.2 mmol) in EtOAc (20 mL) was added to a mixture of COCl$_2$ (1.93M in 2.2 mL toluene, 4.2 mmol) and EtOAc (20 mL) at 0° C. The reaction mixture was allowed to warm to room temperature, stirred for 0.5 h, then evaporated at 20° C. to one-third the original volume to remove excess COCl$_2$. More EtOAc (30 mL) was added and the mixture was again evaporated to one-third its original volume. The residue was diluted with EtOAc (30 mL) to yield a mixture that served as a source of the carbamoyl chloride {bis [3-(2',2',5',5'-tetramethylpyrroline-3'-carbonyl)aminoethyl]amino}carbonyl chloride, compound 241.

In Example 32, NHS (0.115 g, 1 mmol) in EtOAc (20 mL) was added to a solution of carbamoyl chloride 241 (synthesized from 0.217 g, 0.5 mmol of the diradical 235), followed by dropwise addition of Et$_3$N (0.43 mL, 3 mmol). The mixture was stirred for 16 h at 60° C., then cooled to room temperature. The liquid was filtered to remove salts, then evaporated. The residue was chromatographed over silica gel (4×25 cm, eluant: 1% MeOH in CHCl$_3$) to elute succinimidyl N',N'-bis [(3-(2", 2", 5", 5"-tetramethyl-1'-oxyl-3"-pyrroline-4"-carbonyl)aminoethyl]carbamate, compound 242 (0.146 g, 51% yield) as yellow needles. Relevant data: mp 199°–200° C. (from EtOAc); IR (KBr): 1800, 1768, 1740, 1655, 1616 and 1552 cm$^{-1}$; EPR (CHCl$_3$) 3 (br.) (1:1:1), a$_N$=14.5. Anal. calcd for C$_{27}$H$_{40}$N$_6$O$_8$: C, 56.24, H 6.99, N 14.5 [+H$_2$O: C, 54.53H, 7.12N, 14.13]; found: C, 55.84H, 7.23, N 13.87. HRMS calcd for C$_{27}$H$_{40}$N$_6$O$_8$: 576.2907; found: 576.2878.

In Example 33, carbamoyl chloride 241 was reacted with the amine 202 as follows: To the solution of carbamoyl chloride 241 (synthesized from 0.600 g, 1.38 mmol of the diradical 235) in EtOAc (50 mL), amine 202 (hydrochloride, 0.587 g, 2.76 mmol) was added followed by dropwise addition of Et$_3$N (0.6 mL, 4.2 mmol). The mixture was stirred for 16 h at 60° C., then cooled to room temperature and filtered to remove salts. The filtrate was diluted with EtOAc (100 mL) and washed sequentially with 2N HCl (3×20 mL) and brine (2×20 mL). The filtrate was dried (MgSO$_4$) and evaporated to dryness. The residue was chromatographed over silica gel (1.5×40 cm, eluant: MeOH in CHCl$_3$ from 1% to 5%) to elute methyl 4-{N',N'-bis[3"-(2", 2",5",5"-tetramethyl-1-oxyl-3-pyrroline-4-carbonyl)aminoethyl]}ureidomethyl benzoate, compound 243 (0.447 g, 50% yield) as a yellow powder, solid but not crystalline. Relevant data: liquifies above 120° C.; IR (KBr) 1720, 1658, 1635, 1615 and 1537 cm$^{-1}$; EPR (CHCl$_3$) 3 (broad), a$_N$=14.6. FAB MS calcd for (C$_{32}$H$_{46}$N$_6$O$_7$+3H): 629.4; found: 629.4.

In Example 34, the amine 202 was acylated with NHS ester 242 as follows: A mixture of the NHS ester 242 (0.029 g, 0.05 mmol), amine 202 (hydrochloride, 0.011 g, 0.05 mmol), and Et$_3$N (14 µL, 0.1 mmol) in DMF (2 mL) was stirred for 16 h and evaporated. The residue was dissolved in EtOAc (20 mL) and washed sequentially with 2N HCl (3×10 mL) and brine (2×10 mL). The residue was dried (MgSO$_4$) and evaporated to yield compound 243, 0.030 g (96% yield), identical to the compound prepared in Example 33.

In Example 35, a mixture of the methyl ester 243 (0.400 g, 0.64 mmol) in MeOH (10 mL) and 1N NaOH (3 mL) was stirred for 8 h, then diluted with H$_2$O (50 mL). The mixture was extracted with CHCl$_3$ (3×20 mL, discarded), acidified (2N HCl) to pH 2, and extracted with CHCl$_3$ (5×20 mL). The extract was dried (MgSO$_4$) and evaporated. The residue was flash-chromatographed over silica gel (1.5×15 cm, eluant: 10% MEOH in CHCl$_3$) to yield 4-{N',N'-bis[3'-(2",2",5", 5"-tetramethyl-1-oxyl-3 -pyrroline-4-carbonyl)aminoethyl]}ureidomethyl benzoic acid, compound 244 (0.360 g, 92% yield) as a yellow powder, solid but not crystalline. Relevant data: liquifies above 195° C.; IR (KBr) 1713, 1661, 1617, and 1535 cm$^{-1}$; EPR (CHCl$_3$) 3 br. (1:1:1), a$_N$=14.6. FAB MS calcd for (C$_{31}$H$_{44}$N$_6$O$_7$+3H): 615.3; found: 615.3. HPLC (Resolve C$_{18}$; 20 to 65% B in 15 min): 9.7 min (99.6%).

EXAMPLES 36–39

In Examples 36–39, nitroxide-radical moieties were connected to various representative branch groups, wherein each branch group was of a type serving to triple the amplification level. These Examples are illustrated in Scheme 10. The resulting triradicals 246, 248, 250, 253 can be used in amplifier molecule synthesis by way of an "active-group upgrade" strategy. I.e., compound 246 can be connected to a branch group, linker, or core group via its nitrogen that has an unshared electron pair, as described in Example 44, below; compounds 245, 250, 253 can be linked to a branch group, linker, or core group via the hydroxy group, as described in Example 45, below. Compound 252 is representative of branch groups, which can be employed according to the present invention, having arms lacking amine groups.

treated with cold ether (20 mL), filtered, and recrystallized from EtOAc to yield 1.513 g (94% yield) of tris [(2,2,5,5-tetramethyl-1-oxyl-3-pyrroline-4-carbonyl)aminoethyl)] amine, compound as an orange solid. Relevant data: mp 93°–95° C. (from EtOAc); IR (KBr) 1653, 1611, 1545, 1464, 1302 and 1165 cm$^{-1}$; EPR (benzene:CHCl$_3$ 15:1) 7, $a_N$=14.2 G. Anal. calcd for $C_{33}H_{54}N_7O_6$: C, 61.47; H, 8.44; N, 15.20; found: C, 61.33; H, 8.50; N, 15.38.

Example 37 was performed as follows: To a stirred suspension of 3-amino-2,2-bis(aminomethyl)-1-propanol 247 (trihydrochloride, 0.405 g, 1.67 mmol) and NHS ester 201 (1.549 g, 5.51 mmol) in DMF (20 mL), Et$_3$N (1.2 mL, 8.35 mmol) was added dropwise. The mixture was stirred for

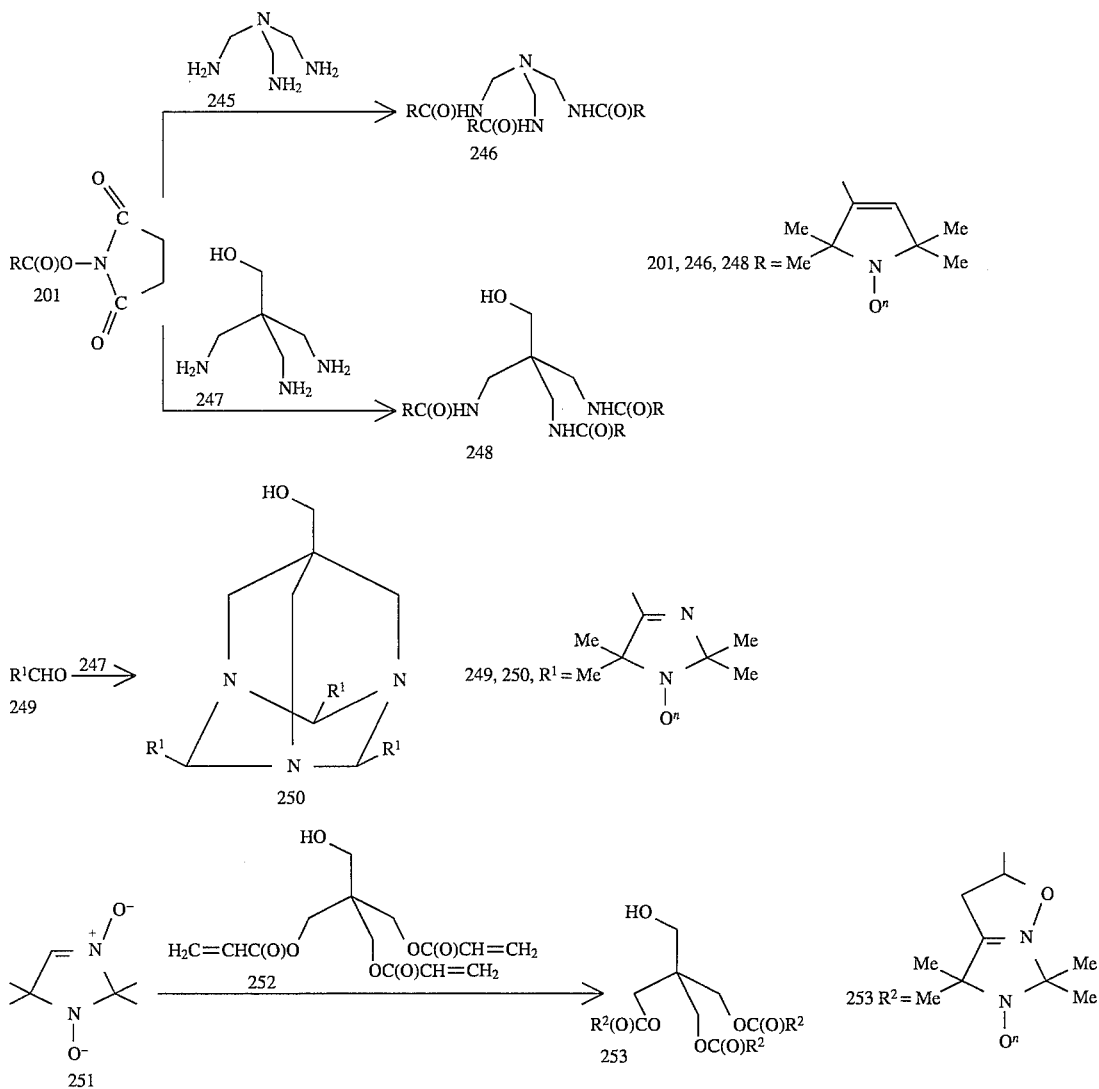

Scheme 10

In Example 36, a mixture of the NHS ester (2,810 g, 10 mmol) and tris(aminoethyl) amine 245 (0.37 mL, 2.5 mmol) in DMF (20 mL) was stirred for 16 h. The solvent was evaporated under reduced pressure. The precipitate was washed with EtOAc (5×10 mL). The combined filtrate was washed sequentially with H$_2$O (30 mL), saturated NaHCO$_3$ (3×30 mL), and H$_2$O (30 mL). The residue was dried (MgSO$_4$) and evaporated. The resulting crude product was 16 h, and evaporated under reduced pressure. The residue was redissolved in EtOAc (100 mL) and sequentially washed with H$_2$O (3×20 mL), 2N HCl (3×20 mL), H$_2$O (2×20 mL), saturated NaHCO$_3$ (3×20 mL), and H$_2$O (20 mL). The residue was dried (MgSO$_4$) and evaporated. The resulting crude product was chromatographed on a silica gel column (2×25 cm, eluant: 3% MeOH in CHCl$_3$) to yield 2,2,2-tris [(2',2',5',5'-tetramethyl-1'-oxyl-3'-pyrroline-4'-carbonyl) aminomethyl] hydroxymethyl methane, compound 248 (0.862 g, 82% yield), as a yellow glassy solid. Relevant data: liquifies above 115° C. (hexane from EtOAc); IR (KBr) 1658, 1616, 1534, 1309 and 1162 cm$^{-1}$; EPR (CHCl$_3$) 7 (1:0.6:0.6:1:0.6:0.6:1), $a_N$=14.2 G. Anal. calcd for $C_{32}H_{51}N_6O_7$: C, 60.84; H, 8.14; N, 13.30; found: C, 60.43; H, 8.41; N, 12.98.

Example 38 was performed as follows: To a stirred mixture of 3-amino-2,2-bis(aminomethyl)-1-propanol 247 (trihydrochloride, 0.061 g, 0.25 mmol) and nitroxide aldehyde 249 (0.150 g, 0.8 mmol) in EtOH (5 mL), Et$_3$N (0.18 mL, 1.25 mmol) was added. The mixture was stirred for 3 days, then evaporated. The crude product was purified by preparative TLC (eluant: MeCN:H20 9:1) to yield the triradical 7-hydroxymethyl-2,4,6-tris(2',2',5',5'-tetramethyl-3'-imidazoline- 1'-oxyl-4'-yl)-1,3,5-triazaadamantane, compound 250 (0.085 g, 58% yield) as a yellow solid. Relevant data: mp 208°–209° C. (from EtOAc), IR (KBr) 1637, 1626, 1469, 1359, 1260 and 981 cm$^{-1}$; EPR (CHCl$_3$) 7, $a_N$=14.4 G. Anal. calcd for $C_{29}H_{48}N_9O_4$: C, 59.36; H, 8.25; N, 21.48; found: C, 59.05; H, 8.18; N, 21.83.

In Example 39, a mixture of the aldonitrone 251 (0.157 g, 1 mmol) and pentaerythritol triacrylate 252 (technical, 0.060 g, 0.2 mmol) in CHCl$_3$ (0.5 mL) was stirred for 16 h at 50° C., then cooled. The reaction product was loaded on a silica gel column (2.5×20 cm), and chromatographed using CHCl$_3$ as an eluant. This procedure yielded 0.052 g (34% yield) of the triradical pentaerythritol tris-[(4',4',6',6-tetramethyl-5'-oxyl-2',3',4',6',7',8'-hexahydro-5H-imidazo[1,5-b]isoxazole-4'-yl)formate], compound 253, as a yellow glassy solid. Relevant data: liquifies above 130° C. (from ethyl acetate-:hexane 1:1), IR (KBr) 1737, 1471, 1365, 1290, 1200 and 1039 cm$^{-1}$; EPR (CHCl$_3$) 7, $a_N$=14.6 G. Anal. calcd for $C_{35}H_{57}N_6O_{13}$: C, 54.60; H, 7.46; N, 10.92; found: C, 54.97; H, 7.39; N, 11.27.

EXAMPLES 40–41

These Examples are illustrated in Scheme 11. In Example 40 the nitroxide tetraradical amplifier 255 was synthesized by connecting the diradical intermediate 235 (synthesized in Example 25) to the core molecule 254 by a nucleophilic substitution reaction. In Example 41, removal of the methyl protection group of compound 254 by basic hydrolysis resulted in the formation of a corresponding acid 256. Thus, these Examples represent yet another way to synthesize amplifiers according to the present invention by an active-group upgrade strategy. I.e., the reaction was started using the mono-nitroxide 201 which was connected to the branch molecule DETA in Example 25 to yield the diradical 235 representing an "upgraded" active group, followed by linking the diradical 235 to a representative core molecule.

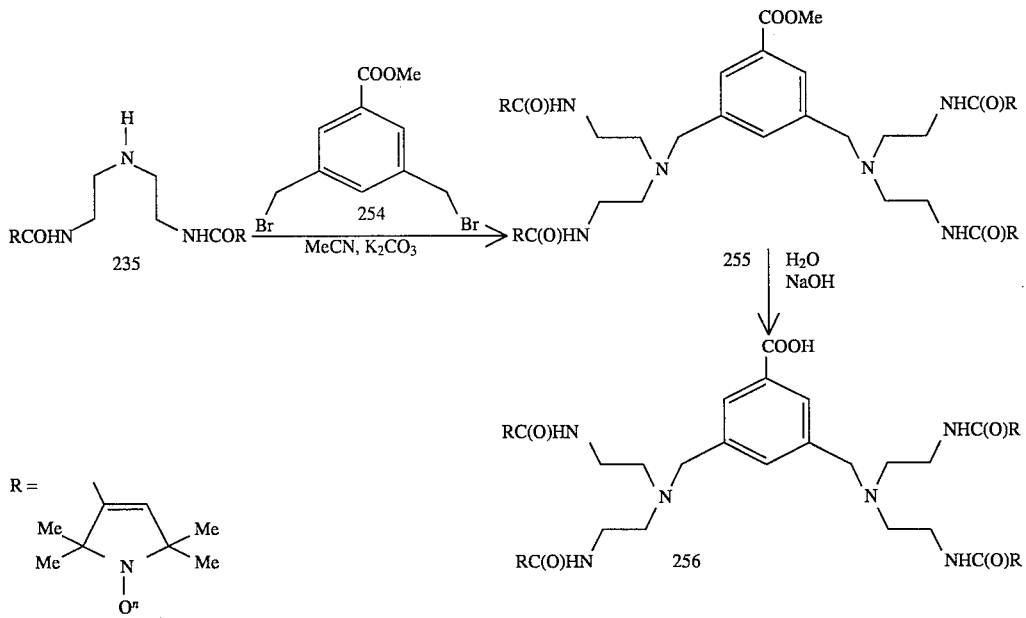

Scheme 11

In Example 40, a mixture of 3,5-bis(bromomethyl) methyl benzoate 254 (0.644 g, 2 mmol), the diradical 235 (1.784 g, 4.1 mmol), and K$_2$CO$_3$ (1.104 g, 8 mmol) in MeCN (50 mL) was stirred for 16 h at 60° C., then cooled to room temperature. The mixture was filtered to remove inorganic material and evaporated. The residue was chromatographed over silica gel (4×25 cm, eluant: CHCl$_3$) to yield the tetraradical methyl 3,5-bis-[(2',2',5',5'-tetramethyl-1'-oxyl-3'-pyrroline-4'-carbonyl) aminoethyl]aminomethyl benzoate, compound (1.349 g, 65% yield) as a yellow powder, solid but not crystalline. Relevant data: liquifies above 80° C.; IR (KBr) 1724, 1658, 1616, and 1538 cm$^{-1}$; EPR (CHCl$_3$:C$_6$H$_6$1:10) 8 (broadened). Anal. calcd for $C_{54}H_{82}N_{10}O_{10}$: C, 62.89H, 8.01N, 13.5 8 (+2 HCl:C, 58.47H, 7.67N 12.68); found: C, 58.81; H. 7.54; N, 12.10. FAB MS calcd for ($C_{54}H_{82}N_{10}O_{10}$+5H): 1035.7; found 1035.7.

In Example 41, a mixture of the tetraradical methyl ester 255 (0.880 g, 0.8 mmol) in MeOH (20 mL) and 1N NaOH (5 mL) was stirred for 3 h, then diluted with H$_2$O (20 mL). The mixture was acidified (2N HCl) to pH 5, then extracted with CHCl$_3$ (10×10 mL). The extract was dried (MgSO$_4$) and evaporated to yield 3,5-bis-[(2',2',5',5 '-tetramethyl-1'-oxyl-3'-pyrroline-4'-carbonyl)aminoethyl]aminomethyl benzoic acid, compound 256 (0.808 g, 93% yield) as a yellow powder. Relevant data: liquifies above 130° C.; IR (KBr) 1717, 1660, 1616, and 1538 cm$^{-1}$. FAB MS calcd for ($C_{53}H_{80}N_{10}O_{10}$: +5H) 1021.6; found: 1021.6. HPLC (Resolve $C_{18}$; 0 to 60% B): 13.1 min (99%).

EXAMPLES 42–43

These Examples are illustrated in Scheme 12. In Example 42 we used another method of introducing an "upgraded" active-group moiety, represented by diradical 235, using phosgene activation, similar to the chemistry of Example 31. The resulting intermediate, carbamoyl chloride 241, was reacted with diamine 226 to yield the tetraradical amplifier 257. Hydrolytic removal of the protective group in Example 43 by basic hydrolysis yielded the corresponding tetraradical acid 258.

In Example 43, a mixture of the methyl ester 257 (0.360 g, 0.38 mmol) in MeOH (5 mL) and 1N NaOH (3 mL) was stirred for 5 h, diluted with $H_2O$ (20 mL), then acidified (2N HCl) to pH 2. The mixture was extracted with $CHCl_3$ (5×20 mL). The extract was dried ($MgSO_4$) and evaporated to yield 3,5-bis[N,N'-bis(3-(2",2",5",5"-tetramethyl-1"-oxyl-3"-pyrroline- 4"-carbonyl) aminoethyl]ureidomethyl benzoic acid, compound 258 (0.252 g, 71% yield) as a yellow solid. Relevant data: mp 149°–150° C. (from EtOAc); IR (KBr) 1694, 1671, 1645, 1632, 1552, 1461, 1300 and 1159 cm$^{-1}$; EPR ($CHCl_3$) 3 (br.) (1:1:1), $a_N$=14.6. FAB MS calcd for ($C_{55}H_{46}N_7O_8$+5H): 937.3; found: 937.3. HPLC (Resolve $C_{18}$; 0 to 60% B in 15 min): 9.0 min (95%).

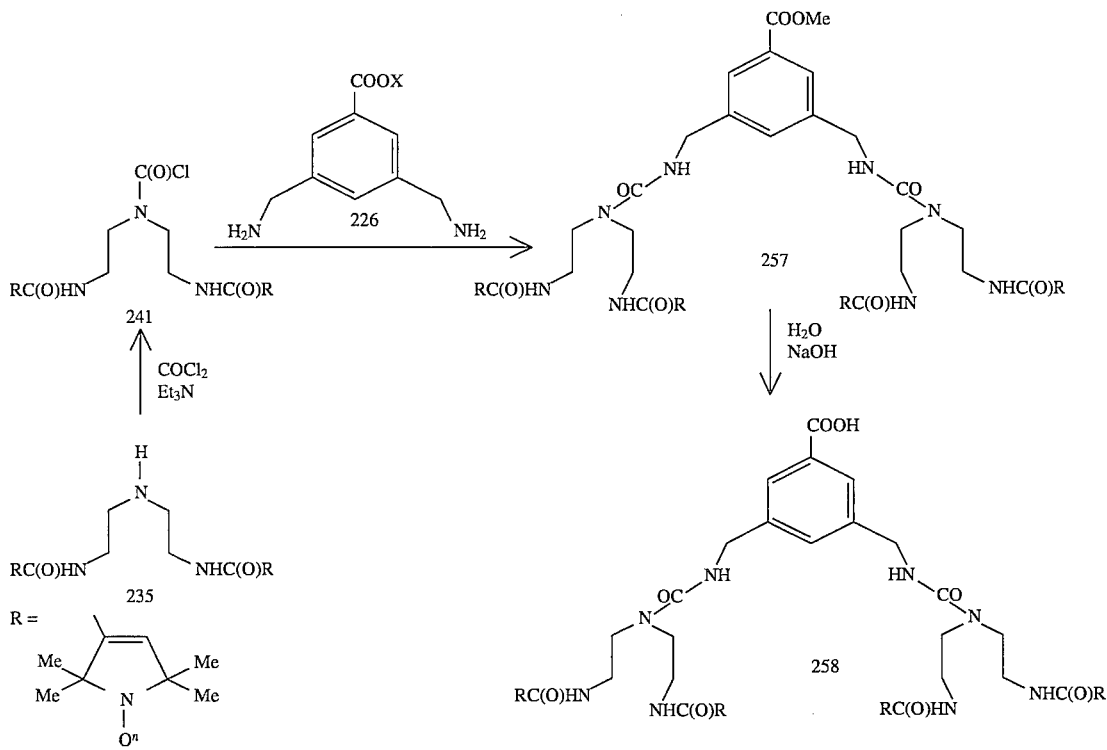

Scheme 12

Example 42 was performed as follows: To a solution of carbamoyl chloride 241 (prepared under the conditions of Example 31 from 0.870 g, 2 mmol, of diradical 235) in EtOAc (50 mL), diamine 242 (dihydrochloride, 0.267 g, 1 mmol) was added, followed by dropwise addition of $Et_3N$ (0.6 mL, 4.2 mmol). The mixture was stirred for 16 h at 70° C., then cooled to room temperature and filtered to remove salts. The filtrate was diluted with EtOAc (100 mL) and washed sequentially with 2N HCl (3×20 mL) and brine (2×20 mL). The filtrate was then dried ($MgSO_4$) and evaporated to dryness. The residue was chromatographed over silica gel (4×35 cm, eluant: 2% MeOH in $CHCl_3$) to elute the tetraradical methyl 3,5-bis[N,N'-bis(3'-(2",2",5",5"-tetramethyl-1"-oxyl-3"-pyrroline- 4"-carbonyl)aminoethyl]ureidomethyl benzoate, compound 257 (0.848 g, 90% yield) as a red oil. Relevant data: IR ($CHCl_3$) 1726, 1671, 1622, and 1521 cm$^{-1}$; EPR ($CHCl_3$) 3 (hr.), $a_N$=14.6.

EXAMPLES 44–46

In these Examples, illustrated in Scheme 13, we used triradicals 246 and 248 (Scheme 10) as upgraded active groups. In Example 44, the amine-triradical 246 was connected to a representative methyl benzene moiety in an alkylation reaction to form compound 259 having an amplification factor of three. In Example 45, the hydroxy group of the triradical 248 was activated with phosgene and the resulting intermediate chloroformate 260 was connected to a core diamine 226 to produce the hexaradical 261. In Example 46, removal of the protected methyl group of compound 261 yielded the corresponding hexaradical acid 262.

Scheme 13

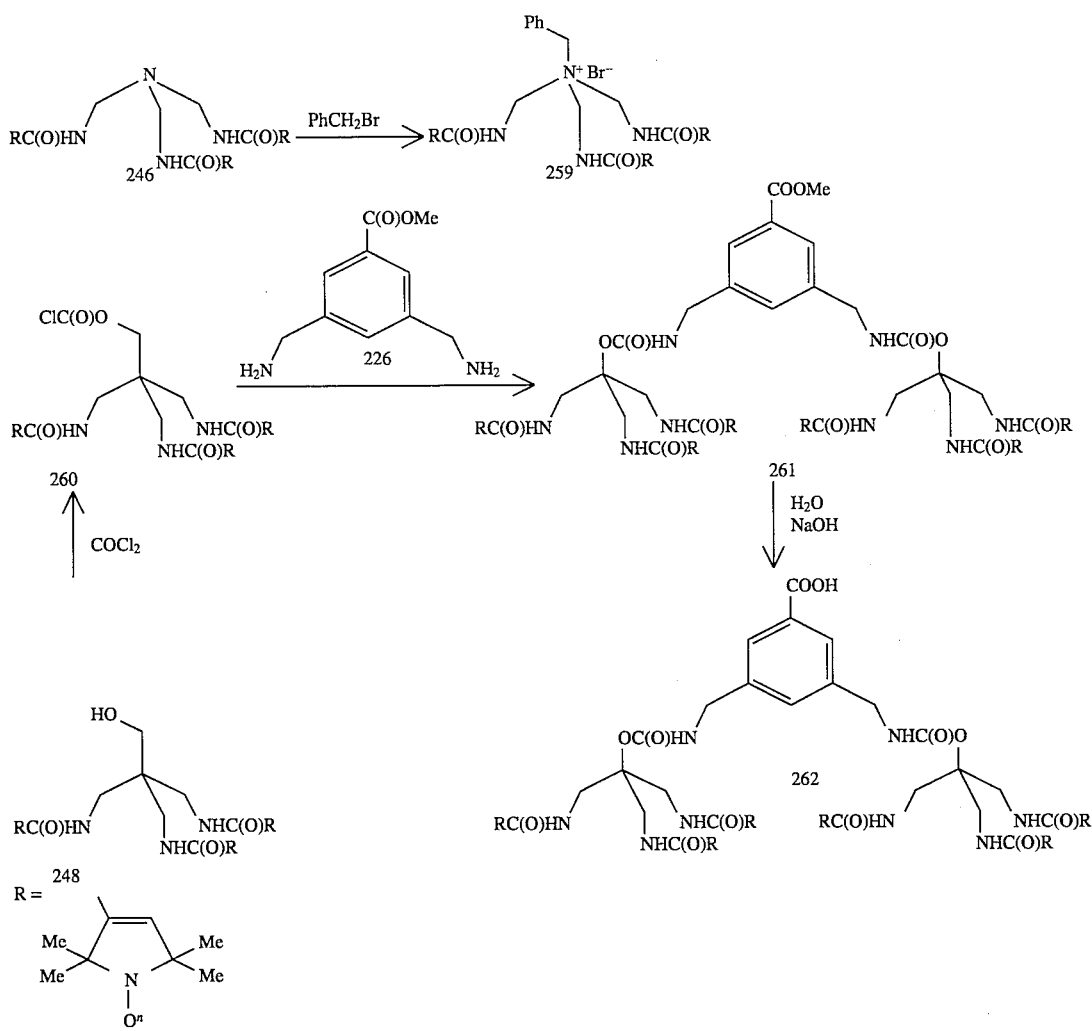

In Example 44, a mixture of the triradical 246 (0.644 g, 1mmol) and benzyl bromide (0.72 mL, 6 mmol) in MeCN (20 mL) was refluxed for 16 h, then cooled and evaporated. The residue was chromatographed on a reverse-phase column (Merck silanized silica gel RP-2; 2.5×30 cm, eluant: 30% MeOH in $H_2O$) to yield the triradical compound benzyltris[(2,2,5,5-tetramethyl-1-oxyl-3-pyrroline-4-carbonyl)aminoethyl] ammonium bromide, compound 259, 0.405 g (50% yield) as a yellow solid. Relevant data: mp 175°–177° C. (ether from MeOH); IR (KBr) 1669, 1619, 1536, 1469, 1300 and 1160 $cm^{-1}$; EPR (MeCN:ether 1:5) 7; $a_N$=14.1 G. Anal. calcd for $C_{40}H_{61}N_7O_6Br$: C, 58,89; H, 7.54; N, 12.02; Br, 9.79; found: C, 58.51; H, 7.78; N, 11.80; Br, 9.41.

In Example 45, a mixture of the triradical 268 and $Et_3N$ (1.44 mL, 10 mmol) in ether (20 mL) was added dropwise to a solution of phosgene (1.9M in toluene, 5.1 mL, 10 mmol) in ether (50 mL) at 0° C. The mixture was allowed to warm to room temperature, stirred for 7 h, then evaporated at 10° C. Dry ethyl acetate (20 mL) was added and the mixture was again evaporated to remove excess phosgene. The residue was suspended in dry ethyl acetate (25 mL). Diamine 226 (dihydrochloride, 0.133 g, 0.5 mmol) was added, followed by $Et_3N$ (0.72 mL, 5 mmol). The mixture was stirred for 16 h at 70° C., then cooled to room temperature, diluted with dry ethyl acetate (100 mL), and filtered to remove salts. The filtrate was evaporated and chromatographed on a silica gel column (2.5×25 cm, eluant: 1% MeOH in $CHCl_3$) to yield 0.530 g (71% yield) of the hexaradical ester 251 as an orange glassy solid. Relevant data: liquifies above 135° C.; IR (KBr) 1724, 1660, 1617, 1534, 1458, 1308, 1252 and 1162 $cm^{-1}$; EPR ($CHCl_3$) 9; $a_N$ =14.5. FAB MS calcd for $C_{76}H_{112}N_{14}O_{18}$+3H): 1511.8; found: 1511.8.

Example 46 was performed as follows: To a solution of the hexaradical ester 251 (0.400 g, 0.27 mmol) in MeOH (10 mL), 1N NaOH (2 mL, 2 mmol) was added. The mixture was stirred for 16 h, acidified (2N HCl) to pH 2, and extracted with $CHCl_3$ (5×20 mL). The extract was dried ($MgSO_4$) and evaporated to produce a semi-solid crude product. The product was purified by chromatography over a silica gel column (2.5 cm×20 cm) to yield 0.281 g (70% yield) of the hexaradical acid 262 as a yellow glassy solid. Relevant data: liquifies above 175° C.; IR (KBr) 1712, 1661, 1619, 1530, 1468, 1307, 1251 and 1162 $cm^{-1}$; EPR ($CHCl_3$)br. s. Anal. calcd for $C_{75}H_{110}N_{14}O_{18}$· $2H_2O$: C, 58.81; H, 7.50; N, 12.80; found: C, 58.81; H, 7.54; N, 12.70. HPLC (Resolve $C_{18}$; 0 to 60 B in 15 min): 18.9 min (99%).

EXAMPLES 47–48

In Examples 47 and 48, as illustrated in Scheme 14, we synthesized an octaradical amplifier 265 from the tetraradical acid 256. The acid 265 was activated by treatment with NHS in the presence of DCC. The resulting intermediate NHS-ester 263 was not isolated but was used in situ for acylation of the core diamine 226. The resulting methyl ester 264 was base-hydrolyzed in Example 48 to yield the corresponding acid 265. The reaction sequence as presented, including Examples 25, 40, 41, 47 and 48, illustrates amplifier synthesis by the active fragment-upgrade strategy using the starting monoradical 201 and two different types of branch groups: DETA and 3,5-bis (aminomethyl) benzoic acid.

Scheme 14
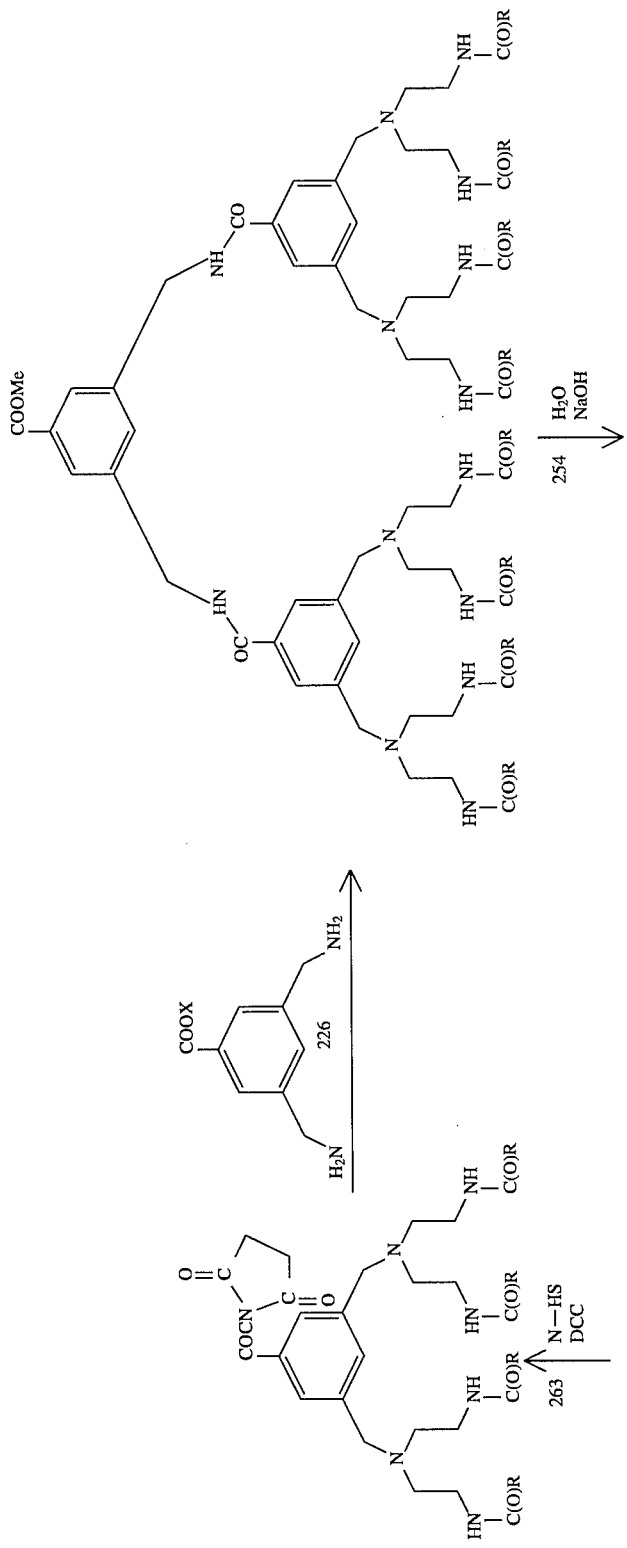

-continued
Scheme 14
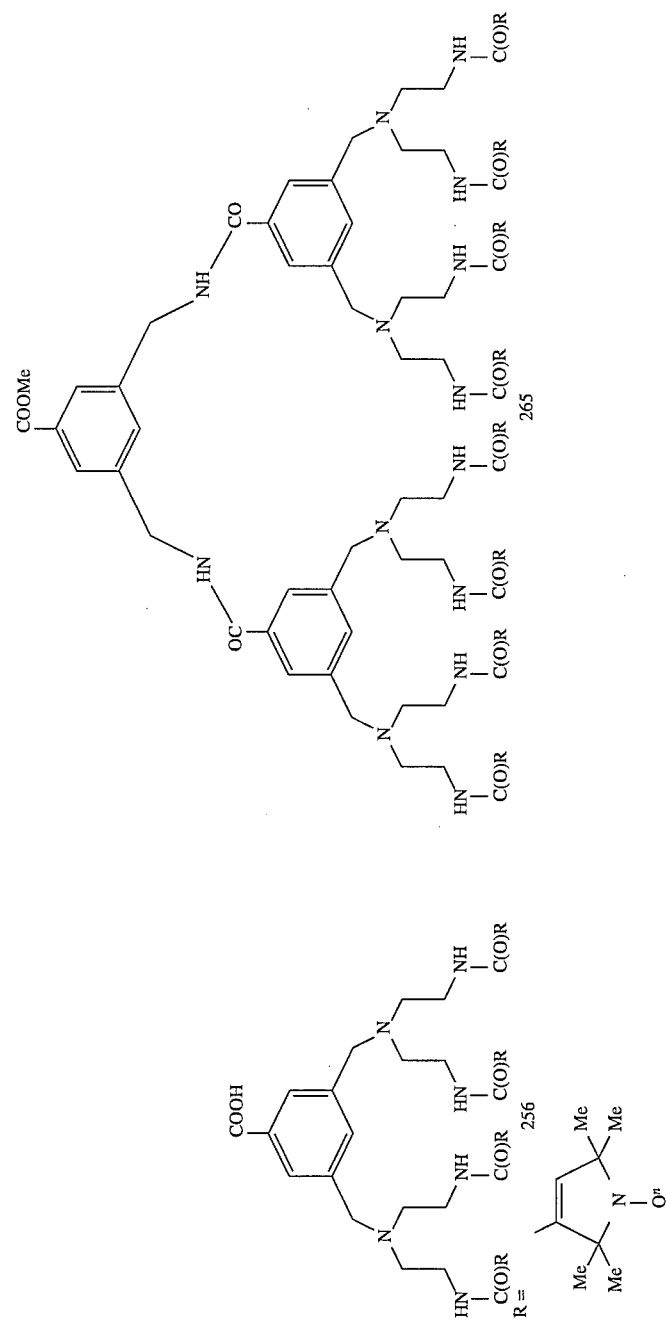

In Example 47, a mixture of the tetraradical acid 256 (1.016 g, 1 mmol), NHS (0.345 g, 3 mmol), and DCC (0.618 g, 3 mmol) in DMF (20 mL) was stirred for 8 h (TLC indicated the formation of the active ester 263). Then, diamine 226 (dihydrochloride, 0.134 g, 0.5 mmol) was added, followed by dropwise addition of Et$_3$N (0.58 mL, 4 mmol). The mixture was stirred for 40 h, then evaporated to dryness. The residue was suspended in EtOAc (100 mL), washed with H$_2$O (5×20 mL), dried (MgSO$_4$), evaporated, and chromatographed over silica gel (4×20 cm, eluant: CHCl$_3$) to yield methyl 3,5-bis-{[3',5'-bis-[2"-(2",2",5",5"-tetramethyl-1"-oxyl-3"-pyrroline-4"-carbonyl)aminoethyl]benzoylamino}methyl benzoate, compound 264, 0.558 g (51% yield) as an orange powder, solid but not crystalline. Relevant data: liquifies above 130° C.; IR (KBr): 1726, 1658, 1617, and 1539 cm$^{-1}$. Anal. calcd for C$_{116}$N$_{170}$N$_{22}$O$_{20}$: C, 63.54; H, 7.81; N, 14.05 (+4HCl+ 3H$_2$O: C, 58.97; H, 7.76; N, 13.04); found: C, 58.87; H. 7.38; N, 12.58.

(10 mL) was stirred for 16 h, then diluted with H$_2$O (20 mL), acidified (2N HCl) to pH 4.5, and extracted with CHCl$_3$ (10×10 mL). The extract was dried (MgSO$_4$) and evaporated to yield 3,5-bis-{[3',5'-bis-[2"-(2", 2", 5", 5"-tetramethyl-1"-oxyl-3"-pyrroline-4"-carbonyl)aminoethyl] benzoylamino}methyl benzoic acid, compound 265 (0.661 g, 93% yield) as a yellow powder, solid but not crystalline. Relevant data: liquifies above 175° C.; IR (KBr) 1709, 1661, 1617, and 1539 cm$^{-1}$; FAB MS calcd for (C$_{64}$H$_{90}$N$_{10}$O$_{22}$S$_2$+ H): 2179.3; found: 2179.5.

EXAMPLES 49–55

These Examples (as well as Examples 56–80) represent reactions for synthesizing amplifiers containing metal-ion (e.g., gadolinium) chelators (such as DTPA) as an active group.

To simplify the descriptions in these and subsequent Examples, the following abbreviations are used:

| Name | Drawing used | Name used |
|---|---|---|
| (benzyl-N(CH$_2$COOH)CH$_2$CH$_2$N(CH$_2$COOH)CH$_2$CH$_2$N(CH$_2$COOH)$_2$ structure with p-substituted benzyl and DTPA) | (benzyl-L structure) | benzyl(DTPA) L—H$_5$ |
| (analogous structure with COOMe esters) | (benzyl-L structure) | benzyl(pentamethyl-DTPA) L—Me$_5$ |
| (analogous structure with COONa salts) | (benzyl-L structure) | benzyl(pentasodium-DTPA) L—Na$_5$ |
| Na$_2$Gd[benzyl-DTPA complex with COO$^-$ groups] | (benzyl-L structure) | benzyl(gadolinium-disodium-DTPA) L—GDNa$_2$ |

In Example 48, a mixture of the octaradical methyl ester 264 (0.800 g, 0.365 mmol) in MeOH (20 mL) and 1N NaOH In Examples 49–54, as illustrated in Scheme 15, we synthesized the gadolinium complex 271 containing the chelating DTPA-based unit connected to an aminomethyl benzene core group. The reactions started from either a pentamethyl ester 266 or a lithium salt 272. In Example 49, the amine-pentamethyl ester 266 was activated by reaction with thiophosgene to produce the isothiocyanate derivative 267. Compound 267 was not sufficiently stable to be isolated in pure form. However, compound 267 was used in Example 50 in a reaction with the aminomethyl benzene compound 202. The resulting hexamethyl ester 268 was hydrolyzed in Example 51 with an excess of lithium hydroxide to yield a corresponding hexalithium salt 269. The same compound 269 was also obtained in Example 53 from the hydrolysis of the compound 273, which was formed in Example 52 via the reaction of the lithium salt 272 with compound In Example 54, the salt 269 was subjected to ion exchange to yield the corresponding acid 270, which was found to be unstable and was immediately converted to a gadolinium complex 271 under conditions as described in Example 54. Alternatively, salt 269 was converted into the final gadolinium complex 271 in Example 55 by treatment in solution by GdCl₃ at pH 3 followed by gradual basification to pH 10. The final compound 271 was purified by size-exclusion chromatography to remove excess inorganic material.

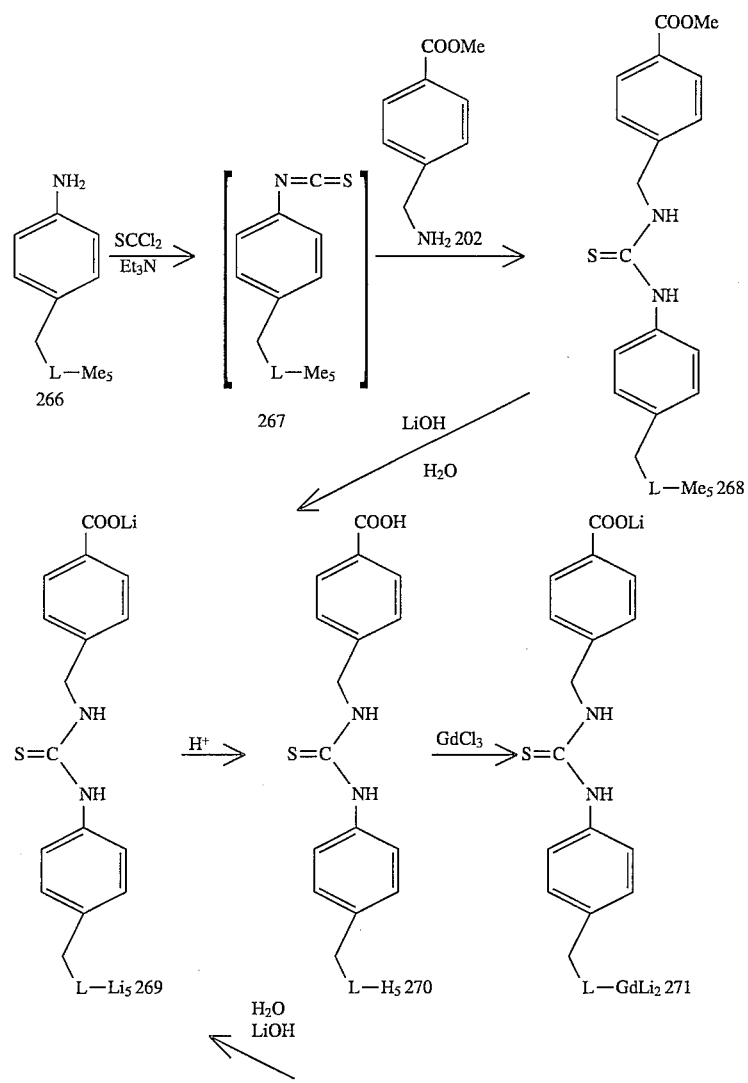

Scheme 15

-continued
Scheme 15

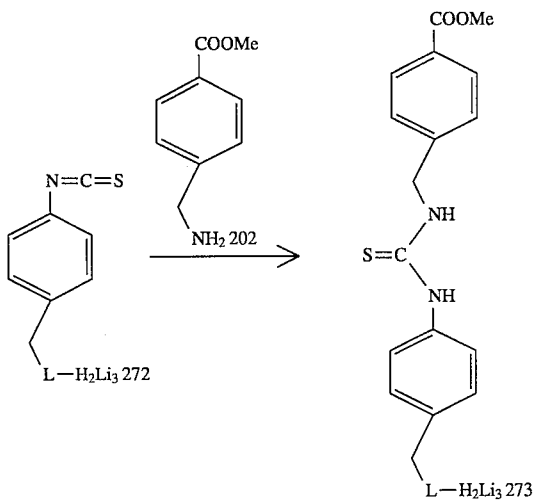

Example 49 was performed as follows: To a solution of 4-[benzyl (DTPA-pentamethyl ester)] aniline 266 (0.250 g, 0.44 mmol) in CHCl$_3$ (10 mL), CSCl$_2$ (1N in CHCl$_3$, 0.5 mL, 0.5 mmol) was added. The mixture was stirred for 2 h, then evaporated to dryness. The residual oily crude product was redissolved in CHCl$_3$ (10 mL) and evaporated again. This was repeated twice to remove excess CSCl$_2$. The resulting crude product was loaded on a silica gel column (1×30 cm) and flash chromatographed using CHCl$_3$ as an eluant, yielding 0.150 g (56% yield) [4-benzyl-(DTPA-pentamethyl ester)] isothiocyanate, compound 267, as an orange oil. Compound 267 was immediately used in the next Example.

In Example 50, a solution of isothiocyanate 267 (0.052 g, 0.085 mmol) and amine 202 (0.018 g, 0.102 mmol) in MeOH (2 mL) was stirred overnight. The mixture was evaporated, dissolved in CHCl$_3$ (2 mL), loaded on a silica gel TLC plate and chromatographed using a CHCl$_3$:MeOH (25:1) eluant to yield 0.047 g (71% yield) of N-(4-methoxycarbonyl-benzyl),N'-[4'-benzyl-(DTPA-pentamethyl ester)] thiourea, compound 268, as an orange oil. Relevant data: $^1$H NMR (CDCl$_3$) $\delta$2.55–2.80 (m, 8H), 2.90 (m, 2H), 3.13–3.70 (gr. 24H), 3.89 (s, 3H), 4.94 (br.s, 2H), 7.13 (d, 2H, J=8 Hz), 7.20 (br.s, 1H, N-H), 7.26 (d, 2H, J=8 Hz), 7.36 (d, 2H, J=8 Hz), 7.97 (d, 2H, J=8 Hz). HRMS calcd for C$_{36}$H$_{49}$N$_5$O$_{12}$S: 775.3098; found: 775.3110.

In Example 51, a mixture of methyl ester 268 (0.020 g, 0.027 mmol) and 1N LiOH (0.5 mL, 0.5 mmol) in MeOH (1 mL) was stirred for 16 h, then evaporated. The crude product was re-precipitated (acetone from MeOH) to yield 0.024 g of the hexalithium salt, lithium N-(4-carboxybenzyl),N'-[4'-methylene-(DTPA-pentalithium salt)-phenyl] thiourea, compound 269, as a white solid. Relevant data: dec. above 230° C.; IR (KBr) 1596, 1414, 1333 and 865 cm$^{-1}$; $^1$H NMR (D$_2$O) $\delta$2.60 (br. m, 8H), 2.90–3.45 (gr, 11H), 7.13 (d, 2H, J=8 Hz), 7.30 (m, overlap. d's 4H), 7.79 (d, 2H, J=9 Hz). HPLC (Resolve C$_{18}$; 20–60% B in 15 min) 11.9 min (93%).

In Example 52, a mixture of trilithium isothiocyanate 272 (0.224 g, 0.4 mmol) and amine 202 (0.088 g, 0.5 mmol) in MeOH (5 mL) was stirred for 16 h and then evaporated. The crude product was reprecipitated (acetone from MeOH) to yield 0.302 g (100% yield) of the trilithium salt N-(4-carbomethoxybenzyl),N'-[4'-methylene-(DTPA-trilithium salt)-phenyl] thiourea, compound 273, as a white solid.

Relevant data: dec. above 230° C.; IR (KBr) 1717, 1594, 1512, 1413, 1284, and 1113 cm$^{-1}$; $^1$H NMR (D$_2$O) $\delta$3.00 (m, 8H), 3.10–3.78 (gr. 10H), 3.87 (s, 3H), 4.17 (s, 4H), 7.36 (m, 4H), 7.43 (A$_2$B$_2$, J=9 Hz, 2H), 7.79 (A$_2$B$_2$, J=9 Hz, 2H).

Compound 273 was found to be unstable in storage and slowly converted to a hydrolyzed product, corresponding to 269. In water solution, hydrolysis of the methoxycarbonyl group proceeded to one-third completion in 24 h (HPLC data).

In Example 53, the trilithium compound 273 was hydrolyzed as follows: A mixture of the methyl ester 273 (0.183 g, 0.25 mmol) and 1N LiOH (2 mL, 2 mmol) in MeOH (5 mL) was stirred for 16 h and then evaporated. The crude product was re-precipitated (acetone from MeOH) to yield 0.222 g of the hexalithium salt 269, identical to that prepared in Example 51.

In Example 54, a solution of the hexasodium salt (0.240 g, 0.33 mmol), prepared under the conditions described in Example 51 but using NaOH instead of LiOH, was dissolved in H$_2$O (2 mL), and loaded on an ion-exchange column (50 mL BioRad AG 1-X4 in formate form). The column was successively eluted with H$_2$O (1 L), 1M HCOOH (0.5 L), 1.5M HCOOH, (0.5 L), 2M HCOOH (0.5 L), then 5M HCOOH. The desired compound in acid form was eluted in the last fraction (controlled by HPLC) to yield, after evaporation at 40° C., 0.116 g (0.165 mmol) of the acid 270 as a glassy yellowish solid. Compound 270 was immediately dissolved in MeOH (5 mL) and treated with GdCl$_3$. 6H$_2$O (0.061 g, 0.165 mmol) in H$_2$O (1 mL). The mixture was stirred under nitrogen for 0.5 h, then 0.1N LiOH was added dropwise to increase the pH gradually from 5.0 to 9.5 in 2 h. The mixture was stirred for 2 h, filtered to remove insoluble material, then evaporated to dryness. The residue was re-dissolved in MeOH (10 mL) and precipitated with acetone to yield 0.206 g of the crude product. The crude product was chromatographed on a Sephadex G-10 column (2.5×60 cm). The desired complex was eluted with H$_2$O in the void volume (controlled by HPLC) to yield 0.070 g (49% on acid 270 ) of lithium N-(4-carboxybenzyl),N'-[4'-methylene-(DTPA-gadolinium-trilithium salt)-phenyl] thiourea, compound 271, as a yellowish solid. Relevant data: dec. above 260° C.; IR (KBr) 1597, 1406, 1323, 1271, 1093 and 934 cm$^{-1}$; HPLC (Resolve C$_{18}$; 10 to 90% B in 15 min): 11.3 (100%). Anal. calcd for (C$_{30}$H$_{41}$N$_5$O$_{12}$SLi$_3$Gd .6H$_2$O): C, 37.08; H, 4.46; N, 7.21; found: C, 37.01; H, 4.69; N, 7.02.

In Example 55, we synthesized complex 271 from the salt 269. In a 50 mL 3-neck flask (equipped with a nitrogen inlet and a pH-microelectrode), a magnetically stirred solution of hexalithium salt 269 (0.147 g, 0.2 mmol) in 50% MeOH (20 mL) was acidified with 0.2N HCl to pH 5.5. To this, a solution of $GdCl_3 \cdot 6H_2O$ (0.074 g, 0.2 mmol) in $H_2O$ (1 mL) was added, thus lowering the pH to 3. The mixture was stirred for 0.5 h, then 0.1N LiOH was added dropwise to increase the pH gradually to 9.5 in 2 h. The mixture was stirred for 1 h, filtered to remove insoluble material, then evaporated to dryness. The residue was re-dissolved in MeOH (20 mL) and precipitated with acetone to yield the crude product which was chromatographed on a Sephadex G-10 (2.5×60 cm) column with $H_2O$ eluant to yield 0.121 g (69% yield) of the complex 271, identical to that prepared in Example 54.

EXAMPLES 56–58

These Examples are illustrated in Scheme 16. In Example 56, we exploited another representative way to activate an amino group: treatment with phosgene to produce the more reactive isocyanate, as exemplified by compound 274. Compound 274 was found to be moisture-sensitive and was used without isolation and purification. Reaction of the isocyanate 274, in solution with the amine 202 in Example 56, produced a urea derivative 275. Compound 275 was hydrolyzed in Example 57 into a corresponding sodium salt 276. Treatment of the salt 276 with $GdCl_3$ in Example 58 yielded a chelate 277.

Scheme 16

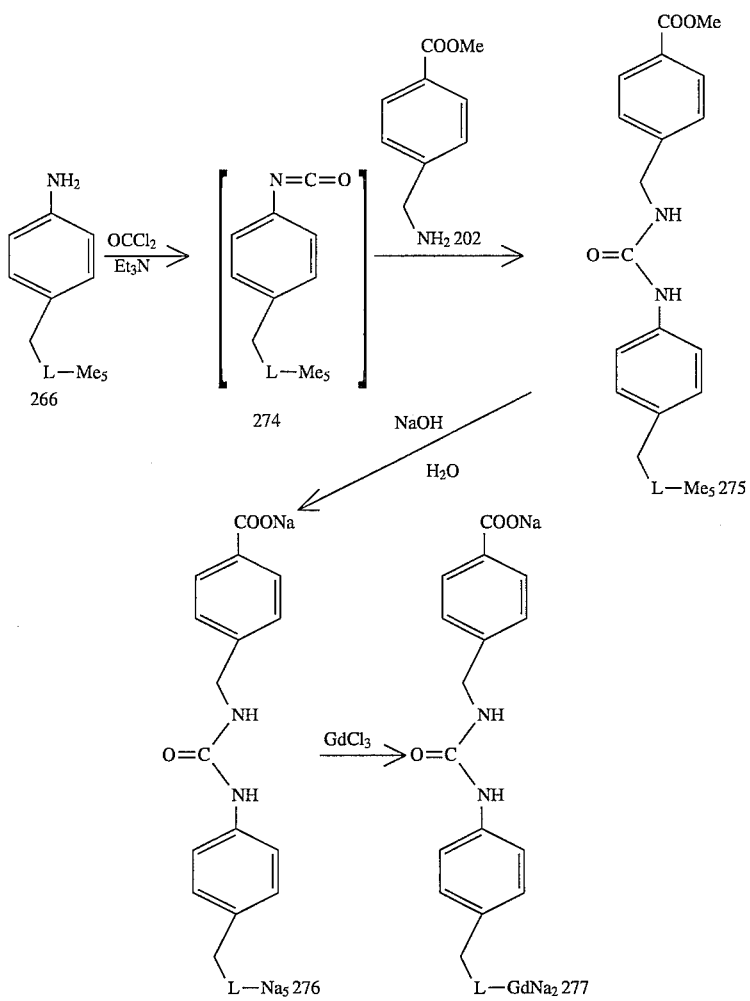

Example 56 was performed as follows: To a magnetically stirred solution of $COCl_2$ (1.9M in toluene; 3.6 mL, 7 mmol) in dry THF (20 mL) in a 3-neck flask (equipped with thermometer, dropping funnel, nitrogen inlet and outlet with low-temperature condenser, and cooled with liquid $N_2$), a solution of the amino compound 266 (0.400 g, 0.7 mmol) and $Et_3N$ (0.29 mL, 2 mmol) in THF (5 mL) was added dropwise at −10° C. The mixture was allowed to warm to room temperature, stirred for 0.5 h, then cooled to −50° C. An outlet of the flask was connected to a vacuum pump, the mixture was evaporated, and the crude isocyanate 274 was kept at 0.05 torr for 10 min at room temperature to remove excess phosgene. Dry THF (20 mL) was added through the funnel, followed by addition of the solution of amine 202 (0.246 g, 1.4 mmol) in THF (10 mL). The mixture was stirred for 4 h, then diluted with THF (50 mL), filtered to remove salts, and evaporated. The residue was chromatographed on a preparative TLC plate (40×30 cm×3 mm, eluant: 3% MeOH in $CHCl_3$) to yield 0.231 g (43% yield) of N-(4-carbomethoxybenzyl),N'-[4'-methylene-(DTPA-pentamethyl ester)-phenyl]urea, compound 275, as a yellow oil. Relevant data: IR (CCl$_4$) 1736, 1613, 1515, 1436 and 1283 cm$^{-1}$. $^1$H NMR (CDCl$_3$) δ2.58–2.80 (m, 8H), 2.93 (m, 2H), 3.37–3.70 (gr, 24H), 3.92 (s, 3H), 4.47 (d, 2H, J=6 Hz), 7.13 (d, 2H, J=8 Hz), 7.25 (d, 2H, J=8 Hz), 7.37 (d, 2H, J=8 Hz), 7.97 (d, 2H, J=8 Hz). HRMS calcd for C$_{18}$Om: 759.3327; found: 759.3320.

In Example 57, a mixture of methyl ester 275 (0.231 g, 0.30 mmol) and 1N NaOH (3 mL, 3 mmol) in MeOH (5 mL) was stirred for 4 h and then evaporated. The crude product was re-precipitated (acetone from MeOH) to yield 0.258 g of the hexasodium salt, sodium N-(4-carboxybenzyl),N'-[4'-methylene-(DTPA-pentasodium salt)phenyl]urea, compound 276, as a white solid.

Example 58 was performed as follows: In a 50-mL 3-neck flask (equipped with a nitrogen inlet and a pH-microelectrode), a magnetically stirred solution of the hexasodium salt 276 (0.220 g, 0.264 mmol) in 50% MeOH (20 mL) was acidified with 0.2N HCl to pH 6.5. To this, a solution of GdCl$_3$.6H$_2$O (0.104 g, 0.28 mmol) in H$_2$O (1 mL) was added, causing the pH to drop to 3.2. The mixture was stirred for 0.5 h, then 0.1N NaOH was added dropwise to gradually increase the pH to 10 in 1 h. The mixture was stirred for 1 h, filtered to remove insoluble material, then evaporated to dryness. The residue was re-dissolved in MeOH (20 mL) and precipitated with acetone to yield 0.280 g of a crude product. Subsequent purification of the product on a Sephadex G-25 column, (2.5×50 cm, eluant: H$_2$O) yielded, after re-precipitation with acetone from MeOH, 0.187 g (74% yield) of sodium N-(4-carboxybenzyl),N'-[4,-methylene-(DTPA-gadolinium-disodium salt)-phenyl] urea, compound 277, as a white solid. Relevant data: dec. above 300° C.; IR (KBr) 1600, 1554, 1515, 1402, 1320, 1241, 1094 and 933 cm$^{-1}$. HPLC (Resolve C$_{18}$; 10 to 90% B in 15 min): 10.9 min (98%). Anal. calcd for (C$_{30}$H$_{31}$N$_5$O$_{13}$Na$_3$Gd. 6H$_2$O): C, 35.89; H, 4.32; N, 6.98; found: C, 35.50; H, 4.65; N, 6.71.

EXAMPLES 59–63

These Examples are illustrated in Scheme 17. A reaction of the DTPA-pentamethyl ester 267 (Example 49) with the core molecule 226 in Example 59 produced the desired compound 279 (containing two thiourea linkages), but in low yield. We then decided to form the thiourea linkages in a reverse way. In Example 60, the core group 226 was "activated" by reaction with the thiophosgene to form a diisothiocyanate 278 which was found to be stable and isolatable in pure form. Reaction of compound 278 and amine 266 in Example 61 yielded compound 279, which was subjected to a basic hydrolysis in Example 62 to produce a corresponding sodium salt 280. Complexation of the salt with Gd(III) ion in water solution in Example 63 resulted in the formation of the bis-gadolinium complex 281.

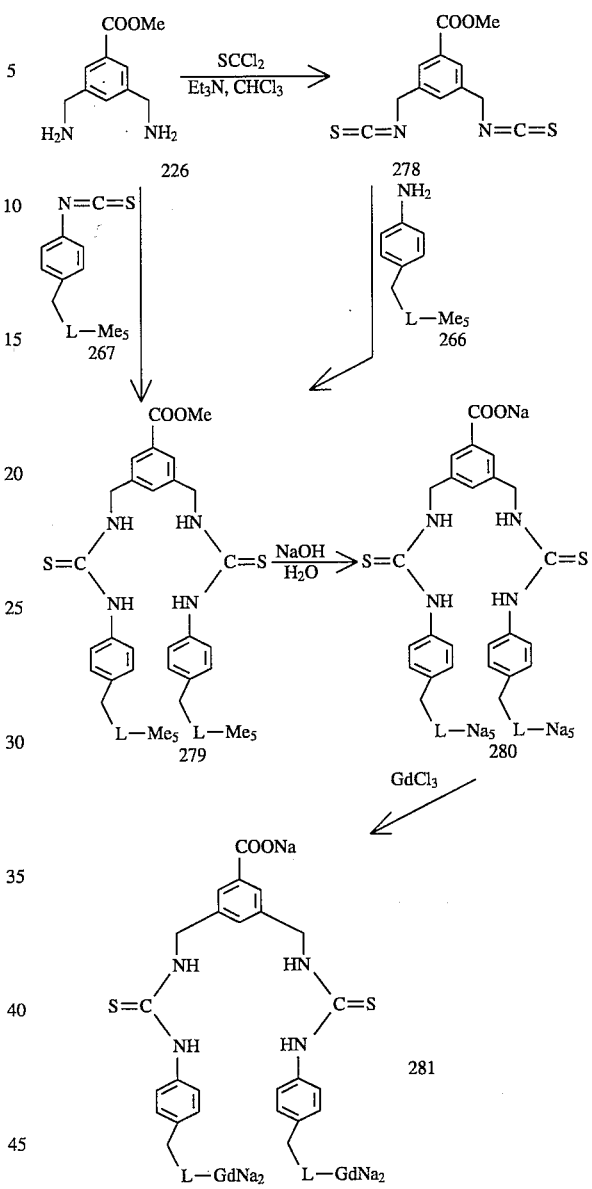

Scheme 17

In Example 59, the reaction of isothiocyanate 267 with diamine 226 was conducted as follows: To a solution of isothiocyanate 267, prepared under the conditions described in Example 49 from amine 266 (0.284 g, 0.5 mmol) in ethanol-free CHCl$_3$ (20 mL), a mixture of diamine 226 (dihydrochloride, 0.067 g, 0.25 mmol) and Et$_3$N (0.14 mL, 1 mmol) was added. The mixture was stirred for 16 h, diluted with CHCl$_3$ (50 mL), washed with H$_2$O (3×20 mL), dried (MgSO$_4$), and evaporated. The residue was chromatographed on a silica gel column (1.5×20 cm) to yield 0.010 g (3% yield) of the compound 279 as a red glassy solid. Relevant data: liquifies above 65° C.; $^1$H NMR (CDCl$_3$) δ2.53–2.83 (m, 16H), 2.83–3.11 (m, 4H), 3.40–3.80 (gr, 48H), 3.88 (s, 3H), 4.91 (d, J=6 Hz, 4H), 7.24 (A$_2$B$_2$, 8H, J=8 Hz), 7.55 (s, 1H), 7.80 (s, 2H). FAB MS calcd for (C$_{64}$H$_{90}$N$_{10}$O$_{22}$S$_2$+H): 1415.6; found: 1415.6.

Example 60 was performed as follows: To a vigorously stirred mixture of diamine 226 (dihydrochloride, 0.267 g, 1 mmol) and SCCl$_2$ (1M in CHCl$_3$, 5 mL, 5 mmol) in ethanol-free CHCl$_3$ (10 mL), Et$_3$N (0.7 mL, 5 mmol) was added dropwise at −20° C. The mixture was stirred for 30 min, diluted with CHCl₃ (20 mL), then sequentially washed with 1N HCl (2×10 mL), H₂O (2×10 mL), and saturated NaHCO₃ (20 ml). The mixture was then dried (MgSO₄) and evaporated. The oily residue was chromatographed over a silica gel column (1×40 cm, eluant: CHCl₃) to yield 0.195 g (71% yield) of methyl (3,5-bis-isothiocyanatomethyl) benzoate, compound 278, as a yellow solid. Relevant data: mp 77°–79° C. (from hexane:EtOAc 5:1); IR (KBr) 2193, 2174, 2097, 1722 and 1223 cm⁻¹; ¹H NMR (CDCl₃) δ3.95 (s, 3H), 4.82 (3, 4H), 7.49 (s, 1H,), 7.97 (s, 2H,); ¹³C NMR (CDCl₃) δ48.21, 52.49, 127.94 (2C), 129.41 (1C), 131.81 (1C), 134.40 (br, 1C, C=S), 135.87 (2C), 165.75 (1C, C=O). Anal. calcd for C₁₂H₁₀N₂O₂S₂: C, 51.78; H, 3.62; N 10.06; found: C, 52.11; H, 3.52; N 9.94.

In Example 61, a solution of the amine 266 (0.057 g, 0.1 mmol) and the diisocyanate 278 (0.013 g, 0.05 mmol) in ethanol-free CHCl₃ was stirred for 18 h and then evaporated. The crude product was purified on preparative TLC (eluant: 3% MeOH in CHCl₃) to yield 0.049 g (70% yield) of the bis-pentamethyl ester, compound 279, identical to that prepared in Example 59.

Example 62 pertained to the base hydrolysis of the compound 279. A mixture of methyl ester 279 (0.250 g, 0.18 mmol) and 1N NaOH (4 mL, 4 mmol) in MeOH (5 mL) was stirred for 16 h and then evaporated. The crude product was re-precipitated (acetone from MeOH) to yield 0.291 g of the sodium salt 280 as a yellowish solid. Relevant data: dec. above 250° C.; IR (KBr) 1591, 1437, 1329, 1187, 1109 and 880 cm⁻¹. ¹H NMR (D₂O) δ2.66 (m, 16H), 2.80–3.50 (gr, 22H), 7.22 (d, 4H, J=6 Hz), 7.32 (d, 4H, J=6 Hz), 7.36 (s, 1H), 7.64 (s, 2H). HPLC (Resolve C₁₈; 10 to 90% B in 15 min): 12.2 (96%).

Example 63 was performed as follows: In a 50-mL 3-neck flask (equipped with a nitrogen inlet and a pH-microelectrode), a magnetically stirred solution of the sodium salt 280 (0.177 g, 0.12 mmol) in 50% MeOH (20 mL) was adjusted with 0.2N HCl to pH 7.0. To this, a solution of GdCl₃·6H₂O (0.093 g, 0.25 mmol) in H₂O (1 mL) was added (pH dropped to 2.4). The mixture was stirred for 0.5 h, then 0.1N NaOH was added dropwise to gradually increase the pH to 10 in 1 h. The mixture was stirred for 1 h, filtered to remove insoluble material, and then evaporated to dryness, thereby yielding the crude product. The crude product was purified on a Sephadex G-25 column (2.5×80 cm, eluant: H₂O) to yield (after re-precipitation with acetone from MeOH) 0.133 g (66% yield) of the digadolinium complex, compound 281, as a white solid. Relevant data: dec. above 300° C.; IR (KBr) 1601, 1405, 1319, 1264, 1093, 1018 and 931 cm⁻¹. HPLC (Resolve C₁₈; 10 to 90% B in 15 min): 12.0 min (98%). Anal. calcd for C₅₃H₅₇N₁₀O₂₂S₂Gd₂Na₅·14H₂O : C, 32.95; H, 4.43; N, 7.25; found: C, 33.26; H, 4.07; N, 7.01.

The relaxivity "R₁" values of compound 281 were studied and compared to relaxivity values for monochelates 271 and 277. None of the three compounds tested (i.e., compounds 271, 277, and 281) exhibited any detectable levels of free gadolinium (i.e., levels greater than 0.03 mM). Compounds 271 and 277, exhibited relaxivity values that were consistent with the conventional MRI contrast-enhancing agent Gd-DPTA in water (i.e., R₁=4 to 4.5 mmol⁻¹.sec⁻¹). The dichelate, compound 281, exhibited greater than twice the relaxivity than either of compounds 271 or 277 (FIG. 1).

Figure 2:
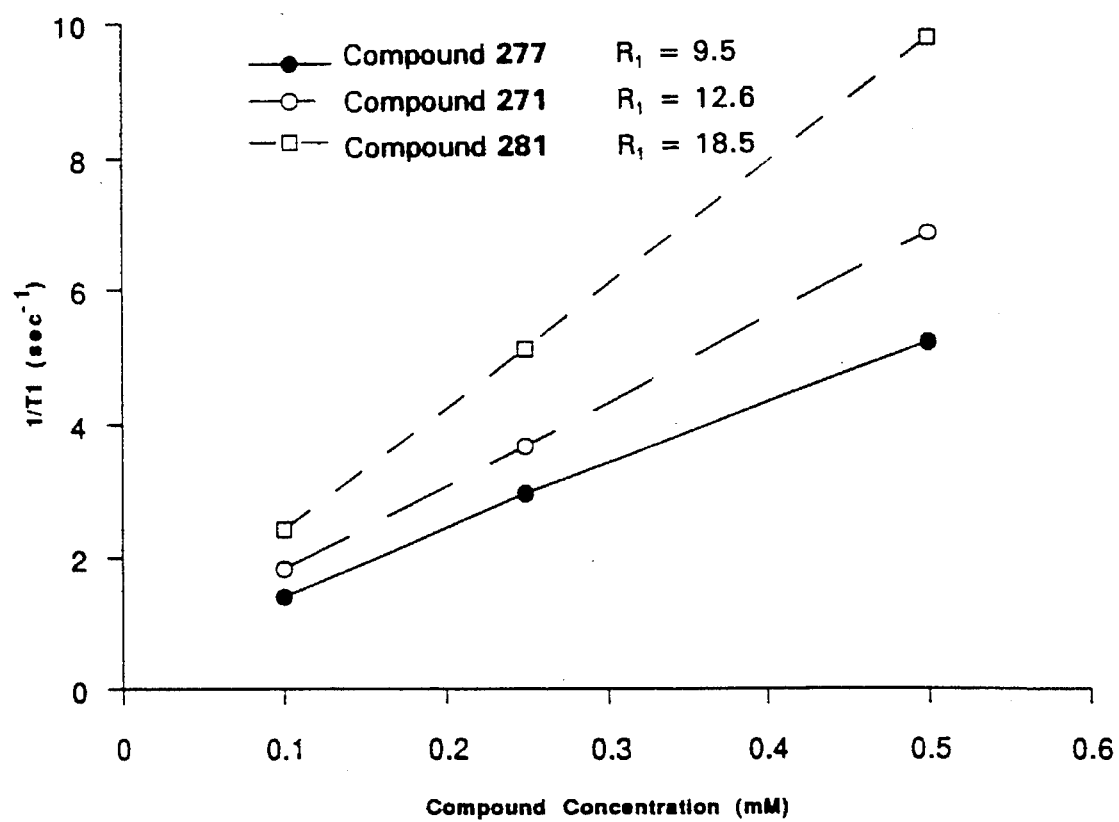
FIG. 2 is a plot of the increased relaxivity in a BSA solution exhibited by each of compounds 281, 271, and 277, as discussed in Examples 59–63.

Compounds 271, 277, and 281 exhibited increased relaxivity in an aqueous solution of 4% bovine serum albumin (BSA), ranging from 9.5 to 18.5 mmol⁻¹.sec⁻¹ (FIG. 2). Gd-DPTA did not exhibit a significant increase in relaxivity when transferred from water to 4% BSA. (A certain amount of protein binding to the tested compounds may have occurred in the BSA solution which may be advantageous.)

EXAMPLES 64–65

We found that, in the case of DTPA-based chelating amplifiers, the core-upgrade strategy was preferable over the active group-upgrade strategy for constructing amplifiers having higher amplification levels. This is because the relatively labile protected active group (e.g., pentamethyl DTPA ester) can be introduced at a later step. To exemplify this approach, these Examples, illustrated in Scheme 18, illustrate how certain branch groups can be linked to core groups.

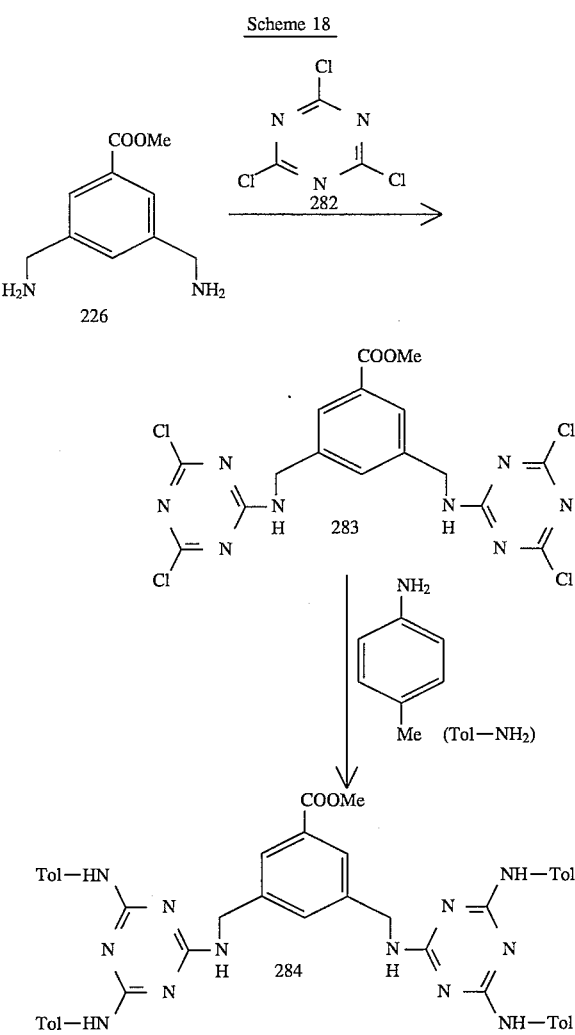

Scheme 18

In Example 64 we connected the triazine branch group 282 to the core molecule 226 to produce the bistriazine derivative 283 having four chlorine atoms each capable of nucleophilic substitution. Nucleophilic substitution was demonstrated in Example 65 involving a reaction of compound 283 with the model aromatic amine, p-toluidine, which proceeded with replacement of all the chlorine atoms by toluidine residues to yield tetrakis(toluidine), compound 284.

Example 64 was performed as follows: To a stirred mixture of cyanuric chloride 282 (0.552 g, 3 mmol) and K₂CO₃ in MeCN (20 mL), a mixture of diamine 226

(dihydrochloride, 0.267 g, 1 mmol) and $Et_3N$ (0.29 mL, 2 mmol) in MeCN (1 mL) was added. The mixture was stirred for 5 h, filtered from salts, and evaporated. The residue was chromatographed on a silica gel column (1.5×50 cm, eluant: $CHCl_3$) to yield 0.111 g (22% yield) of 1,3-bis- [N- (4, '6'-dichloro-s-triasinyl-2')aminomethyl]-5-methoxycarbonyl benzene, compound 283, as a white crystalline solid. Relevant data: mp 136°–137° C. (from $CHCl_3$); IR (KBr) 1724, 1607, 1550, 1512, 1240, 1168 and 1101 $cm^{-1}$; $^1H$ NMR ($CDCl_3$) δ3.96 (s, 3H), 4.77 (d, 4H, J=6 Hz), 6.05 (br, 2H, N-H), 7.50 (s, 1H), 7.96 (s, 2H). HRMS calcd for $C_{16}H_{12}N_8O_2Cl_4$: 487. 9837; found: 487.9817.

Example 65 pertained to the reaction of the compound 283 with p-toluidine, as follows: The mixture of the triazine derivative 283 (0.023 g, 0.05 mmol), p-toluidine (0. 053 g, 0.5 mmol) and $K_2CO_3$ (0. 138 g, 1 mmol) in MeCN (5 mL) was refluxed for 10 days, cooled to room temperature, then filtered to remove salts. The filtrate was evaporated and the crude product was purified using preparative TLC (eluant: $CHCl_3$) to yield 0.027 g (70% yield) of the tetratoluidine derivative 284 as a yellow solid. Relevant data: mp 148°–150° C. (from hexane:benzene 1:1); $^1H$ NMR ($CDCl_3$) δ2.72 (s, 12H), 3.81 (s, 3H), 4.47 (d, 4H, J=6 Hz), 6.11 (br, 2H, N-H), 7.04 (d, 8H, J=18 Hz, 8H), 7.10 (s, 1H), 7.35 (d, 8H, J=18 Hz), 8.72 (s, 2H). HR FAB MS calcd for ($C_{44}H_{45}N_{12}O_2$+H): 773.3788; found: 773.3804.

EXAMPLES 66–70

These Examples are illustrated in Scheme 19. In Examples 66–69 we prepared tetraisothiocyanate 290 as an example of another polyfunctional molecule capable of reacting with aromatic amines. Compound 290 is a key intermediate in the synthesis of certain amplifiers according to the present invention. The synthesis of compound 290 was accomplished using commercial nitro-m-xylene 285 and bis-(phthalimido-protected) DETA (compound 287), prepared from DETA and (carboxyethyl) phthalimide (Nefken's reagent). Starting compound 285, upon bromination with NBS in Example 66, produced a bis-(bromomethyl) derivative 286, which was reacted with bis-(phthalimido-protected) DETA 287 in Example 67 to yield a phthalimido-protected tetraamine 288. Compound 288 was de-protected in Example 68 using anhydrous hydrazine in absolute ethanol to produce the tetraamine 289 isolated in the form of a hydrochloride salt. In Example 69, treatment of this salt with excess thiophosgene in a two-phase $CHCl_3$/$H_2O$ system yielded the tetraisothiocyanate 290. A model reaction using excess p-toluidine in Example 70 yielded the tetraaddition product 29.

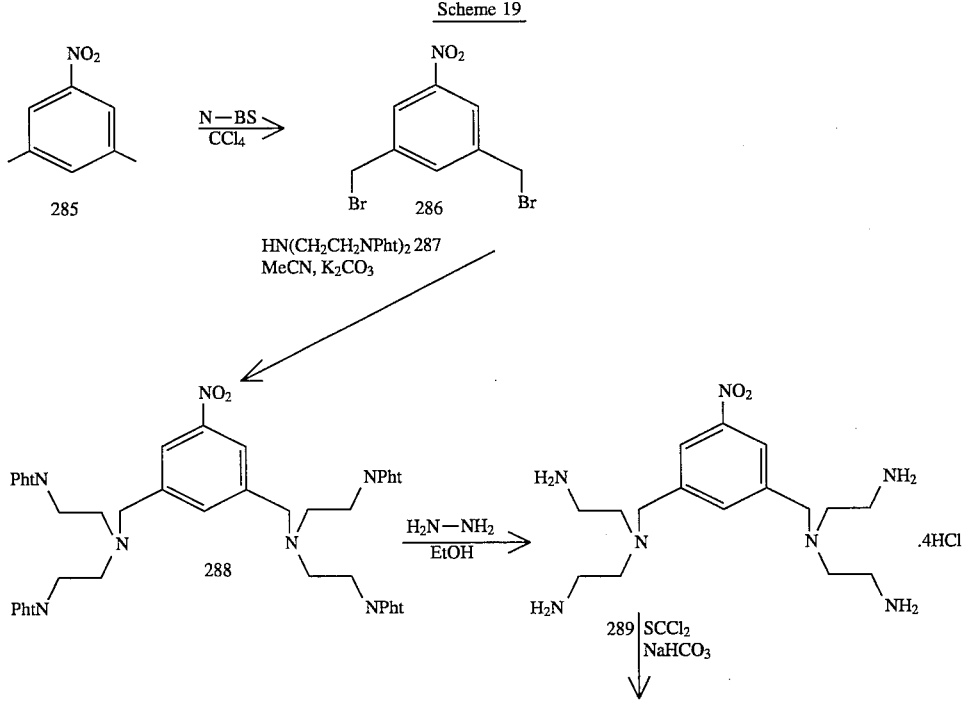

Scheme 19

Scheme 19 -continued

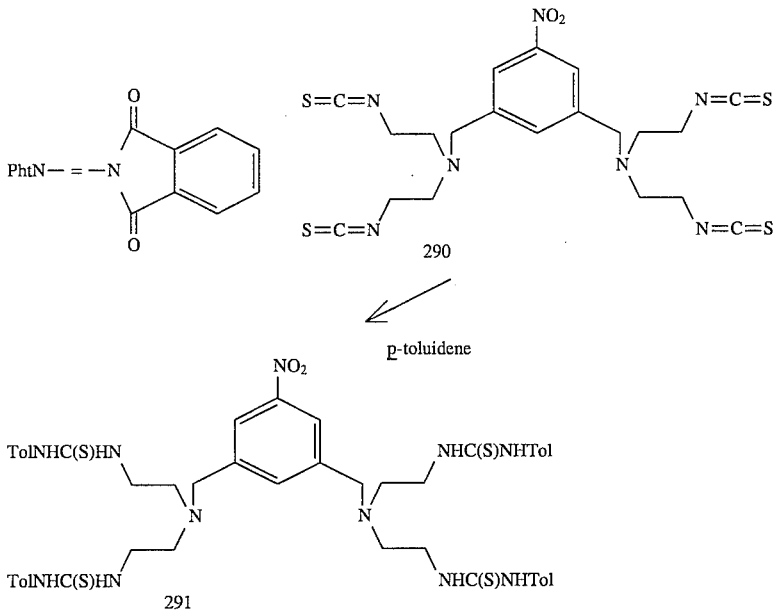

In Example 66, a mixture of 5-nitro-m-xylene 285 (3.02 g, 20 mmol), NBS (7.12 g, 40 mmol), and benzoyl peroxide (10 mg) in $CCl_4$ (50 mL) was refluxed for 16 h. The precipitated succinimide was removed by filtration and washed with $CCl_4$ (3×20 mL). The combined filtrates were evaporated. The solid residue was recrystallized from a hexane:EtOAc (3:1) mixture to yield 3.28 g (53% yield) of 1,3-bis- (bromomethyl) -5-nitro benzene, compound 286, as colorless crystals. Relevant data: mp 100°–101° C. (from hexane:EtOAc 1:10); IR (KBr) 1540, 1362 and 1215 $cm^{-1}$; $^1H$ NMR ($CDCl_3$) δ4.52 (s, 4H), 7.75 (s, 1H), 8.19 (s, 2H); $^{13}C$ NMR ($CDCl_3$) δ30.55, 123.66, 135.16, 140.40, 148.61. HRMS calcd for $C_8H_7NO_2{}^{79}Br_2$: 306. 8844; found: 306. 8840.

In Example 67, a mixture of dibromide 286 (1.98 g, 6.4 mmol), bis-(phthalimido-protected) DETA 287 (5.59 g, 15.4 mmol) and $K_2CO_3$ (3.45 g, 25 mmol) in MeCN (100 mL) was refluxed with vigorous stirring for 4 days. Inorganic material was removed by filtration. The precipitate was washed with MeCN (4×20 mL). The combined filtrates were evaporated. The residue was chromatographed over a silica gel column (2.5×30 cm) to yield 2.34 g (42% yield) of the protected tetraamine, 1,3-bis-[N,N-bis(N'-phthalimidoethyl-2)] aminomethyl-5-nitro benzene, compound 288, as a white powder. Relevant data: mp 156°–158° C. (from hexane:EtOAc 1:5); IR (KBr) 1730, 1539, 1360 and 1211 $cm^{-1}$; $^1H$ NMR ($CDCl_3$) δ2.78 (t, 8H, J=5.5 Hz), 3.51 (s, 4H), 3.73 (t, 8H, J=5.5 Hz), 7.28 (s, 1H), 7.64 (s, 2H), 7.68 (br.s, 16H); $^{13}C$ NMR (DMSO-$d_6$) δ35.80 (4C), 51.73 (4C), 56.82 (2C), 122.56 (1C), 123.39 (8C), 132.28 (8C), 134.83 (8C), 141.70 (1C), 147.98 (1C), 168.31 (8C). HR FAB MS calcd for ($C_{48}H_{40}N_7O_{10}$+H): 847.2836; found: 874. 2823.

Example 68 was performed as follows: To a boiling suspension of compound 288 (0.90 g, 1.03 mmol) in absolute EtOH (250 mL), hydrazine (2.5 mL, 77 mmol) was added with vigorous stirring. After about 10 min the mixture became a clear solution. After refluxing for an additional 10 min, the solution was cooled to room temperature and evaporated to dryness. The residue was evaporated twice with EtOH (30 mL) and evacuated to 0.1 Torr to remove excess hydrazine. The solid was suspended in 2N HCl (50 mL), stirred for 1 h, and filtered to remove insoluble phthalimidohydrazine. The filtrate was extracted with $CHCl_3$ (3×30 mL, discarded) and evaporated to dryness to produce a hygroscopic crude product. Crystallization of the product from MeOH yielded 0.39 g (66% yield) of 1,3-bis-[N,N-bis(2-aminoethyl)]aminomethyl-5-nitro benzene, compound 289, as a yellow powder. Relevant data: mp 256°–258° C. (from MeOH); IR (KBr) 1539, 1360 and 1211 $cm^{-1}$; $^1H$ NMR (D20) δ2.90 (t, 8H, J=6.1 Hz), 3.18 (t, 8H, J=6.1 Hz), 3.94 (s, 4H), 7.76 (s, 1H), 8.25 (s, 2H); $^{13}C$ NMR ($D_2O$) δ36.41 (4C), 50.74 (4C), 57.65 (2C), 125.80 (2C), 137.50 (2C), 138.65 (1C), 149.50 (1C). Anal. calcd for $C_{16}H_{31}N_7O_2$. 4HCl: C, 33.58; H, 6.52; N, 17.13; found: C, 33.58; H, 6.84; N, 17.14.

Example 69 was performed as follows: To a vigorously stirred mixture of $NaHCO_3$ (4.000 g, 40 mmol) and thiophosgene (1N in $CHCl_3$, 2 mL, 2 mmol) in $CHCl_3$ (50 mL), a solution of tetraamine hexahydrochloride 289 (0.089 g, 0.16 mmol) in $H_2O$ (1 mL) was introduced. The mixture was stirred for 6 h, then $MgSO_4$ (10 g) was added to remove water. The inorganic material was removed by filtration and washed with $CHCl_3$ (5×10 mL). The combined filtrates were evaporated and the oily residue was chromatographed on a silica gel TLC plate (eluant: $CHCl_3$) to yield 0.045 g (56% yield) of 1,3-bis-[N,N-bis-(2-isothiocyanatoethyl)] aminomethyl-5-nitro benzene, compound 290, as a yellow solid. Relevant data: mp 62°–64° C. (from hexane); IR (KBr) 2212, 2129, 2063, 1528, 1440 and 1343 $cm^{-1}$; $^1H$ NMR ($CDCl_3$) δ2.97 (t, 8H, J=6.0 Hz), 3.62 (t, 8H, J=6.0 Hz), 3.89 (s, 4H), 7.93 (s, 1H), 8.11 (s, 2H); $^{13}C$ NMR ($CDCl_1$) d 44.31 (4C), 54.55 (4C), 58.69 (2C), 123.10 (1C), 133.16 (br.s, 1C, C=S), 135.44 (1C), 141.75 (2C), 149.16 (1C). Anal. calcd for $C_{20}H_{23}N_7O_2S_4$: C, 46.05; H, 4.44; N, 18.79; S, 24.58; found: C, 45.85; H, 4.30; N, 18.47; S, 24.56.

Example 70 pertained to a reaction of compound 290 with p-toluidine, as follows: A mixture of the tetraisothiocyanate 290 (0.010 g, 0.02 mmol) and p-toluidine (0.011 g, 0.1 mmol) in $CHCl_3$ (3 mL) was stirred for 16 h, then evaporated. The crude product was purified using preparative TLC (eluant: CHCl$_3$) to produce 0.017 g (90% yield) of the tetratoluidine derivative 291as a yellow solid. Relevant data: mp 148°–150° C. (hexane from EtOAc); $^1$H NMR (CDCl$_3$) δ2.31 (s, 12H), 2.71 (br, 8H), 3.65 (br, 12H), 6.66 (br, 4H, N-H), 7.13 (A$_2$B$_2$, 16H, J=8 Hz), 7.47 (s, 1H), 7,81 (br, 4H, N-H), 8.01 (s, 2H); $^{13}$C NMR (CDCl$_3$) δ20.97, 42.91, 53.35, 58.43, 122.41, 125.11 (4C), 130.36 (4C), 133.90 (4C), 135.10, 136.98 (4C), 141.2, 148.59, 180.99 (4C, C=S). HR FAB MS calcd for (C$_{48}$H$_{59}$N$_{11}$O$_2$S$_4$+H): 950.3814; found: 950.3860.

EXAMPLES 71–73

These Examples are illustrated in Scheme 20. In Example 71 we connected four protected chelating units to the active terminals of compound 290 to produce compound 292. (For further simplification, R-substituted amplifiers containing four DTPA units are abbreviated as R-4 (L-X) wherein R is equal to R$_1$; and X represents substituents on DTPA carboxyls. The complete structure of compound 292 is shown in Scheme 21.) The protected methyl groups on compound 292 were removed by basic hydrolysis as described in Example 72 to yield the sodium salt 293, which was converted in Example 73 into the tetragadolinium complex 294 by treatment with Gd(III), followed by size-exclusion chromatography.

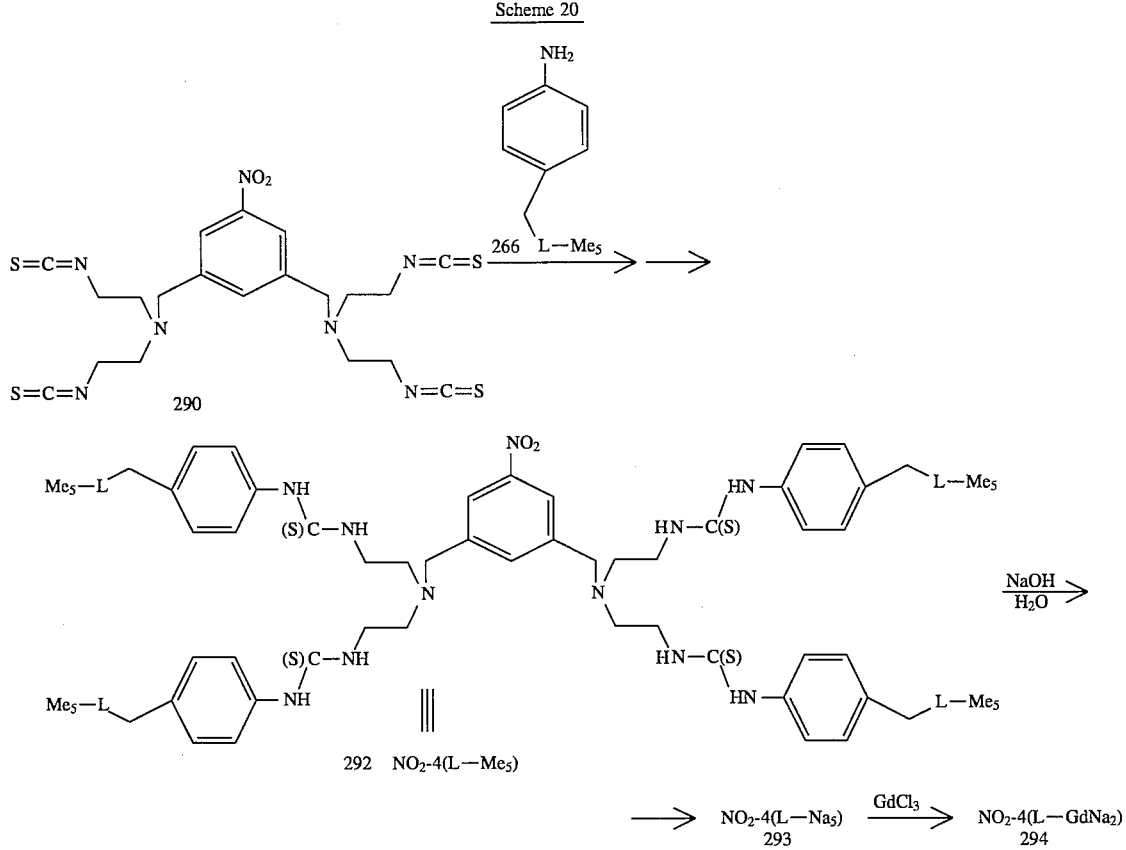

Scheme 20

Scheme 21

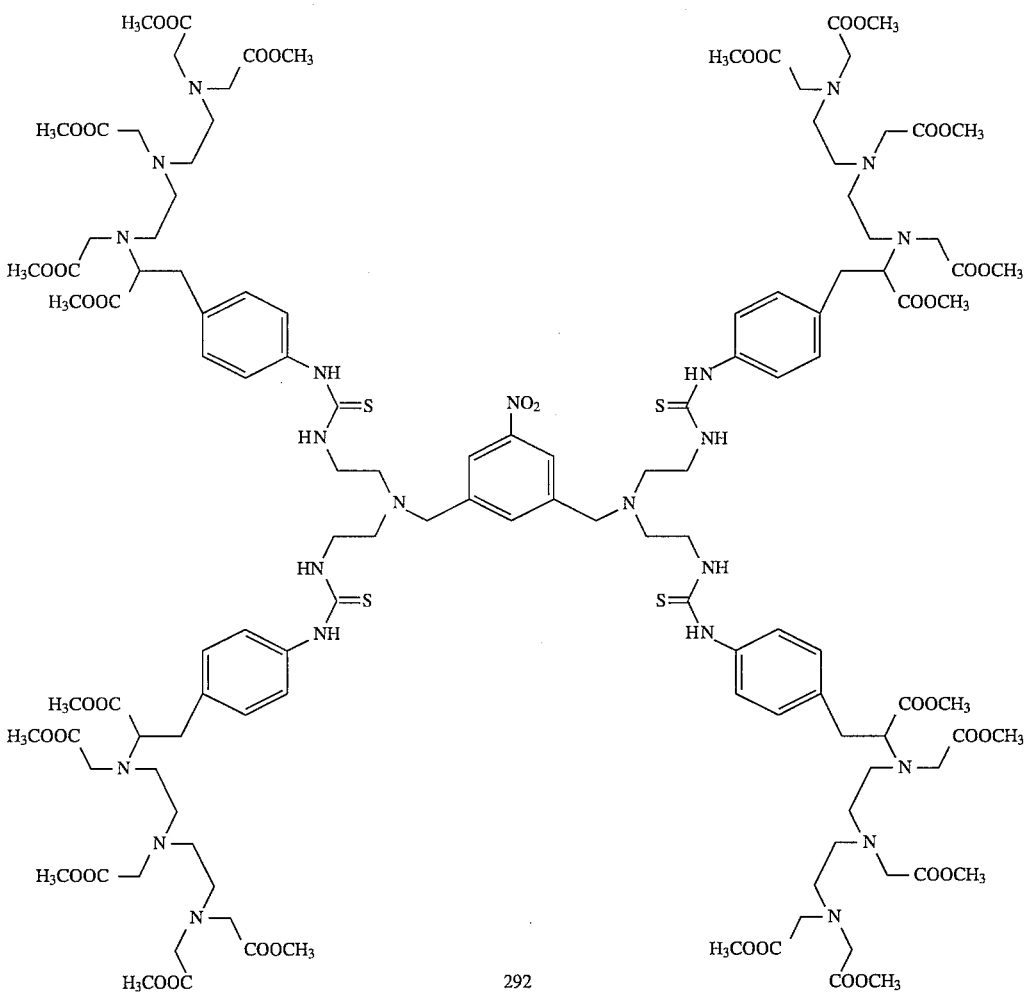

292

Example 71, pertaining to the reaction of tetraisocyanate 290 with amine 266, was performed as follows: A mixture of tetraisothiocyanate 290 (0.057 g, 0.11 mmol) and amine 266 (0.270 g, 0.48 mol) in CHCl$_3$ (3 mL) was stirred for 10 days at 50° C., then evaporated and purified on a TLC plate (30×40 cm×3 mm, eluant: MeOH in CHCl$_3$) to produce 0.201 g (65% yield) of the compound 292 as a yellow glassy solid. Relevant data: liquifies above 70° C.; IR (KBr) 1735, 1538, 1515, 1202 and 1028 cm$^{-1}$; $^1$H NMR (DMSO-D$_6$+5% D$_2$O) δ7.03 (d, 8H, J=7 Hz), 7.29 (d, 8H, J=7 Hz), 7.79 (s, 1H), 7.95 (s, 2H); $^1$H NMR (CDCl$_3$+2% D$_2$O) δ2.40–3.20 (gr, 40H), 3.30–3.80 (gr, 116H), 7.11–7.24 (br.m, 8H), 7.27–7.40 (br.m, 9H), 7.93 (s, 2H).

Example 72, pertaining to the hydrolysis of the compound 299, was performed as follows: A mixture of compound 292 (0.110 g, 0.04 mmol) and 1N NaOH (2 mL, 2 mmol) in MeOH (5 mL) was stirred at 45° C. for 23 h, cooled to room temperature, then evaporated. The resulting crude product was re-precipitated with acetone from methanol to yield 0.119 g of compound 293 as a yellowish solid. Relevant data: dec. above 250° C.; IR (KBr) 1598, 1541, 1411, 1332, and 1116 cm$^{-1}$; $^1$H NMR (D$_2$O) δ2.18 (m, 8H), 2.61 (m, 8H), 2.68 (m, 32H), 2.70–3.82 (gr, 48H), 7.08 (d, 8H, J=6 Hz), 7.25 (d, 8H, J=6 Hz), 7.72 (s, 1H), 8.14 (s, 2H). HPLC (Microsorb C$_{18}$; 20 to 95% B in 20 min): 14.4 min (95%).

Example 73, pertaining to the synthesis of the tetragadolinium complex 294, was performed as follows: In a 50 mL 3-neck flask (equipped with a nitrogen inlet and a pH-microelectrode), a magnetically stirred solution of sodium salt 293 (0.120 g, 0.042 mmol) in water (12 mL) was acidified (0.2N HCl) to pH 6.5. GdCl$_3$. 6H$_2$O (0.079 g, 0.21 mmol) in H$_2$O was added (pH dropped to 2.5). The mixture was stirred for 15 min and the pH was gradually increased to 9.5 in 2 h by dropwise addition of 0.1N NaOH. The mixture was stirred for 0.5 h and centrifuged. The supernatant was filtered through a 0.45-μm membrane filter and evaporated to produce 0.151 g of a crude residue. The residue was purified on a Sephadex G-25 column (2.5×80 cm) to yield 0.061 mg (44% yield) of the complex 294 as a yellow glassy powder. Relevant data: dec. above 250° C.; IR (KBr) 1598, 1404, 1321 and 1097 cm$^{-1}$. HPLC (Microsorb C$_{18}$; 20 to 95% B in 20 min): 14.5 min (94%). Anal. calcd for C$_{104}$H$_{123}$N$_{23}$O$_{42}$S$_4$Gd$_4$Na$_8$.16H$_2$O: C, 34.73; H, 4.34; N, 8.96; found: C, 34.75; H, 4.17; N, 8.86.

EXAMPLES 74–77

These Examples are illustrated in Scheme 22. Compound 292, being a multifunctional molecule, has four protected chelating DTPA units as well as a nitro group attached to a benzene ring. This nitro group can serve as a precursor group for attaching any of various targeting groups.

Scheme 22

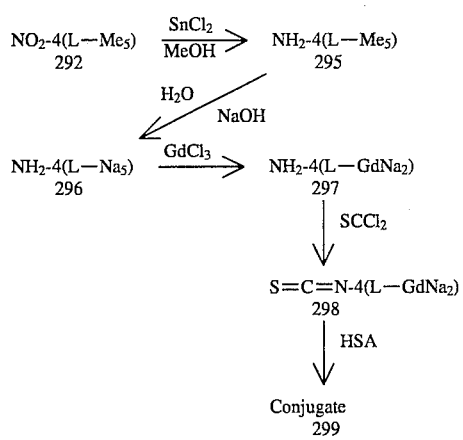

In Example 74 we reduced the nitro group in the methyl-protected compound 292 to produce an amino derivative 295. This compound was de-protected by basic hydrolysis in Example 75 to form a corresponding sodium salt 296. The salt was converted in Example 76 into a corresponding tetragadolinium complex 297. (The free amino group in complex 297 made it possible to link this compound to any of various target biomolecules using conventional labeling procedures, as illustrated in Example 77.) In Example 77, compound 297 was activated by treatment with thiophosgene to form the corresponding isothiocyanate compound 298. The isothiocyanate 298 was reacted with a representative protein (human serum albumin) to form the paramagnetic conjugate 299. It will be understood that any of various polypeptides and other biomolecules having an amino group ($-NH_2$) available for reaction can be attached to compound 298 in a similar manner.

Example 74, pertaining to the reduction of compound 292, was performed as follows: A solution of compound 292 (0.480 g, 0.17 mmol) and $SnCl_2$ (0.600 g, 3.16 mol) in MeOH (80 mL) was refluxed for 20 h, cooled to room temperature, and poured into EtOAc (250 mL). The mixture was washed with saturated $NaHCO_3$ (5×100 mL), then with $H_2O$ (2×50 mL). The mixture was dried ($MgSO_4$) and evaporated. The residue was chromatographed on a preparative TLC plate (30×40 cm×3 mm, eluant: 8% MeOH in $CHCl_3$) to yield 0.358 g (76% yield) of the compound 295 as a glassy solid. Relevant data: liquifies above 50° C.; IR (KBr) 3344, 2959, 1738, 1605, 1514, 1439, 1202 and 1021 $cm^{-1}$. $^1H$ NMR (DMSO-$D_6$) $\delta$2.40–2.95 (gr, 40H), 3.20–3.80 (gr, 116H), 6.35 (e, 1H), 6.45 (s, 2H), 7.09 (d, 8H, J=8 Hz), 7.26 (d, 8H, J=8 Hz), 7.55 (br, 4H, N-H), 9.65 (br, 4H, N-H).

Example 75, which pertained to the hydrolysis of the compound 295, was performed as follows: A mixture of compound 295 (0.068 g, 0.025 mmol) and 1N NaOH (2 mL, 2 mmol) in MeOH (3 mL) was stirred for 23 h at 0° C., cooled to room temperature and evaporated. The residue was re-precipitated with acetone from methanol to yield 0.079 g of compound 296 as a yellowish solid. Relevant data: dec. above 250° C.; IR (KBr) 1593, 1411, 1332 and 1114 $cm^{-1}$; $^1H$ NMR ($D_2O$) $\delta$2.18 (br, 8H), 2.64–2.70 (br, 40H), 2.80–3.80 (gr, 48H), 7.09 (d, 8H, J=8 Hz), 7.25 (d, 8H, J=8 Hz). HPLC (Microsorb $C_{18}$; 20 to 95% B in 20 min): 14.3 (98%).

Example 78 was performed as follows: In a 50 mL 3-neck flask (equipped with a nitrogen inlet and a pH-microelectrode), a magnetically stirred solution of the sodium salt 296 (0.330 g, 0.12 mmol) in water (10 mL) was acidified (0.2N HCl) to pH 6.5. $GdCl_3$. $6H_2O$ (0.200 g, 0.54 mmol) in $H_2O$ (2 mL) was added (pH dropped to 3). The mixture was stirred for 15 min, then the pH was gradually increased to 9 in 3 h by dropwise addition of 0.1N NaOH. The mixture was stirred for 0.5 h and centrifuged. The supernatant was filtered through a 0.45-μm membrane filter and concentrated to 2 mL. Size-exclusion chromatography on Sephadex G-25 column (2.5×80 cm) (controlled by HPLC) yielded the desired compound which was then dissolved in $H_2O$ (5 mL). The cloudy solution was centrifuged; the supernatant was filtered through a membrane filter and evaporated to yield 0.240 g (62% yield) of the tetragadolinium complex 297 as a yellow glassy powder. Relevant data: dec. above 250° C.; IR (KBr) 3429, 1602, 1403, 1323 and 1095 $cm^{-1}$. HPLC (Microsorb $C_{18}$; 20 to 95% B in 15 min): 14.3 min (100%). Anal. calcd for ($C_{104}H_{125}N_{23}O_{40}S_4Gd_4Na_8 24H_2O$): C, 33.66; H, 4.7; N, 8.68; found: C, 33.69; H, 4.75; N, 8.74.

Example 77 was performed as follows: To a solution of the tetragadolinium complex 297 (6.5 mg, 2 mmol) in HEPES buffer (0.5 mL; pH 8.2), a 1N solution of $SCCl_2$ in $CHCl_3$ (20 μL, 20 μmol) was added. The mixture was vigorously shaken for 7 min, then extracted with $CHCl_3$ (3×1 mL) to remove excess thiophosgene, yielding the isothiocyanate-activated compound 298. A solution of HSA (13.8 mg, 0.2 mmol) in $H_2O$ (0.5 mL) was added the extract and the resulting mixture was kept under nitrogen for 24 h. The mixture was then loaded on a Sephadex G-75 column (1.5×40 cm). The column was washed with water (controlled by HPLC) and the major fraction was lipophilized to give 12.1 mg of the paramagnetic conjugate 299 as a glassy substance.

EXAMPLES 78–80

In these Examples, illustrated in Scheme 23, we prepared a tetragadolinium complex 303, containing yet another type of targeting group: a fatty acid residue. Plasma proteins, particularly serum albumins, form complexes with fatty acids. Thus, molecules such as 303 have the ability to bond non-covalently to plasma proteins to form non-covalent conjugates. Compound 303, and other amplifiers of this nature having molecular weights of 10 kD or greater, would be expected to exhibit better relaxation behavior compared to lower molecular weight contrast enchancers.

Scheme 23

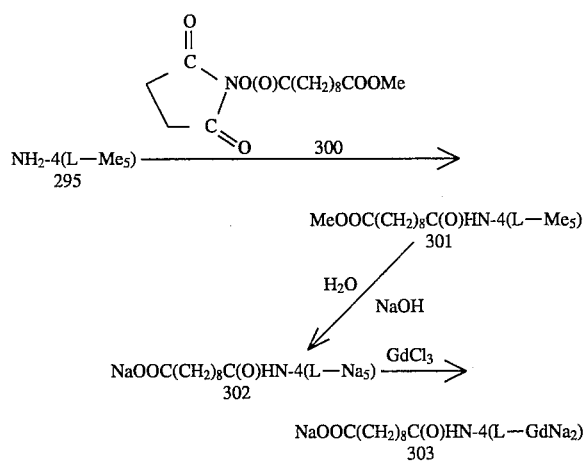

To prepare molecule 303, the amino compound was acylated with the N-hydroxysuccinimide ester of mono methyl-sebacate, compound 300, in Example 78 to produce the amide 301. De-protection of the DTPA units by basic hydrolysis in Example 79 yielded the sodium salt which was converted into the targeting molecule 303 in Example 80 by treatment with Gd(III), followed by size-exclusion chromatography to purify the compound. The complete structure of compound 303 is set forth in Scheme 24.

169.13 (2C), 174.22. Anal. calcd for $C_{15}H_{23}O_6N$: C, 57.50; H, 7.40; N, 4.47; found: C, 57.58; H, 7.17; N, 4.46.

A mixture of the compound 295 (0.245 g, 0.09 mmol) and the active ester 300 (0.157 g, 0.5 mmol) was stirred for 10 days at 50° C., then cooled to room temperature and evaporated. The residual semi-solid was chromatographed on a preparative TLC plate (40×30 cm×3 mm, eluant: 7% MeOH in $CHCl_3$) to yield 0.137 g (53% yield) of the amide 301 as a yellowish glassy solid. This compound liquified Scheme 24

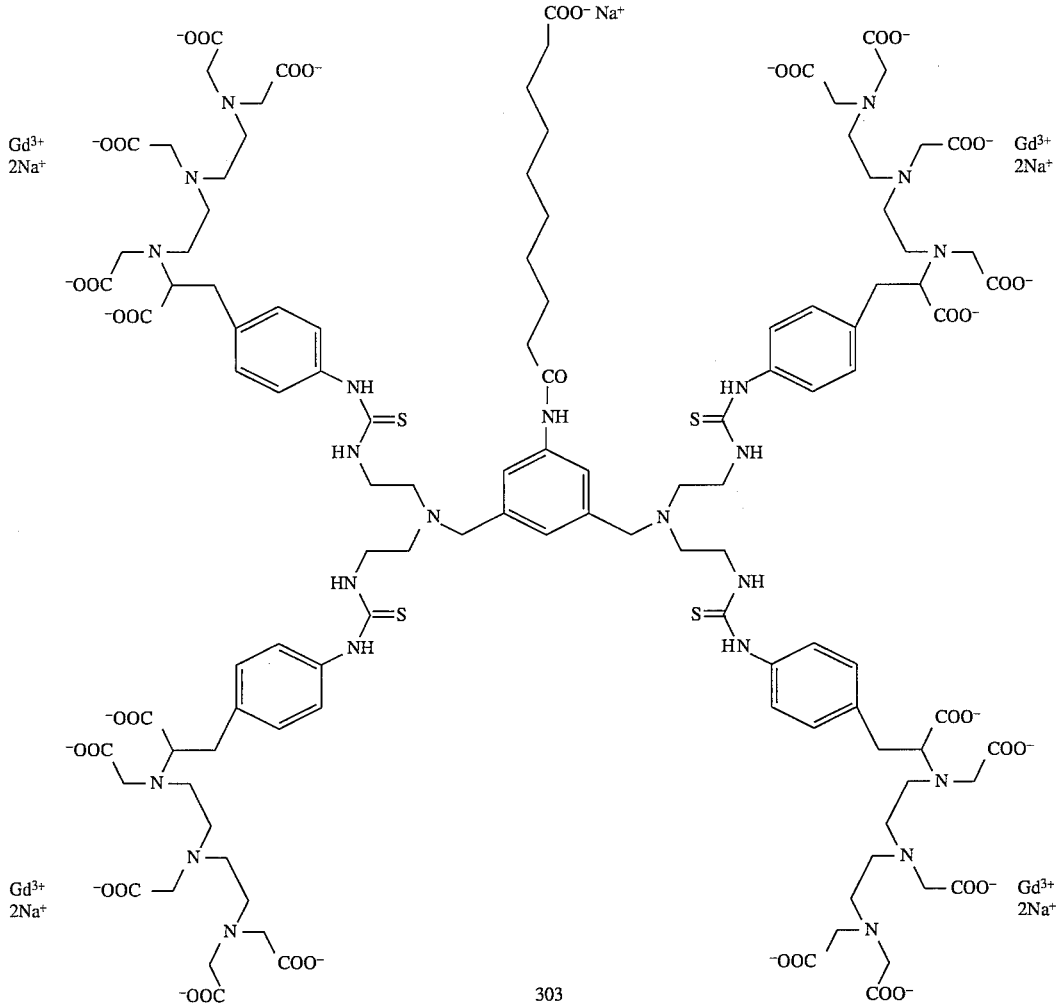

303

In Example 78, which pertained to the acylation of the compound 295, the acylating reagent N-hydroxysuccinidyl-(monomethyl sebacate) 300 was prepared as follows: A mixture of mono-methyl sebacate (0.216 g, 1 mmol), N-hydroxysuccinimide (0.120 g, 1.04 mmol) and DCC (0.210 g, 1.02 mmol) in THF (30 mL) was stirred for 16 h, then filtered to remove DCU. The filtrate was poured into EtOAc (150 mL). The ethyl acetate solution was washed with saturated $NaHCO_3$ (5×20 mL), then with $H_2O$ (2×30 mL). The solution was dried and evaporated to produce 0.275 g (88% yield) of compound 300 as colorless plates. Relevant data: IR (KBr) 1820, 1788, 1735, 1212 and 1072 $cm^{-1}$; $^1H$ NMR ($CDCl_3$) $\delta 1.31$ (br, 8H), 1.61 (m, 2H), 1.73 (m, 2H), 2.29 (t, 2H, J=7.6 Hz), 2.59 (t, 2H, J=7.4 Hz), 2.82 (s, 4H), 3.66 (s, 3H); $^{13}C$ NMR ($CDCl_3$) $\delta 24.50$, 24.85, 25.57 (2C), 28.64, 28.83, 28.91, 28.69, 30.90, 34.04, 51.41, 168.61, above 60° C. The compound was found to be unstable and was thus immediately used in Example 79.

Example 79, pertaining to the hydrolysis of compound 301, was performed as follows: A mixture of compound 301 (0.170 g, 0.059 mmol) and 1N NaOH (4 mL, 4 mmol) in MeOH (15 mL) was stirred for 23 h at 45° C., cooled to room temperature, and evaporated. The residue was reprecipitated with acetone from methanol to yield 0.180 g of the compound 302 as a yellowish solid. Relevant data: dec. above 250° C.; IR (KBr) 1592, 1411, 1331 and 1114 $cm^{-1}$. $^1H$ NMR (D20) $\delta 1.23$ (m, 8H), 1.51 (m, 20H), 2.58 (br.s, 36H), 2.65 (br.s, 8H), 2.80–3.70 (gr, 40H), 6.66 (s, 2H), 6.70 (s, 1H), 7.09 (d, 8H, J=7 Hz), 7.25 (d, 8H, J=7 Hz). HPLC (Microsorb $C_{18}$; 20 to 95% B in 20 min): 18.8 min (97%).

Example 80 was performed as follows: In a 20-mL 3-neck flask (equipped with a nitrogen inlet and a pH-microelectrode), a magnetically stirred solution of the sodium salt 302 (0.030 g, 0.01 mmol) in water (2 mL) was acidified (0.2N HCl) to pH 6.5.GdCl$_3$.6H$_2$O (0.017 g, 0.045 mmol) in H$_2$O (1 mL) was added (pH dropped to 3). The mixture was stirred for 15 min, then the pH was gradually increased to 9 in 4 h by dropwise addition of 0.1N NaOH. The mixture was stirred for 0.5 h, filtered through a 0.45 μm membrane filter and concentrated to 2 mL. Size-exclusion chromatography of the concentrate on a Sephadex G-25 column (2.5×80 cm) (controlled by HPLC) yielded 0.024 g (70% yield) of complex 303 as a yellow glassy powder. Relevant data: dec. above 250° C.; IR (KBr) 1611, 1405, 1320, 1263 and 1095 cm$^{-1}$; HPLC (Microsorb C$_{18}$; 20 to 95% B in 15 min): 19.0 min (96%). Anal. calcd for (C$_{114}$H$_{140}$O$_{43}$N$_{23}$S$_4$Gd$_4$Na$_9$+ 28H$_2$O): C, 34.46; H, 4.97; N, 8.11; found: C, 34.52; H, 4.88; N, 8.05.

EXAMPLES 81–83

These Examples pertain to representative syntheses of a group of amplifiers having amplification factors of two, four, eight, etc., as depicted in Scheme 25 and Scheme 26 wherein R2 is an active group such as (but not limited to) a nitroxide or paramagnetic metal ion chelator. Compounds 310 and 311 have amplification factors of two, and compound 307 has an amplification factor of four. Thus, the amplification factor of an amplifier depends upon the particular active group(s) present on the amplifier molecule.

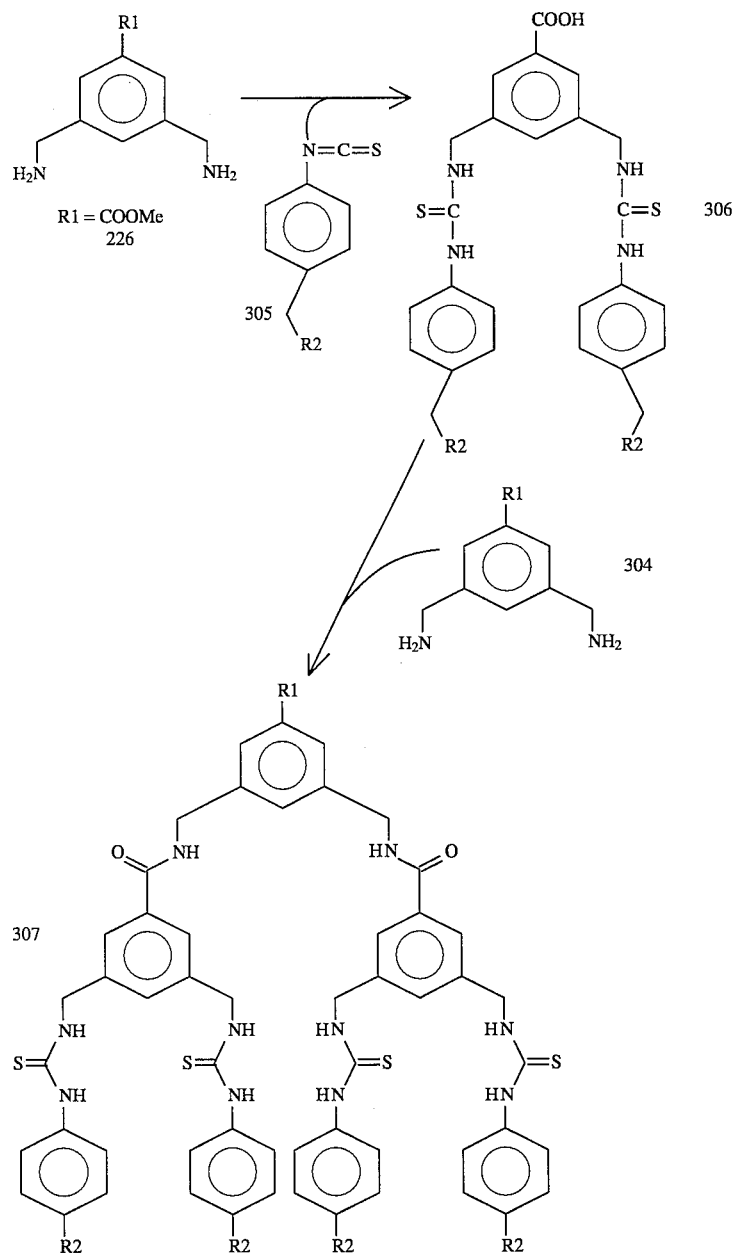

Scheme 25

As can be readily appreciated, the chemistry depicted in Scheme 26 can be repeated to produce variants of compound 307 having even more extensive dendritic structure than compound 307. For example, compound 307 can be reacted with compound 304 (in the same manner as compound 306 is reacted with compound 304) to produce a variant of compound 307 having an amplification factor of eight.

Scheme 25 illustrates the general applicability of the reaction of amines with carboxylic acids to form amide linkages (e.g., formation of compound 307 by reaction of compounds 304 and 306) as a way to synthesize any of various amplifiers according to the present invention. Scheme 25 also illustrates the general applicability of the reaction of isothiocyanates with amines to yield thiourea linkages useful in synthesizing any of various amplifiers according to the present invention (e.g., reaction of compound 305 with compound 304 to produce compound Use of Scheme 25 to synthesize amplifiers containing any of various paramagnetic metal-ion chelators is exemplified in Scheme 26.

amplifiers according to the present invention having amplification factors of four or eight. Molecules having higher amplification factors can also be made by further exploitation of the same reactions in various sequential combinations.

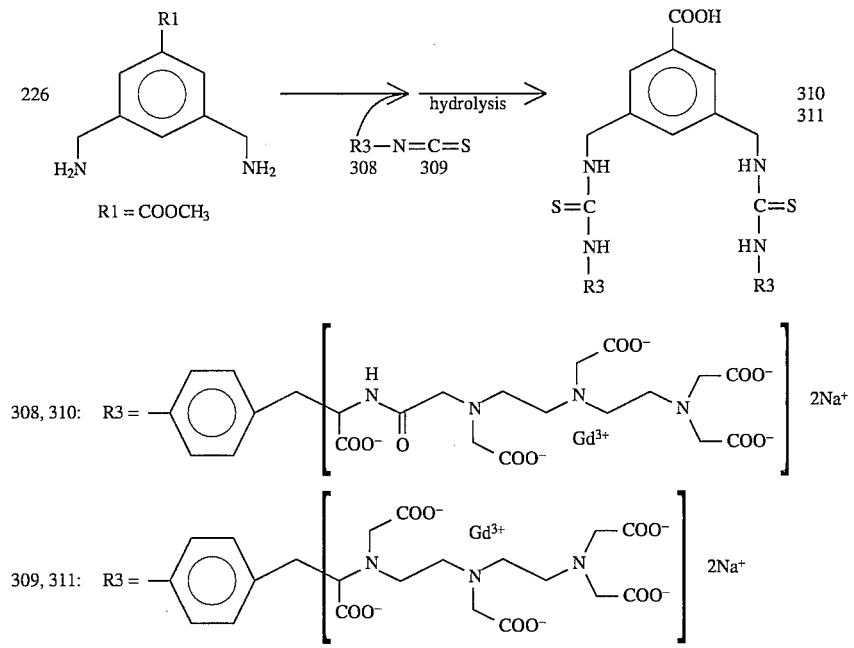

Scheme 26

Compounds 310 and 311 can be reacted with compound 226 to produce a compound (shown generally in Scheme 25 as compound 307) having an amplification factor of four. Also, compound 311 is the free acid form of compound 281.

EXAMPLES 84–88

These Examples pertain to representative schemes (Schemes 27 and 28) for the synthesis of other specific Scheme 27

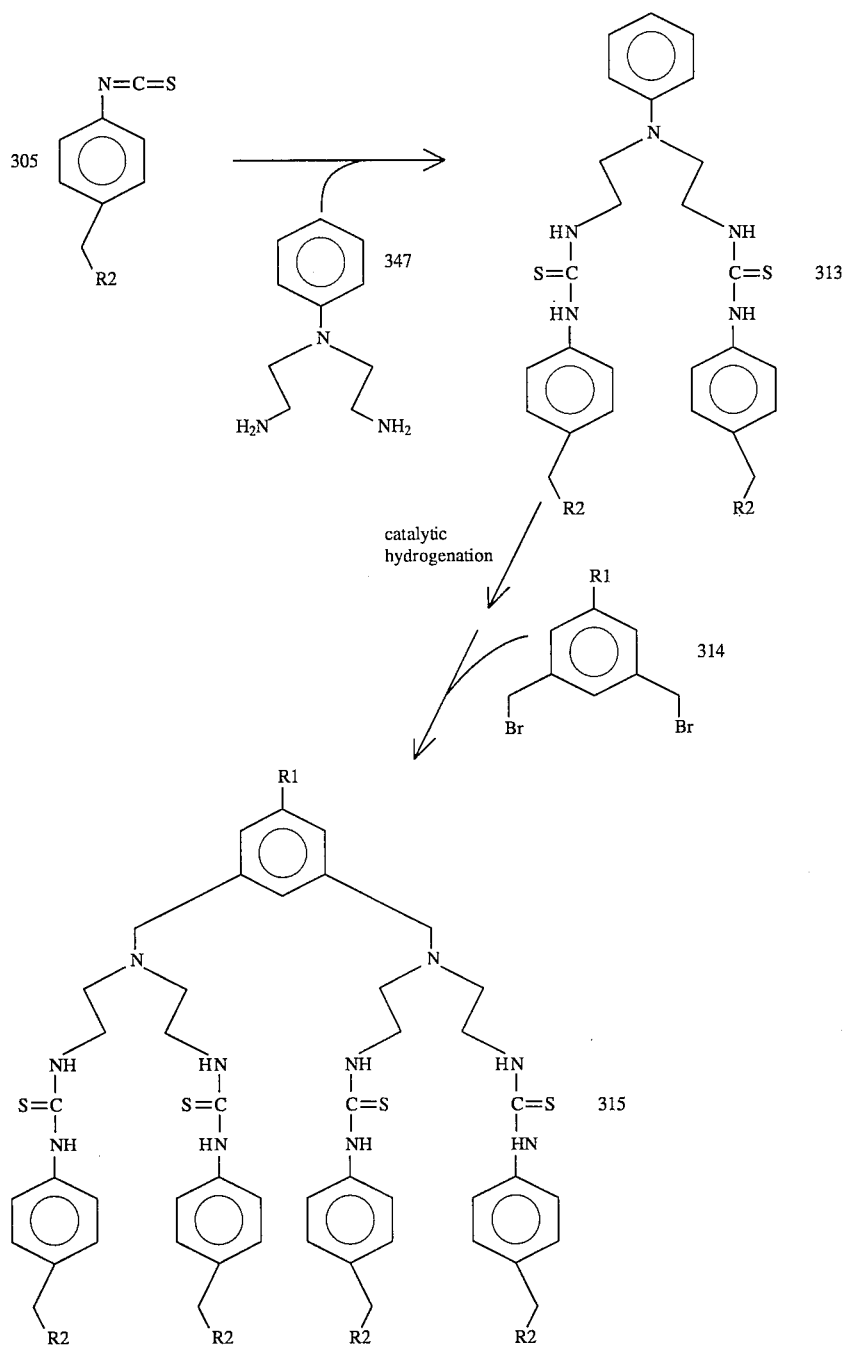

In scheme 27, R2 is an active group. The N-benzyl group on compound 347 protects the middle nitrogen, thereby facilitating regio-selective reaction of compound 305 with the terminal amines of compound 347. The benzyl group is later removed, before reaction with compound 314, by catalytic hydrogenation. Compound 315 has an amplification factor of four.

In Scheme 28, compound 317 can be reacted with, for example, compound 307 (Scheme 25) to produce an amplifier having an amplificatlon factor of eight.

It can be readily seen that a major reaction exploited in Scheme 27 is the reaction of an isothiocyanate with an amine (e.g., reaction of compound 305 with DETA, compound 312, to form amplifiers having thiourea linkages as found in compound 313).

Further utilization of reactions involving isothiocyanates and carboxylic acids with amines to form other amplifiers according to the present invention is exemplified in Scheme 28 wherein R2 is a paramagnetic metal-ion chelator. It will be appreciated that R2 can also be another active group such as, but not limited to, a nitroxide group (along with a second nitroxide on each terminal primary amine in place of the remaining amino hydrogen.)

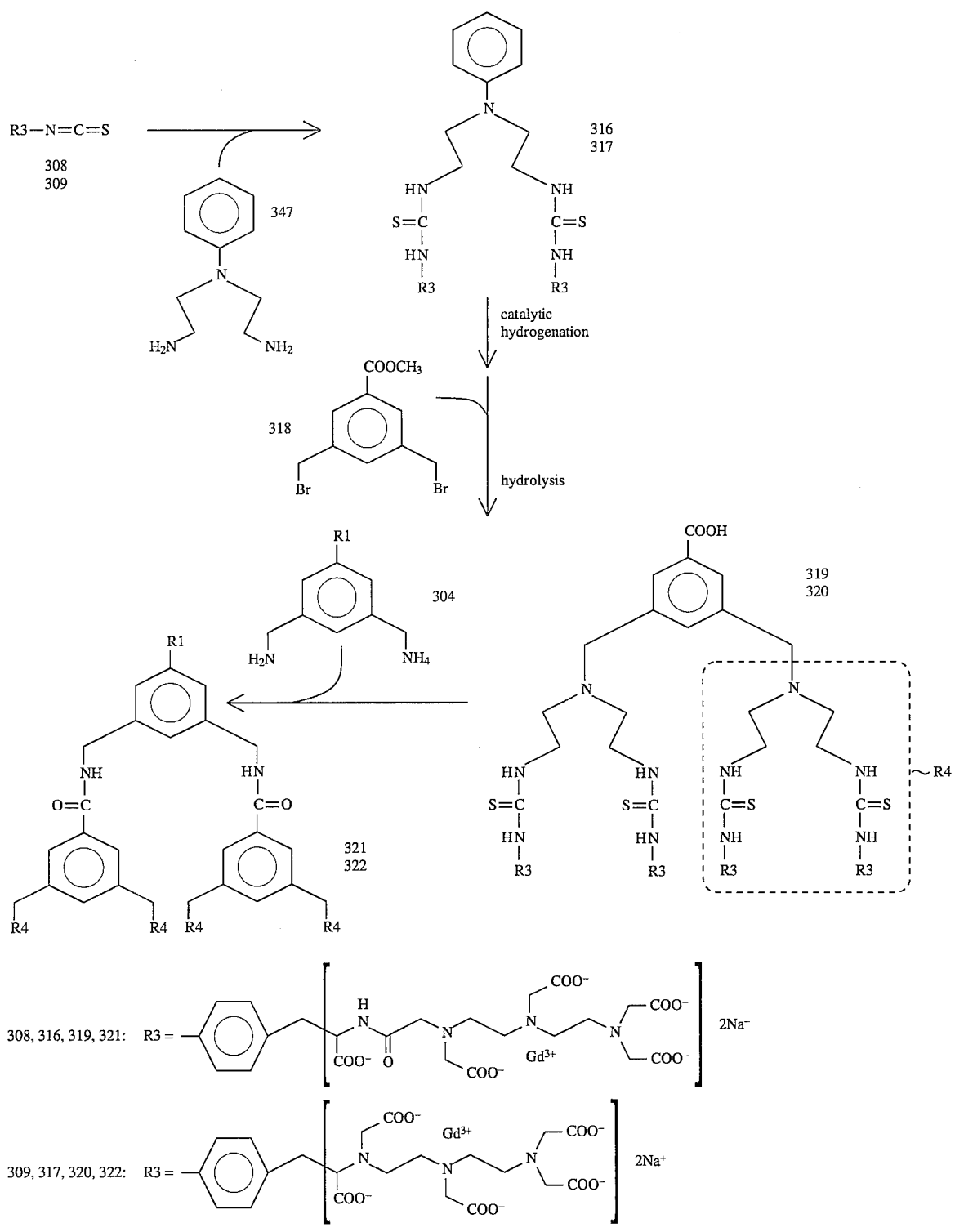
Scheme 28
As can be seen, each of compounds 319 and 320 has an amplification factor of four, and each of compounds 321 and 322 has an amplification factor of eight.
EXAMPLES 89–97
These Examples pertain to the synthesis of yet other specific amplifier molecules according to the present invention, as illustrated in Schemes 29 and 30.

Scheme 29
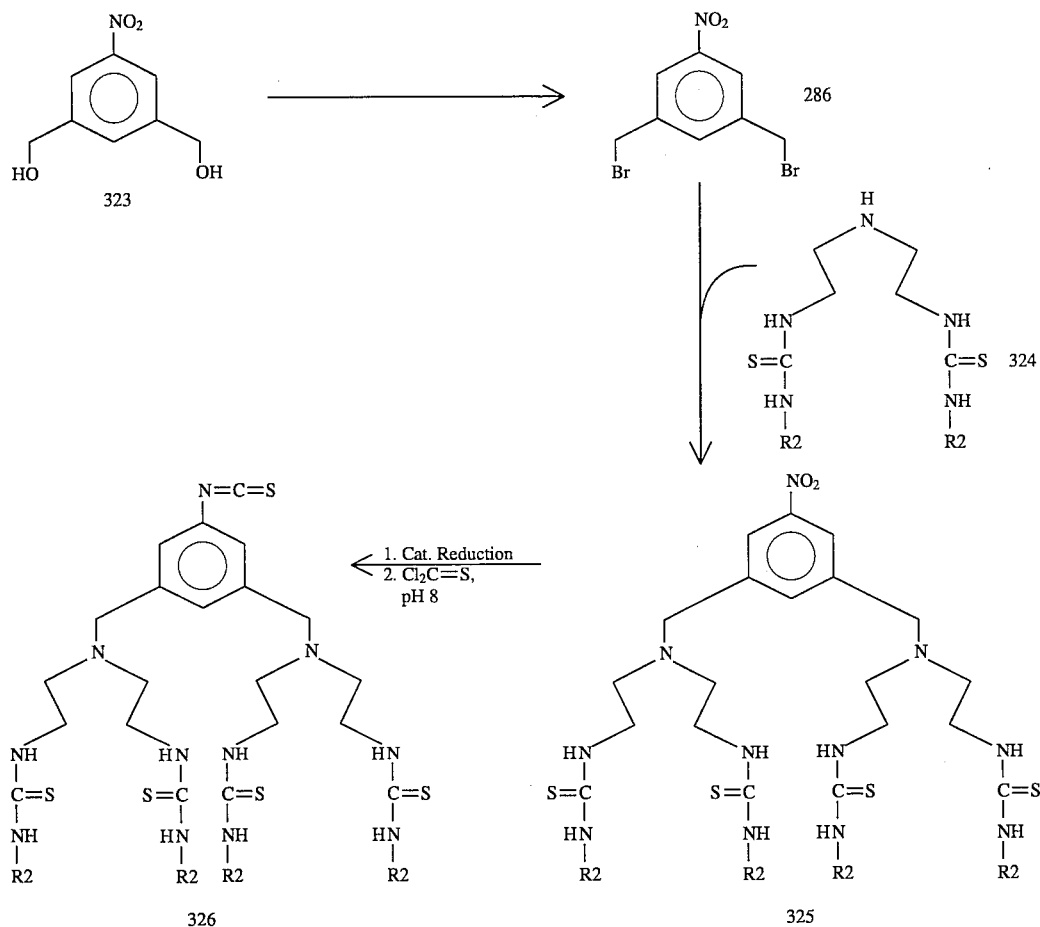
Scheme 30
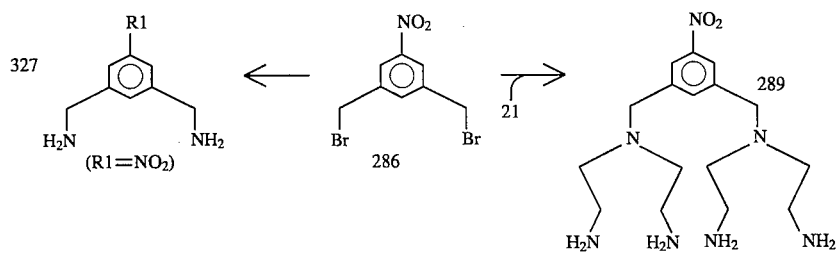

-continued
Scheme 30

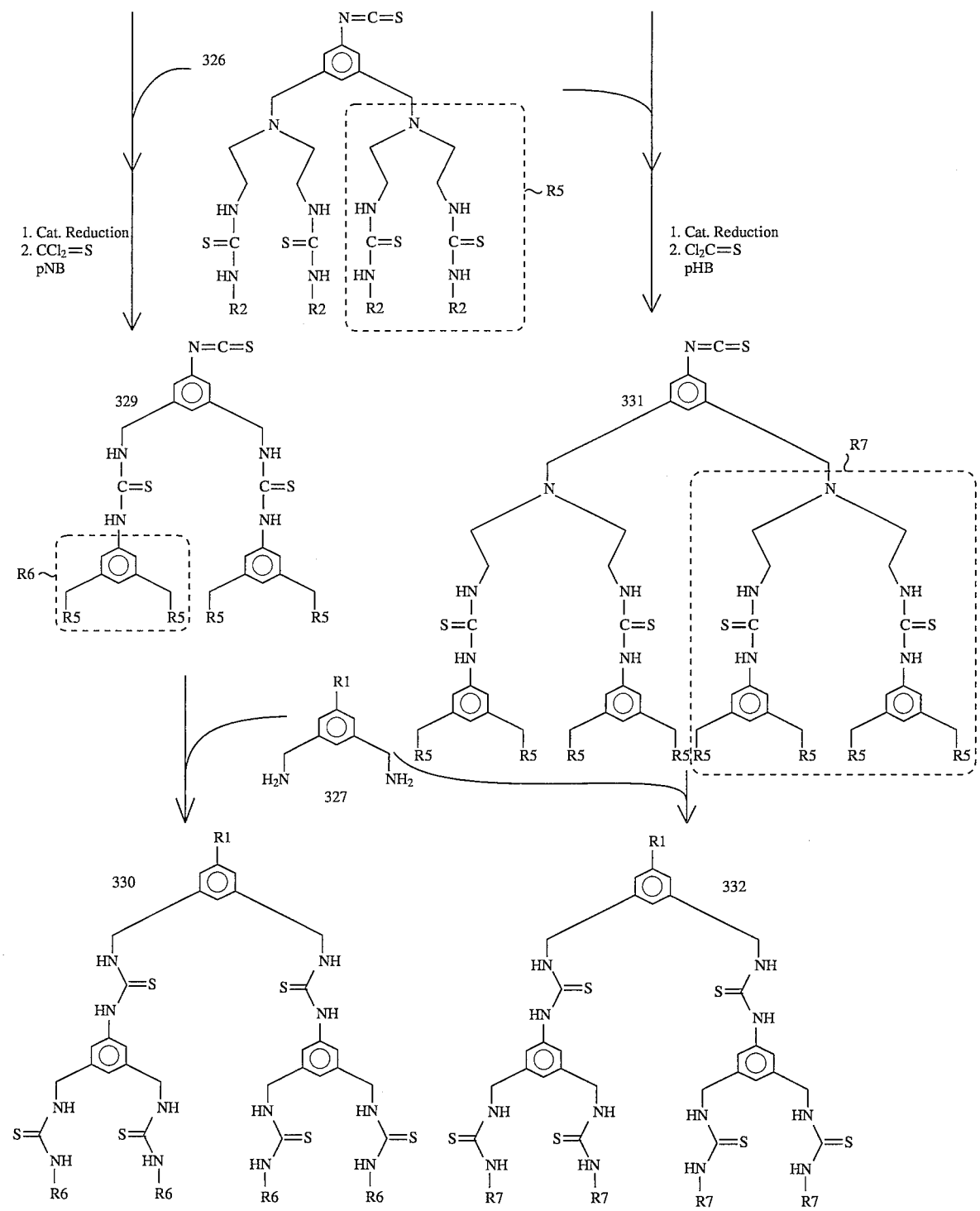

In Schemes 29 and 30, each of compounds 325 and 326 has an amplification factor of four. Compound 329 has an amplification factor of eight. Each of compounds 330 and 331 has an amplification factor of sixteen; and compound 332 has an amplification factor of thirty-two. R2 is an active group such as, but not limited to, a paramagnetic metal-ion chelator or a nitroxide. In the case of R2 being a nitroxide, the remaining amino hydrogen adjacent each R2 group can be replaced with a second nitroxide, yielding two nitroxide groups per terminal primary amine in the amplifier, and thereby doubling the amplification factor of the compound.

EXAMPLES 98–104

These Examples pertain to a representative scheme (Scheme 31) for the synthesis of compound 309 from DTPA, compound 333, and for a representative interconversion scheme for various derivatives of compound 309.
The synthesis shown in Scheme 32 begins with diethylenetriaminepentaacetic acid (DTPA; compound 333). The
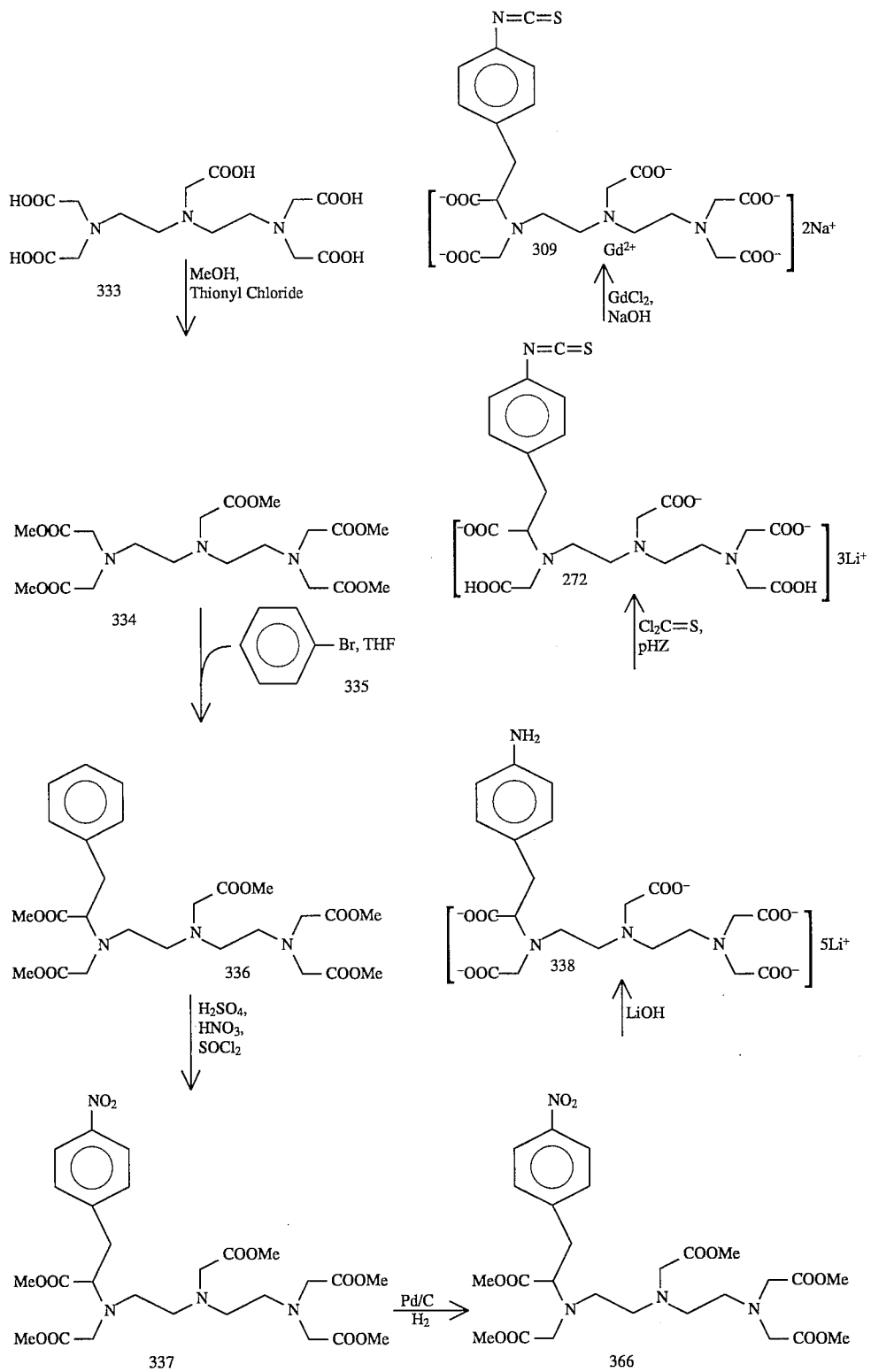
Scheme 31 details of synthesis of these variants (i.e., compounds 334, 336, 337, 266, 338, 272, and 309) are as set forth in my U.S. Pat. Nos. 5,135,737 and 5,252,317, incorporated herein by reference.

EXAMPLES 105-08

These Examples pertain to an investigation of the selective reduction of the nitro group (e.g., in the 1-position on a core group) in the presence of methoxycarbonyl groups and thiourea linkages of linkers, branch groups, and active groups. Model reactions are shown in Scheme 32:

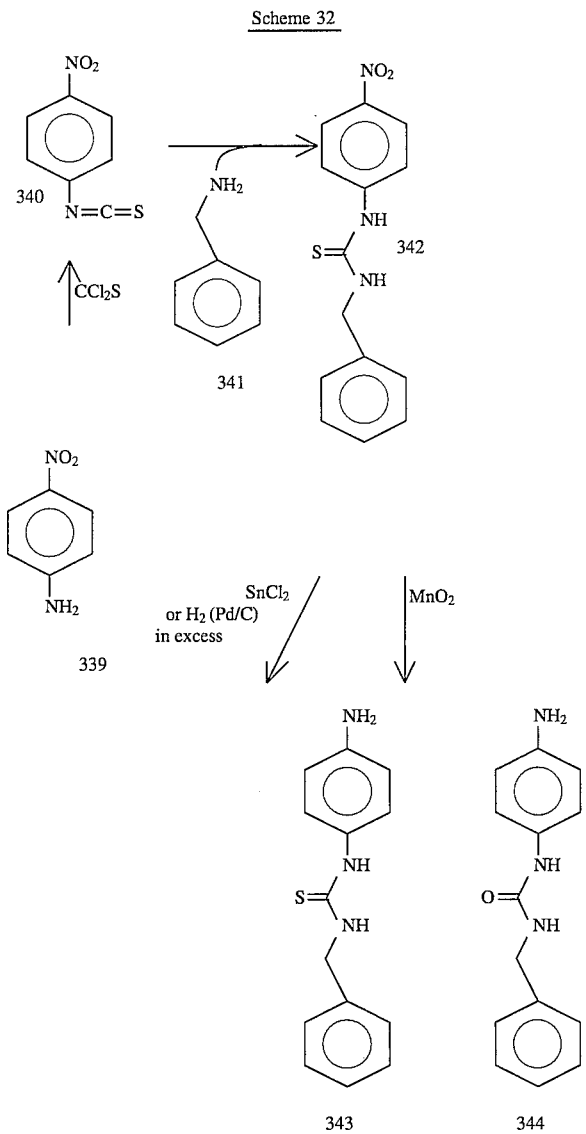

Referring to Scheme 32, p-nitrophenylisothiocyanate 340 was prepared in Example 105 by reaction of p-nitrobenzylamine 339 with thiophosgene.

In Example 106, reaction of compound 340 with aminomethylbenzene 341 yielded the model compound 342 containing a thiourea linkage, as follows: To a solution of isothiocyanate 340 (1.80 g, 10 mol, prepared in Example 105 from the p-nitro aniline 339), benzylamine 341 (1.64 mL, 15 mmol) was added dropwise. The resulting mixture was stirred for 16 hours, then evaporated. The solid residue was washed on a filter sequentially with 2N HCl (5×10 mL), and $H_2O$ (5×5 mL), then dried in vacuo to produce a crude product that was crystallized from EtOAc to yield 2.190 g (76% yield) of benzyl-(4-nitrophenyl) thiourea 342 as an orange powder. Relevant data: mp 151°–152° C. (from EtOAc); $^1H$ NMR (DMSO-d6): δ4.74 (s, 2H), 7.34 (m, 5H), 7.84 (d, 2H, J=9 Hz), 8.15 (d, 2H, J=9 Hz), 8.65 (s, 1H, NH), 10.21 (s, 1H, NH); $^{13}C$ NMR (DMSO-d6): δ48.17, 121.62, 125.34, 128.04, 128.55, 129.30, 139.11, 142.92, 147.28, 181.36; MS m/e (1%): 287 (M+, 22), 180 (100), 150 (51), 138 (21), 122 (43), 106 (81), 107 (56), 91 (95).

In Example 107, reduction of the nitro group in compound 342 by reaction with stannous chloride in methanol proceeded selectively and resulted in the formation of amino derivative 343 in high yield, as follows: A mixture of thiourea 342 (0.287 g, 1 mmol) and $SnCl_2.2H_2O$ (0.5 g, 2.2 mmol) in MeOH (25 mL) was refluxed for 4 hours, cooled to room temperature, then poured into EtOAc (150 mL. The mixture was sequentially washed with saturated $NaHCO_3$ (5×20 mL) and $H_2O$ (3×20 mL), dried over $MgSO_4$, then evaporated. The residue was chromatographed over silica gel (2×15 cm, eluant: 1% MeOH in $CHCl_3$) to produce (4-aminophenyl)-benzyl thiourea 343 (0.192 g, 75% yield) as a white powder. Relevant data: mp 153°–155° C. (from EtOAc); $^1H$ NMR (DMSO-d6): δ4.65 (d, 2H, J=5.7 Hz), 5.05 (br.s., 2H, $NH_2$), 6.50 (d, 2H, J=9 Hz), 6.85 (d, 2H, J=9Hz), 7.25 (m, 5H), 7.61 (br.s., 1H, NH), 9.15 (s, 1H, NH); $^{13}C$ NMR (DMSO-d6) δ47.50, 114.72, 126.96, 127.23, 127.51, 128.66, 139.57, 146.88, 181.305; MS m/e (1%): 257 (M+, 42), 256 (17), 182 (25), 165 (6), 150 (100), 108 (75), 107 (37), 106 (47), 91 (92).

An alternative way to synthesize compound 343 is also set forth in Scheme 32, involving a catalytic hydrogenation of compound 341 (catalyst: 10% w/w of 30% Pd/C), as follows: To a solution of thiourea 342 (0.100 g, 0.348 mmol) in MeOH (20 mL), 10% Pd/C catalyst (0.1 g) was added. The mixture was hydrogenated with 60 psi $H_2$ gas for 16 hours, after which the catalyst was removed by filtration. The filtrate was evaporated and the residue treated with cold hexane (5 mL). The product was filtered and washed with cold hexane (3 mL) to yield compound 343 (0.084 g, 94% yield).

The foregoing results indicate that it is possible to reduce an aromatic nitro group catalytically in the presence of a thiourea group. Also, these results indicate that the perester 292 (Scheme 21) is an attractive and versatile precursor for producing tetracomplex amplifiers according to the present invention.

Example 108 was performed as follows: A mixture of thiourea 342 (0.100 g, 0.348 mmol) and $MnO_2$ (0.500 g, 5,75 mmol) in $CHCl_3$ (20 mL) was stirred for 16 hours in an open flask. Inorganic material was removed by filtration and washed with $CHCl_3$ (5×5 mL). The combined filtrates were evaporated. The residue was purified on a preparative TLC plate (eluant: 10:1 ether:THF) to yield compound 344 (0.082 g, 87% yield) as a yellowish solid. Relevant data: mp 163°–165° C. (from EtOAc); $^1H$ NMR (DMSO-d6):δ4.30 (d, 2H, J=9 Hz), 6.92 (m, 1H, NH), 7.30 (m, 5H), 7.62 (d, 2H, J=9 Hz), 8.12 (d, 2H, J=9 Hz), 9.37 (s, 1H, NH); MS m/e (I%): 271 (M+, 46), 164 (32), 138 (100), 134 (29), 108 (57), 107 (30), 106 (48), 105 (18), 91 (86). This reaction is applicable for the synthesis of amplifiers according to the present invention that contain no sulfur atoms.

EXAMPLE 109

This Example pertains to the synthesis of an amplifier according to the present invention having an amplification factor of eight. The reactions are shown in Scheme 33.

Scheme 33

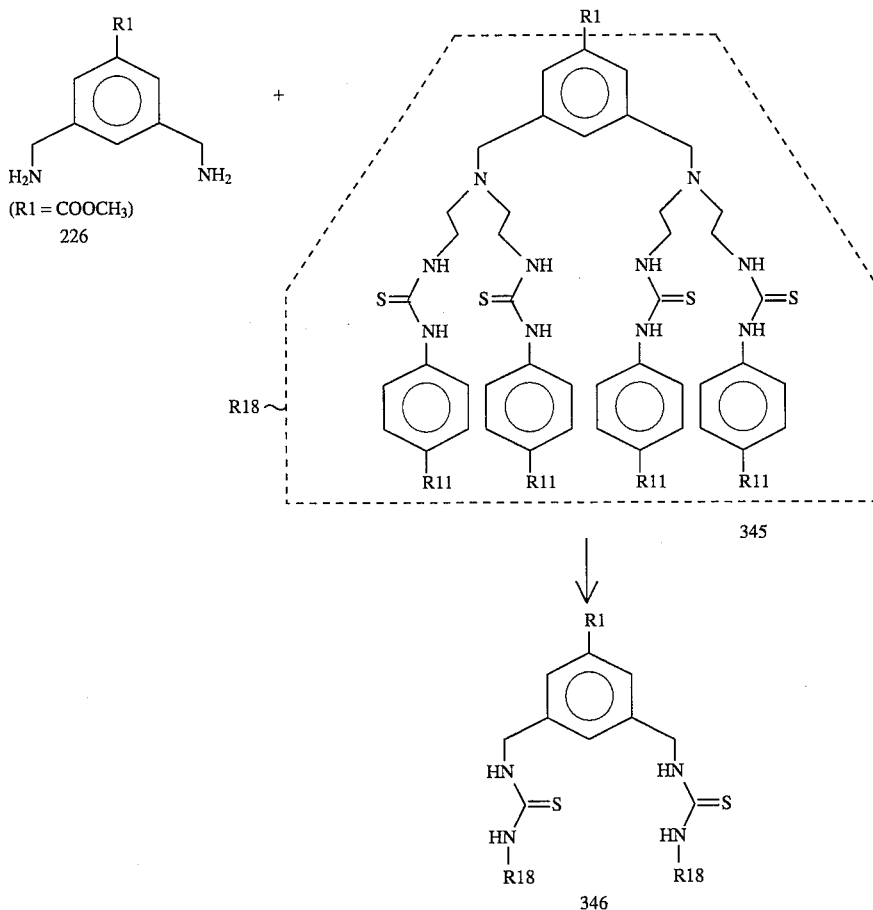

In Scheme 33, R11 is the L-Me$_5$ group which, as described above, can be readily converted to the corresponding gadolinium-salt chelating group.

Compound 346 has an amplification factor of eight. Although compound 346 is shown with eight perester DTPA derivatives, it will be readily understood that an analogous compound can be synthesized having, instead of the phenyl-R11 groups on each terminal amine, one or two nitroxide groups, or one or two other active groups.

EXAMPLES 110–115

In these Examples, relaxivity data were obtained for each of compounds 271, 277, 281, 294, 297, and 303 in water and in 4% BSA solution, as shown in Table II. For comparison, certain relaxivity data are also presented for (Gd-DTPA)-dextran, Mann et al., *Bioconjugate Chem.* 3:154 (1992), for (Gd-DTPA)-HSA, Ogan et al., *Investig. Radiol.* 22:665 (1987), and for Gd-DTPA.

TABLE II

| Compound | #Gd(III) | $R_1$ in Water | | $R_1$ in 4% BSA | |
|---|---|---|---|---|---|
| | | per mol | per Gd(III) | per mol | per Gd(III) |
| Gd—DTPA | 1 | 4.5 | 4.5 | ~5 | ~5 |
| 271 | 1 | 3.7 | 3.7 | 12.6 | 12.6 |
| 277 | 1 | 3.4 | 3.4 | 9.5 | 9.5 |
| 281 | 2 | 9.4 | 4.7 | 18.6 | 9.3 |
| 294 | 4 | 53.2 | 13.3 | 81.6 | 20.4 |
| 297 | 4 | 36.4 | 9.1 | 82.4 | 20.6 |
| 303 | 4 | 41.6 | 10.4 | 98.4 | 24.6 |
| (Gd—DTPA)-dextran | | | 15.0 | | n/d(est. ~15)* |
| (Gd—DTPA)—HSA | | | 14.9 | | n/d(est. ~15)* |

*Sieving et al., Bioconjugate Chem. 1:65 (1990).

In TABLE II, the dramatic increase in relaxivity per gadolinium atom in compounds having amplification factors of four or greater is apparent. Thus, amplifiers according to the present invention used for MRI contrast enhancement can exhibit an improved contrast-enhancement performance that is beyond what would be expected simply on the basis of amplification factor alone.

EXAMPLE 116

Figure 3A:
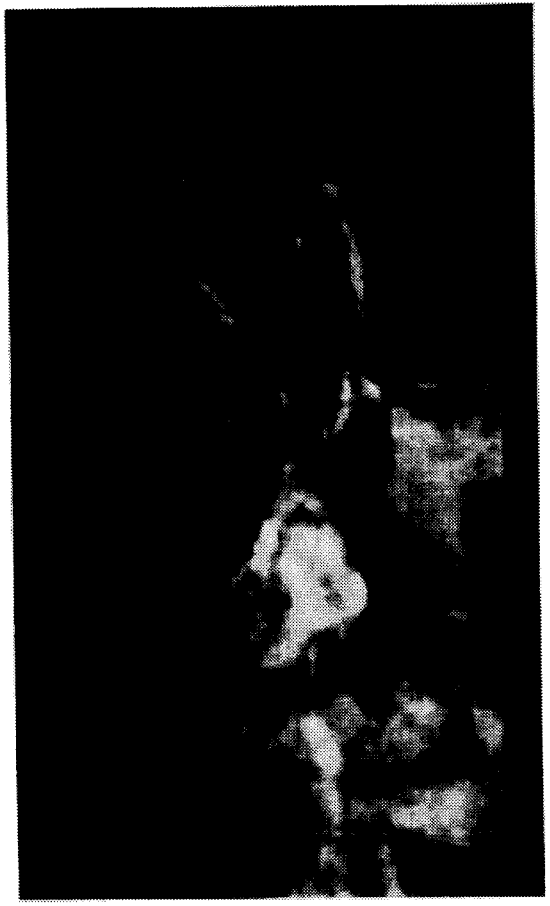
Figure 3B:
Figure 3C:
Figure 3D:

In this Example, compound 303 was administered by injection to an adult laboratory rat to ascertain the ability of the compound to enhance the contrast of a magnetic resonance (MR) image. MR angiography was performed prior to, and 15, 30, and 45 minutes post-injection of 10 μmoles complexed gadolinium (as compound 303 in a 20 mM solution) per kg body weight. FIGS. 3A–3D depict the results, wherein FIG. 3A shows upper-body vasculature prior to injection and FIGS. 3B–3D show the vasculature 15, 30, and 45 minutes post-injection, respectively. FIGS. 3B–3D reveal definitely increased contrast enhancement, indicated as an enhanced vasculature that is especially evident in the superior great vessels and in the descending aorta. Thus, compound 303 is representative of compounds according to the present invention that are useful as MR blood-pool agents.

While the present invention has been described in connection with preferred embodiments and multiple examples, it will be understood that the invention is not limited to those embodiments and examples. On the contrary, the invention is intended to include all alternatives, modifications, and equivalents as may be included within the spirit and scope of the invention as defined by the appended claims.

What is claimed is:

1. A compound having the structure:

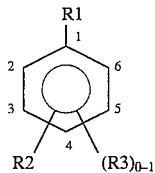

wherein:
(a) R1 is selected from a group consisting of:
R2,
R3, and
groups having the structure —(R4)$_{0-1}$—(R5)$_{0-1}$—(R6)(—R7)$_{0-1}$ wherein R4 is selected from a group consisting of C(O)—NH, C(S)—NH, C(O), O, NH—C(O), NH—C(S), NH—C(S)—NH, NH—C(O)—NH, C(O)—O, and O—C(O); R5 is selected from a group consisting of aryls, aryl-(C$_1$–C$_{20}$ alkyls), (C$_1$–C$_{20}$ alkyl)-aryls, cycloalkyls, C$_1$–C$_{20}$ alkyls and combinations thereof; R6 is selected from a group consisting of H, C$_1$–C$_6$ alkyls, C(O)—OH, C(O)—O—(C$_1$–C$_6$ alkyls), C(O)—O$^-$ X$^+$, NH$_2$, NO$_2$, NCS, NCO, OH, SH, B(OH)$_2$, and R4, wherein X is a monovalent metal cation; and R7 is a targeting group; and (b) R2 and R3, which are the same or different, each has the structure

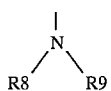

wherein R8 and R9, which are the same or different, are a hydrogen or a group having the structure —R10—(R11)—(R12)$_{0-1}$—(R13)$_n$ and at least one of said R8 and R9 groups has the —R10—(R11)—(R12)$_{0-1}$—(R13)$_n$ structure, wherein R10 is at least one structure selected from a group consisting of linkers and branch groups, the linkers and branch groups, when more than one is present in R10, being covalently bonded together in a series manner to form R10;

R11 is selected from a group consisting of —NH—C(O)—, —C(O)—NH—, —C(O)—, —NH—C(S)—, —C(S)—NH—, —NH—C(O)—NH—, —NH—C(S)—NH—, —NH—C(O)—O—, —O—C(O)—NH—, —C(O)—O—, and —O—C(O)—;

R12 is an aryl, C$_1$–C$_{12}$ alkyl, (C$_1$–C$_{12}$ alkyl)-aryl, cycloalkyl, aryl-(C$_1$–C$_{12}$ alkyl), or a combination thereof; and R13 is an active group wherein n is 1 or 2.

2. A compound as recited in claim 1 wherein the linkers have the structure —(R14)$_{0-1}$-R15— or —R15—(R14)$_{0-1}$—, wherein R14 is an aryl, cycloalkyl, C$_1$–C$_{12}$ alkyl, aryl-(C$_1$–C$_{12}$ alkyl), or (C$_1$–C$_{12}$ alkyl)-aryl group, or a combination thereof covalently bonded together in a series manner; and R15 is selected from a group consisting of C(O)—NH, C(S)—NH, C(O), NH—C(O), NH—C(S), NH—C(S)—NH, NH—C(O)—NH, NH—C(O)—O, O—C(O)—NH, C(O)—O, and O—C(O).

3. A compound as recited in claim 2 wherein the branch groups have a structure selected from a group consisting of

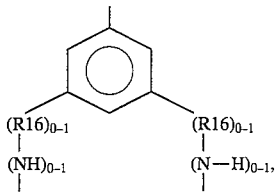

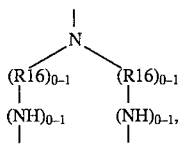

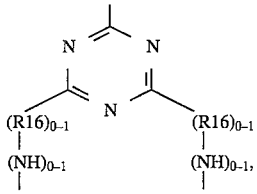

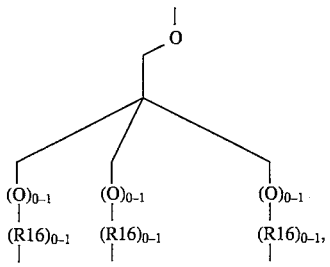

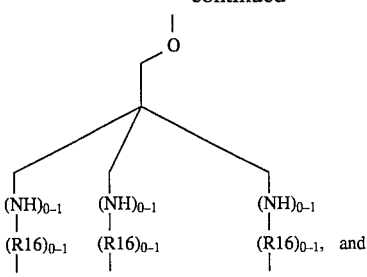

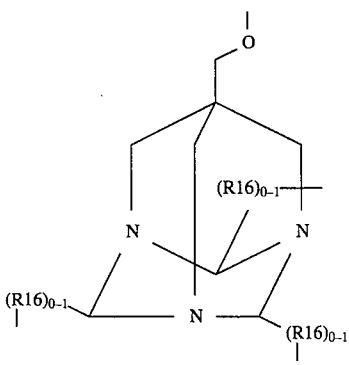

wherein R16 is a $C_1$-$C_6$ alkyl.

4. A compound as recited in claim 1 wherein R13 is selected from a group consisting of paramagnetic metal-ion chelators and nitroxides.

5. A compound as recited in claim 4 capable of decreasing a T1 or T2 relaxation time of protons present in a physiological environment containing said compound.

6. A compound as recited in claim 1 wherein R7 is selected from a group consisting of polypeptides, proteins, antibodies, nucleic acids, carbohydrates, fatty acids, surfactants, glycerides, steroids, porphyrins, and enzyme inhibitors.

7. A composition of matter comprising a compound as recited in claim 1 in a physiologically compatible carrier.

8. A compound having the structure:

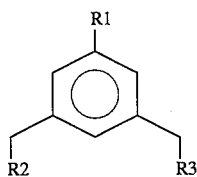

wherein:
(a) R1 is selected from a group consisting of:
R2,
R3, and
groups having the structure —(R4)$_{0-1}$—(R5)$_{0-1}$—R6 (—R7)$_{0-1}$, wherein R4 is selected from a group consisting of C(O)—NH, C(S)—NH, C(O), O, NH—C(O), NH—C(S), NH—C(S)—NH, NH—C(O)—NH, C(O)—O, and O—C(O); R5 is selected from a group consisting of aryls, aryl-($C_1$-$C_{20}$ alkyls), ($C_1$-$C_{20}$ alkyl)-aryls, cycloalkyls, $C_1$-$C_{20}$ alkyls, and combinations thereof; R6 is selected from a group consisting of H, $C_1$-$C_6$ alkyls, C(O)—OH, C(O)—O—($C_1$-$C_6$ alkyls), C(O)—O$^-$X$^+$, NH$_2$, NO$_2$, NCS, NCO, OH, SH, B(OH)$_2$, and R4, wherein X is a monovalent metal cation; and R7 is a targeting group; and (b) R2 and R3, which are the same or different, each has the structure

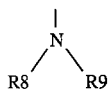

wherein R8 and R9, which are the same or different, are a hydrogen or a group having the structure —R10—R11—(R12)$_{0-1}$—(R13)$_n$ and at least one of said R8 and R9 groups has the —R10—(R11)—(R12)$_{0-1}$—(R13)$_n$ structure, wherein R10 is at least one structure selected from a group consisting of linkers and branch groups, the linkers and branch groups, when more than one is present in R10, being covalently bonded together in a series manner to form R10;

R11 is selected from a group consisting of —NH—C(O)—, —C(O)—NH—, —C(O)—, —NH—C(S)—, —C(S)—NH—, —NH—C(O)—NH—, —NH—C(S)—NH—, —NH—C(O)—O—, —O—C(O)—NH—, —C(O)—O—, and —O—C(O)—;

R12 is an aryl, $C_1$-$C_{12}$ alkyl, ($C_1$-$C_{12}$ alkyl)-aryl, cycloalkyl, aryl-($C_1$-$C_{12}$ alkyl), or a combination thereof; and R13 is an active group wherein n is 1 or 2.

9. A compound as recited in claim 8, wherein the linkers have the structure —(R14)$_{0-1}$—R15— or —R15—(R14)$_{0-1}$—, wherein R14 is an aryl, cycloalkyl, $C_1$-$C_{12}$ alkyl, aryl-($C_1$-$C_{12}$ alkyl), or ($C_1$-$C_{12}$ alkyl)-aryl group, or a combination thereof covalently bonded together in a series manner; and R15 is selected from a group consisting of C(O)—NH, C(S)—NH, C(O), NH—C(O), NH—C(S), NH—C(S)—NH, NH—C(O)—NH, NH—C(O)—O, O—C(O)—NH, C(O)—O, and O—C(O).

10. A compound as recited in claim 9, wherein the branch groups have a structure selected from a group consisting of

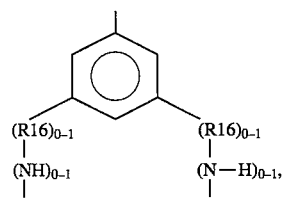

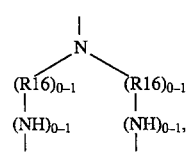

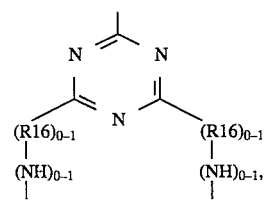

-continued

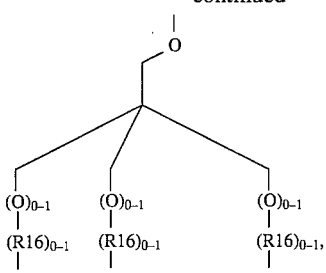

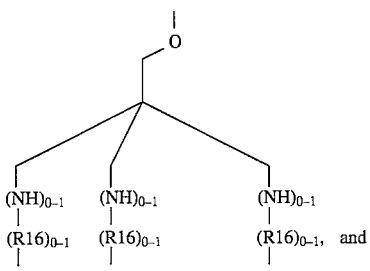

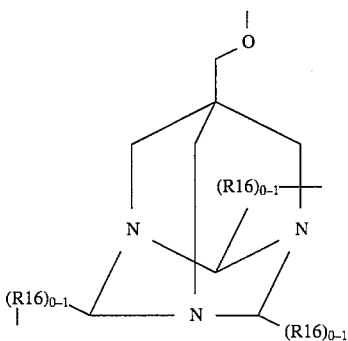

wherein R16 is a $C_1$–$C_6$ alkyl.

11. A compound as recited in claim 8, wherein R13 is selected from a group consisting of paramagnetic metal-ion chelators and nitroxides.

12. A compound having the structure:

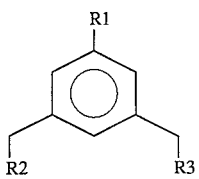

wherein:
(a) R1 is selected from a group consisting of:
R2,
R3, and
groups having the structure —(R4)$_{0-1}$—(R5)$_{0-1}$—R6(—R7)$_{0-1}$ wherein R4 is selected from a group consisting of C(O)—NH, C(S)—NH, C(O), O, NH—C(O), NH—C(S), NH—C(S)—NH, NH—C(O)—NH, C(O)—O, and O—C(O); R5 is selected from a group consisting of aryls, aryl-($C_1$–$C_{20}$ alkyls), ($C_1$–$C_{20}$ alkyl)-aryls, cycloalkyls, $C_1$–$C_{20}$ alkyls, and combinations thereof; R6 is selected from a group consisting of H, $C_1$–$C_6$ alkyls, C(O)—OH, C(O)—O—($C_1$–$C_6$ alkyls), C(O)—O$^-$ X$^+$, NH$_2$, NO$_2$, NCS, NCO, OH, SH, B(OH)$_2$, and R4, wherein X is a monovalent metal cation; and R7 is selected from a group consisting of polypeptides, proteins, antibodies, nucleic acids, carbohydrates, fatty acids, surfactants, glycerides, porphyrins, steroids, and enzyme inhibitors; and (b) R2 and R3, which are the same or different, each has the structure

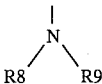

wherein R8 and R9, which are the same or different, are a hydrogen or a group having the structure —R10—(R11)—(R12)$_{0-1}$—(R13)$_n$ and at least one of said R8 and R9 groups has the —R10—(R11)—(R12)$_{0-1}$—(R13)$_n$ structure, wherein R10 is at least one structure selected from a group consisting of linkers and branch groups, the linkers having the structure —(R14)$_{0-1}$—R15— or —R15—(R14)$_{0-1}$—, wherein R14 is an aryl, a $C_1$–$C_{12}$ alkyl, an aryl-($C_1$–$C_{12}$ alkyl), a cycloalkyl, or a ($C_1$–$C_{12}$ alkyl)-aryl or a combination thereof covalently bonded together in a series manner; and R15 is selected from a group consisting of C(O)—NH, C(S)—NH, C(O), NH—C(O), NH—C(S), NH—C(S)—NH, NH—C(O)—NH, NH—C(O)—O, O—C(O)—NH, C(O)—O, and O—C(O); and the branch groups having a structure selected from a group consisting of

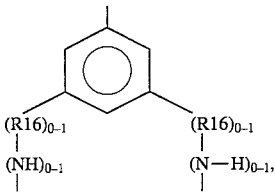

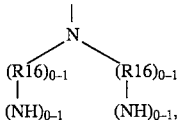

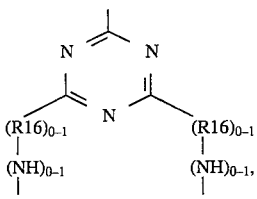

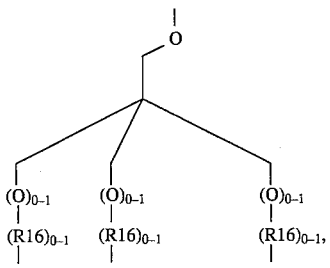

-continued

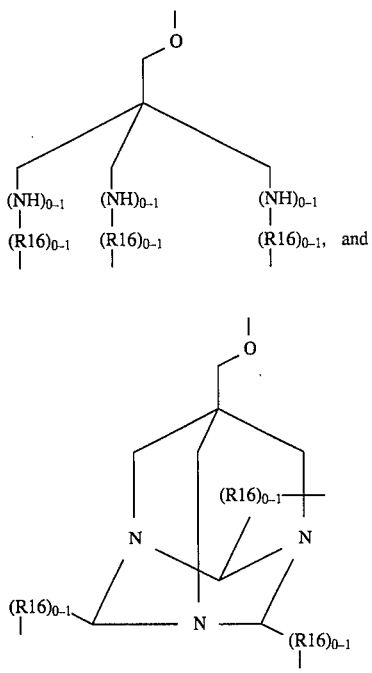

wherein R16 is a $C_1$–$C_6$ alkyl; the linkers and branch groups, when more than one of either or both is present in R10, being covalently bonded together in a series manner to form R10;

R11 is selected from a group consisting of —NH—C(O)—, —C(O)—NH—, —C(O)—, —NH—C(S)—, —C(S)—NH—, —NH—C(O)—NH—, —NH—C(S)—NH—, —NH—C(O)—O—, —O—C(O)—NH—, —C(O)—O—, and —O—C(O)—;

R12 is an aryl, $C_1$–$C_{12}$ alkyl, ($C_1$–$C_{12}$ alkyl)-aryl, cycloalkyl, aryl-($C_1$–$C_{12}$ alkyl), or a combination thereof; and R13 is selected from a group consisting of paramagnetic metal-ion chelators and nitroxides, and n is 1 or 2.

13. A compound as recited in claim 12 wherein R13 is a paramagnetic metal-ion chelator.

14. A compound as recited in claim 13 wherein n=1.

15. A compound as recited in claim 12 wherein R13 is a nitroxide.

16. A compound as recited in claim 15 wherein n=2.

17. A compound as recited in claim 12 wherein R7 is a fatty acid bonded to a biomolecule by hydrophobic interactions between R7 and the biomolecule.

18. A compound as recited in claim 17 wherein the biomolecule is an antibody molecule.

19. A compound as recited in claim 17 wherein the biomolecule is an albumin molecule.

20. A composition of matter comprising a compound as recited in claim 12 in a physiologically compatible carrier.

21. A compound as recited in claim 12 capable of decreasing a T1 or T2 relaxation time of protons present in a physiological environment containing said compound.

22. A compound of the formula:

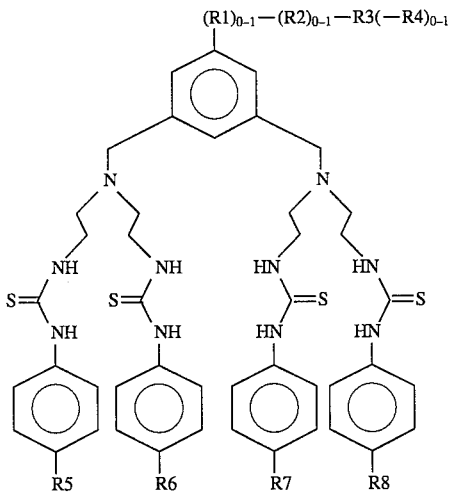

wherein:
(a) R1 is selected from a group consisting of C(O)—NH, C(S)—NH, C(O), O, NH—C(O), NH—C(S), NH—C(S)—NH, NH—C(O)—NH, C(O)—O, and O—C(O);
R2 is selected from a group consisting of aryls, aryl-($C_1$–$C_{20}$ alkyls), ($C_1$–$C_{20}$ alkyl)-aryls, cycloalkyls, $C_1$–$C_{20}$ alkyls, and combinations thereof;
R3 is selected from a group consisting of R1, H, $C_1$–$C_6$ alkyls, C(O)—OH, C(O)—O—($C_1$–$C_6$ alkyls), C(O)—O$^-$X$^+$, NH$_2$, NO$_2$, NCS, NCO, OH, SH, B(OH)$_2$, wherein X is a monovalent metal cation; and
R4 is a targeting group; and
(b) R5, R6, R7, and R8, which are the same or different, are each a nitroxide or a paramagnetic metal-ion chelator.

23. A compound as recited in claim 22 wherein R4 is selected from a group consisting of polypeptides, proteins, antibodies, nucleic acids, carbohydrates, fatty acids, surfactants, glycerides, steroids, porphyrins, and enzyme inhibitors.

24. A compound as recited in claim 22 wherein R5, R6, R7, and R8 are each the same and have the structure:

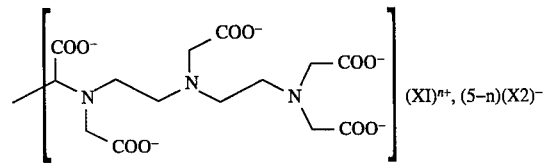

wherein:
X1 is a paramagnetic metal ion selected from a group consisting of Gd(III), Mn(II), Mn(III), Fe(III), Cr(III), Cu(II), Co(II), Ni(II), Dy(III), Tb(III), Ho(III), Er(III), Eu(III), and Nd(III),
n is an integer corresponding to the number of positive charges borne by the paramagnetic metal ion, and
X2 is a monovalent metal cation.

25. A compound as recited in claim 24 wherein X1 is Gd(III).

26. A method for obtaining an MRI image of tissues in a warm-blooded animal subject, the method comprising:
(a) providing a composition of matter as recited in claim 7;

(b) administering the composition of step (a) to the subject; and (c) obtaining an MRI image of the subject.

27. A method for obtaining an MRI image of tissues in a warm-blooded animal subject, the method comprising:

(a) providing molecules of a compound as recited in claim 11;

(b) adding the molecules of step (a) to a physiologically compatible carrier;

(c) administering the product of step (b) to the subject; and (d) obtaining an MRI image of the subject.

28. A method for obtaining an MRI image of tissues in a warm-blooded animal subject, the method comprising:

(a) providing molecules of a compound as recited in claim 12;

(b) adding the molecules of step (a) to a physiologically compatible carrier;

(c) administering the product of step (b) to the subject; and (d) obtaining an MRI image of the subject.

29. A method for obtaining an MRI image of tissues in a warm-blooded animal subject, the method comprising:

(a) providing a composition of matter as recited in claim 20;

(b) administering the composition of step (a) to the subject; and (c) obtaining an MRI image of the subject.

30. A method for obtaining an MRI image of tissues in a warm-blooded animal subject, the method comprising:

(a) providing molecules of a compound as recited in claim 22;

(b) adding the molecules of step (a) to a physiologically compatible carrier;

(c) administering the product of step (b) to the subject; and (d) obtaining an MRI image of the subject.

* * * * *

UNITED STATES PATENT AND TRADEMARK OFFICE
CERTIFICATE OF CORRECTION

PATENT NO. : 5,567,411

Page 1 of 11

DATED : October 22, 1996

INVENTOR(S) : Keana et al.

It is certified that error appears in the above-identified patent and that said Letters Patent is hereby corrected as shown below:

On the Cover Page:

[56] References Cited, Foreign Patent Documents, "0279307A2 8/1977" should be --0279307A2 8/1988--.

[56] References Cited, Foreign Patent Documents, "2137612" should be --2137612A--.

In the Specification:

Column 4, lines 26-27, "R10—(R11)—(R12)$_{0.1}$(R13)$_n$" should be -- R10—(R11)—(R12)$_{0.1}$—(R13)$_n$ --.

Column 4, lines 28-29, "R10—(R11)—(R12)$_{0.1}$(R13)$_n$" should be -- R10—(R11)—(R12)$_{0.1}$—(R13)$_n$ --.

Column 4, line 46, "—R15—(R14)$_{0.1}$" should be -- —R15—(R14)$_{0.1}$— --.

Column 9, line 10, "i.e." should be --I.e.--.

Column 9, line 55, "*J Mag. Reson Imaging*" should be --*J. Mag. Reson. Imaging*--.

Column 10, line 5, "ethylene-bis(2-hydroxyphenylglycine)" should be -- ethylene-bis-(2-hydroxyphenylglycine) --.

Column 10, line 33, "i.e." should be --I.e.--.

Column 11, line 33, " R" " should be -- R''' --.

Column 12, line 45, "(—N$_2$)" should be -- (—NH$_2$) --.

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

In column 15, line 36 to line 49, the compound should be:

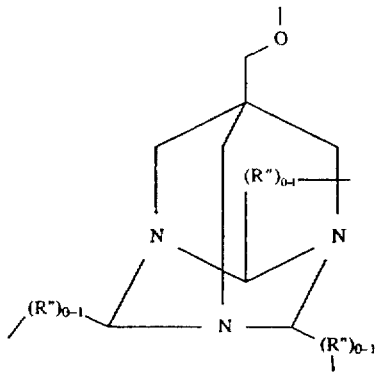

Column 18, line 2, "in situ" should be --*in situ*--.

Column 21, lines 43-46, "4-(2',2',5',5'-tetramethyl-1-oxyl-3'-imidazoline-4'-carbonyl)aminomethyl benzoic acid" should be -- 4-(2',2',5',5'-tetramethyl-1'-oxyl-3'-imidazoline-4'-carbonyl)aminomethyl benzoic acid --.

In column 21, Scheme 3, lines 55-67, the right-most compound should be:

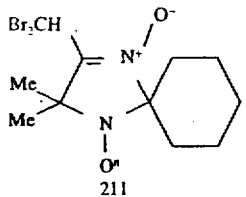

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

Column 23, line 53, "$C_{11}H_{17}N_2O_2{}^{79}Br^{31}Br$: 369.0304" should be --$C_{11}H_{17}N_2O_2{}^{79}Br^{81}Br$: 369.0304--.

In column 25, Scheme 4, lines 58-67, the left-hand compound should be:

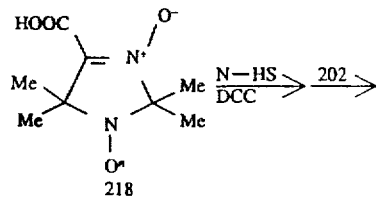

In column 29, Scheme 6, lines 21-26, the compound should be:

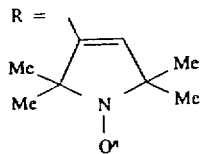

In column 31, Scheme 7, lines 41-46, the compound should be:

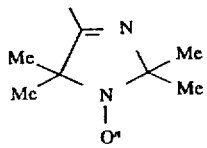

UNITED STATES PATENT AND TRADEMARK OFFICE
CERTIFICATE OF CORRECTION

Page 4 of 11

PATENT NO.   : 5,567,411

DATED        : October 22, 1996

INVENTOR(S)  : Keana et al.

It is certified that error appears in the above-identified patent and that said Letters Patent is hereby corrected as shown below:

In column 31, Scheme 7, lines 47-53, the compound should be:

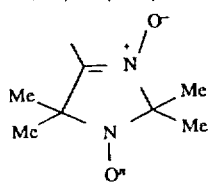

In column 31, Scheme 7, lines 54-61, the compound should be:

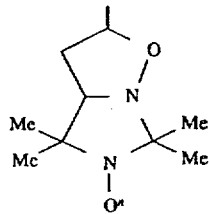

Column 32, line 15, "$a_N 14.3$" should be --$a_N = 14.3$--.

Column 33, line 5, "mp 206°-207√ C." should be --mp 206-207 °C--.

In column 33, Scheme 8, lines 40-45, the compound should be:

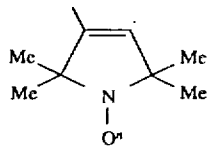

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

Column 34, line 63, "(0 435 g, 1 mmol)" should be --(0.435 g, 1 mmol)--.

In column 37, Scheme 9, lines 20-25, the compound should be:

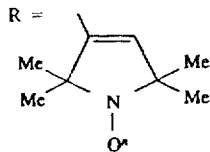

Column 38, lines 30-31, "methyl 4-{N',N'-bis[3"-[2",2",5",5"-tetramethyl-1-oxyl-3-pyrroline-4-carbonyl]aminoethyl]}ureidomethyl benzoate" should be -- methyl 4-{N',N'-bis[3'-[2",2",5",5"-tetramethyl-1-oxyl-3-pyrroline-4-carbonyl]aminoethyl]}ureidomethyl benzoate --.

Column 39, line 8, "245" should be --248--.

In columns 39 and 40, Scheme 10, lines 23-29, the right-most compound should be:

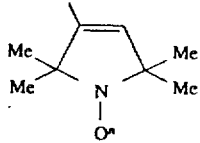

In columns 39 and 40, Scheme 10, lines 38-43, the right-most compound should be:

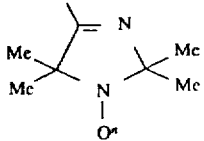

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

In columns 39 and 40, Scheme 10, lines 49-57    the left-most compound should be:

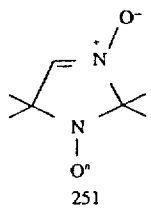

251

In columns 39 and 40, Scheme 10, lines 48-56    the right-most compound should be:

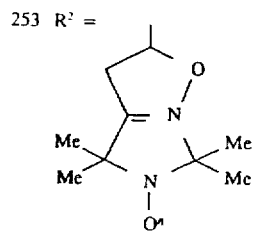

253 $R^2$ =

Column 39, lines 60-61, "NHS ester (2,810 g, 10 mmol)" should be --NHS ester 201 (2.810 g, 10 mmol)--.

Column 42, line 51    compound" should be --compound 255--.

Column 43, line 2, "($C_{53}H_{80}N_{10}O_{10}$: +5H) 1021.6;" should be --($C_{53}H_{80}N_{10}O_{10}$: + 5H): 1021.6;--.

Column 43, line 64, "(hr.)" should be --(br.)--.

Column 46, line 51, "hexaradical ester 251" should be --hexaradical ester 261--.

Column 46, line 63, "0 to 60 B" should be --0 to 60 % B--.

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

Column 47, line 1, "acid 265" should be --acid 256--.

In columns 49-50, Scheme 14, compound "254" should be compound --264--.

Column 53, lines 11-13, "methyl 3,5-bis-{[3',5'-bis-[2"-(2",2",5",5"-tetramethyl-1"-oxyl-3"-pyrroline-4"-carbonyl]aminoethyl]benzoylamino}methyl benzoate," should be --methyl 3,5-bis{[3',5'-bis-[2"-(2"',2"',5"',5"'-tetramethyl-1"'-oxyl-3"'-pyrroline-4"'-carbonyl)aminoethyl]benzoylamino}methyl benzoate,--.

Column 53, line 17, "$C_{116}N_{170}N_{22}O_{20}$:" should be --$C_{116}H_{170}N_{22}O_{20}$:--.

Column 54, lines 4-6, "3,5-bis-{[3',5'-bis-[2"-(2",2",5",5"-tetramethyl-1"-oxyl-3"-pyrroline-4"-carbonyl]aminoethyl]benzoylamino}methyl benzoic acid" should be --3,5-bis{[3',5'-bis-[2"-(2"',2"',5"',5"'-tetramethyl-1"'-oxyl-3"'-pyrroline-4"'-carbonyl)aminoethyl]benzoylamino}methyl benzoic acid--.

Column 56, line 2, "compound In" should be --compound 202. In--.

Column 61, line 7, "$C_{15}Om$:" should be --$C_{36}H_{49}N_5O_{13}$:--.

Column 61, line 16, "salt)phenyl]urea," should be --salt)-phenyl] urea,--.

Column 61, lines 37-38, "sodium N-(4-carboxybenzyl),N'-[4,-methylene-(DTPA-gadolinium-disodium salt)-phenyl] urea" should be --sodium N-(4-carboxybenzyl),N'-[4'-methylene-(DTPA-gadolinium-disodium salt)-phenyl] urea--.

Column 63, line 58, "0.03 mM" should be --0.03 m*M*--.

Column 64, line 61, "p-toluidine" should be --*p*-toluidine--.

Column 66, line 10, "nitro-m-xylene" should be --nitro-*m*-xylene--.

Column 66, line 26, "p-toluidine" should be --*p*-toluidine--.

Column 66, line 27, "29" should be --291--.

Page 7 of 11

UNITED STATES PATENT AND TRADEMARK OFFICE
CERTIFICATE OF CORRECTION

Page 8 of 11

PATENT NO. : 5,567,411

DATED : October 22, 1996

INVENTOR(S) : Keana et al.

It is certified that error appears in the above-identified patent and that said Letters Patent is hereby corrected as shown below:

In columns 67-68, Scheme 19, lines 6-12, the left-most compound should be:

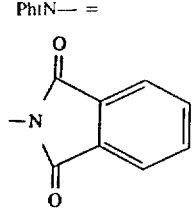

Column 67, line 28, "5-nitro-m-xylene" should be --5-nitro-*m*-xylene--.

Column 68, line 37, "(D2O)" should be --(D$_2$O)--.

Column 68, line 58, "(CDCl,)" should be --(CDCl$_3$)--.

Column 68, line 64 and line 65 (two places), "p-toluidine" should be --*p*-toluidine--.

Column 71, line 47, "eluant: MeOH in CHCL$_3$" should be --eluant: 5 % MeOH in CHCl$_3$--.

Column 71, line 57, "299" should be --292--.

Column 73, line 51, "(e, 1H)" should be --(s, 1H)--.

Column 73, line 57, "0 °C." should be --50 °C--.

Column 75, line 1, "compound was" should be --compound 295 was--.

Column 75, line 5, "sodium salt" should be --sodium salt 302--.

Column 79, line 17, "compound" should be --compound 306).--.

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

In columns 83-84, Scheme 28, lines 20-25, the arrow labeled "hydrolysis" should point toward compound 319, 320.

In column 87, Scheme 30, line 14, "pNB" should be --pH 8--.

In column 88, Scheme 30, line 14, "pHB" should be --pH 8--.

In column 90, Scheme 31, line 31, "pHZ" should be --pH 8--.

In column 90, Scheme 31, line 56-62, compound "366" should be compound --266--, and should be:

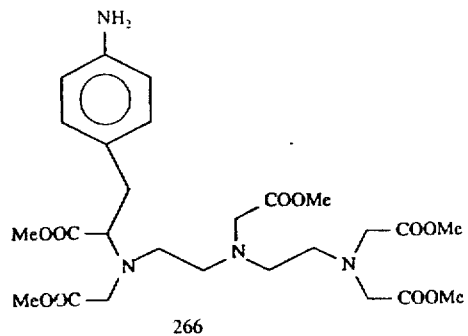

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

In column 91, Scheme 32, lines 38-53, compound 344 should be:

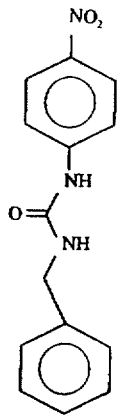

344

UNITED STATES PATENT AND TRADEMARK OFFICE
CERTIFICATE OF CORRECTION

PATENT NO. : 5,567,411

DATED : October 22, 1996

INVENTOR(S) : Keana et al.

It is certified that error appears in the above-identified patent and that said Letters Patent is hereby corrected as shown below:

Column 94, line 62, "Bioconjugate Chem. 1:65" should be --*Bioconjugate Chem.* 1:65--.

<u>In the Claims:</u>

Column 98, line 11, claim 8, "R11)" should be --(R11)--.

Signed and Sealed this

Seventh Day of September, 1999

Q. TODD DICKINSON

Attest:

Attesting Officer

Acting Commissioner of Patents and Trademarks